US009745608B2

(12) United States Patent
Wittmann et al.

(10) Patent No.: US 9,745,608 B2
(45) Date of Patent: *Aug. 29, 2017

(54) PROCESSES AND RECOMBINANT MICROORGANISMS FOR THE PRODUCTION OF CADAVERINE

(75) Inventors: Christoph Wittmann, Wolfenbuettel (DE); Stefanie Kind, Braunschweig (DE)

(73) Assignee: BASF SE, Ludwigshafen (DE)

( * ) Notice: Subject to any disclaimer, the term of this patent is extended or adjusted under 35 U.S.C. 154(b) by 676 days.

This patent is subject to a terminal disclaimer.

(21) Appl. No.: 13/985,330

(22) PCT Filed: Feb. 20, 2012

(86) PCT No.: PCT/IB2012/050763
§ 371 (c)(1),
(2), (4) Date: Feb. 3, 2014

(87) PCT Pub. No.: WO2012/114256
PCT Pub. Date: Aug. 30, 2012

(65) Prior Publication Data
US 2014/0134682 A1 May 15, 2014

Related U.S. Application Data

(60) Provisional application No. 61/445,098, filed on Feb. 22, 2011.

(30) Foreign Application Priority Data

Feb. 22, 2011 (EP) ..................................... 11155432

(51) Int. Cl.
| C12N 1/20 | (2006.01) |
| C12N 15/00 | (2006.01) |
| C12P 13/02 | (2006.01) |
| C07H 21/04 | (2006.01) |
| A61K 38/00 | (2006.01) |
| C12N 15/77 | (2006.01) |
| C12N 9/88 | (2006.01) |
| C07K 14/34 | (2006.01) |
| C12P 13/00 | (2006.01) |

(52) U.S. Cl.
CPC .............. *C12P 13/02* (2013.01); *C07K 14/34* (2013.01); *C12N 9/88* (2013.01); *C12N 15/77* (2013.01); *C12P 13/001* (2013.01)

(58) Field of Classification Search
None
See application file for complete search history.

(56) References Cited

U.S. PATENT DOCUMENTS

| 6,858,406 B1 | 2/2005 | Vrlijc et al. |
| 6,893,848 B1 | 5/2005 | Yokoi et al. |
| 7,332,310 B2 * | 2/2008 | Nakagawa ............. C07K 14/34 435/115 |
| 7,435,584 B2 | 10/2008 | Kruetzer et al. |
| 2009/0246838 A1 | 10/2009 | Zelder et al. |
| 2011/0039313 A1 | 2/2011 | Verseck et al. |

FOREIGN PATENT DOCUMENTS

| CN | 101240258 A | 8/2008 |
| CN | 101389765 A | 3/2009 |
| DE | 195 48 222 A1 | 6/1997 |
| EP | 1 108 790 A2 | 6/2001 |
| JP | 2002223770 A | 8/2002 |
| JP | 2004222569 A | 8/2004 |
| WO | WO-97/23597 A2 | 7/1997 |
| WO | WO-00/63388 A1 | 10/2000 |
| WO | WO-03/040373 A2 | 5/2003 |
| WO | WO-2005/073390 A2 | 8/2005 |
| WO | WO-2007/113127 A1 | 10/2007 |
| WO | WO-2008/092720 A1 | 8/2008 |
| WO | WO-2011/073278 A1 | 6/2011 |

OTHER PUBLICATIONS

Branden et al. Introduction to Protein Structure, Garland Publishing Inc., New York, p. 247, 1991.*
Becker, J, et al., "Metabolic Responses to Pyruvate Kinase Deletionin Lysine Producing *Corynebacterium glutamicum*, Microbial Cell Factories,"2005, vol. 7, No. 8, pp. 1-15.
Clifton, I, et al., "Structure of Proline 3-Hydroxylase Evolution of the Family of 2-Oxoglutarate Dependent Oxygenases," *European Journal of Biochemistry*, 2001, vol. 268, pp. 6625-6636.
Eggeling, L., et al., "The Cell Wall Barrier of *Corynebacterium glutamicum* and Amino Acid Efflux," *Journal of Bioscience and Bioengineering*, 2001, vol. 92, No. 3, pp. 201-213.
Eggeling, L., et al., "New Ubiquitous Translocators: Amino Acid Export by *Corynebacterium glutamicum* and *Escherichia coli*," *Archives of Microbiology*, 2003, vol. 180, No. 3, pp. 155-160.
Jenkins, M., et al., "Purification and Properties of Homoserine Dehydrogenase from *Neurospora Crassa*," *Biochimica Et Biophysica Acta*, 1970, vol. 212, pp. 21-32.
Jiang, Li-Li, et al, "Producing Cadaverine by Cell Immobilization of Lysine Decarboxylase," *Fine Chemicals*, 2007, vol. 24, No. 11, pp. 1080-1084. (English abstract at p. 1080).
Kawaguchi, H., et al., "Engineering of a Xylose Metabolic Pathway in *Corynebacterium gutamicum*, Applied and Environmental Microbiology," 2006, vol. 72, No. 5, pp. 3418-3428.

(Continued)

*Primary Examiner* — Yong Pak
(74) *Attorney, Agent, or Firm* — Marshall, Gerstein & Borun LLP

(57) ABSTRACT

Recombinant microorganisms comprising DNA molecules in a deregulated form which improve the production of cadaverine or N-acetylcadaverine, as well as recombinant DNA molecules and polypeptides used to produce the microorganisms are provided. Said microorganisms comprise an intracellular lysine decarboxylase activity and a deregulated cadaverine export activity, or comprise a decreased cadaverine export activity and an enhanced N-acetylcadaverine forming activity. Processes for the production of cadaverine N-acetylcadaverine using the recombinant microorganisms are also provided.

3 Claims, 2 Drawing Sheets

(56) References Cited

OTHER PUBLICATIONS

Kawaguchi, H., et al., "Engineering of an L-Arabinose Metabolic Pathway in *Corynebacterium glutamicum*," *Applied Microbiology and Biotechnology*, 2008, vol. 5, No. 77, pp. 1053-1062.

Kawaguchi, H., et al., "Identification and Functional Analysis of the Gene Cluster for L-Arabinose Utilization in *Corynebacterium glutamicum*," *Applied and Environmental Microbiology*, 2009, vol. 11, No. 75, pp. 3419-3429.

Kind, S. et al., "Identification and Elimination of the Competing N-Acetyldiaminopentane Pathway for Improved Production of Diaminopentane by *Corynebacterium glutamicum*," *Applied and Environmental Microbiology*, 2010, vol. 76, No. 15, pp. 5175-5180.

Kind, S., et al., "Metabolic Engineering of Cellular Transport for Overproduction of the Platform Chemical 1,5-Diaminopentanein *Corynebacterium glutamicum*," *Metabolic Engineering*, 2011, vol. 13, pp. 617-627.

Meneely, K., et al., "Biochemical Characterization of a Flavin Adenine Dinculeotide-Dependent Monooxygenase, Ornithine Hydroxylase from *Pseudomonas aeruginosa*, Suggests a Novel Reaction Mechanism," *Biochemistry*, 2007, vol. 46, pp. 11930-11937.

Niu, Tao, et al., "Construction of Recombinant *Corynebacterium glutamicum* producing 1,5-pentanediamine by one step method," *China Biotechnology*, 2010, vol. 30, No. 8, pp. 93-99. (English abstract at p. 99).

Sasaki, M., et al., "Simultaneous Utilization of D-Cellobiose, D-Glucose, and D-Xylose by Recombinant *Corynebacterium glutamicum* Under Oxygen-Deprived Conditions," *Applied Microbiology and Biotechnology*, 2008, vol. 81, No. 4, pp. 691-699.

Soksawatmaekhin, W., et al., Excretion and Uptake of Cadaverine by CadB and its Physiological Functions in *Escherichia coli*, *Molecular* Microbiology, 2004, vol. 51, No. 5, pp. 1401-1412.

Soksawatmaekhin, W., et al., "Identification of the Cadaverine Recognition Site on the Cadaverine-Lysine Antiporter CadB," *The Journal of Biological Chemistry*, 2006, vol. 281, No. 39, pp. 29213-29220.

* cited by examiner

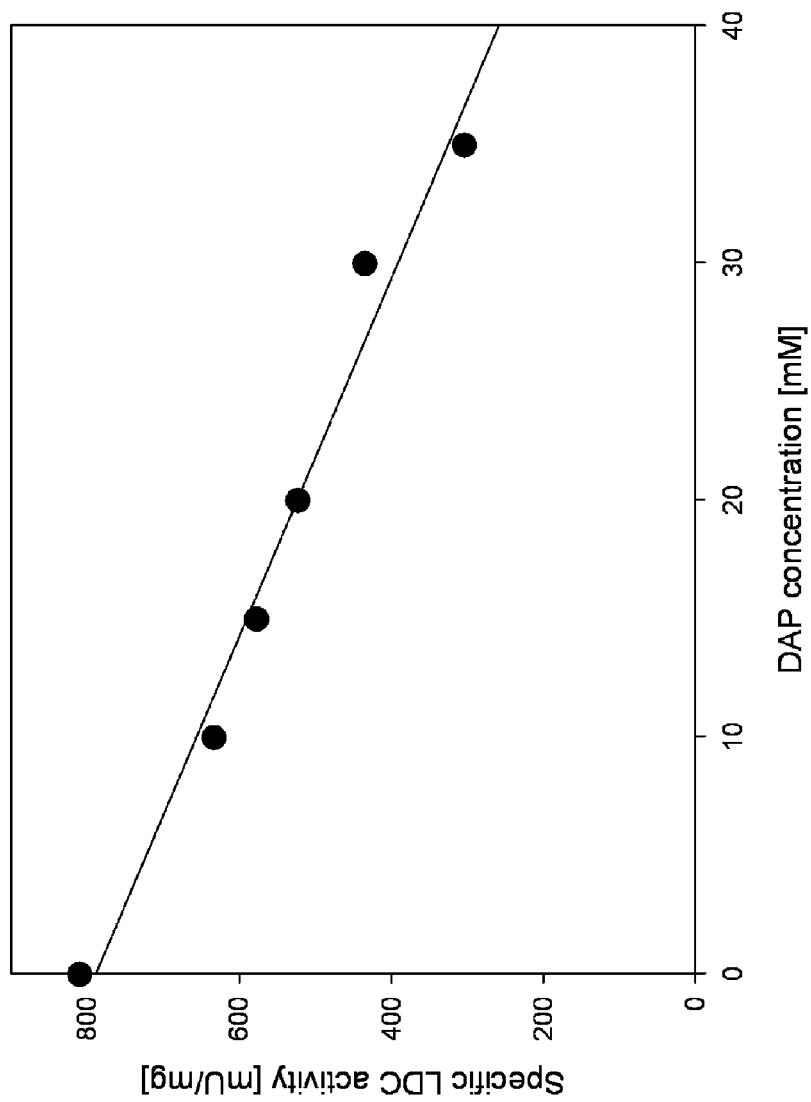
Figure 1: Dependence of specific lysine decarboxylase activity on present diaminopentane in diaminopentane producing C. glutamicum DAP-3c.

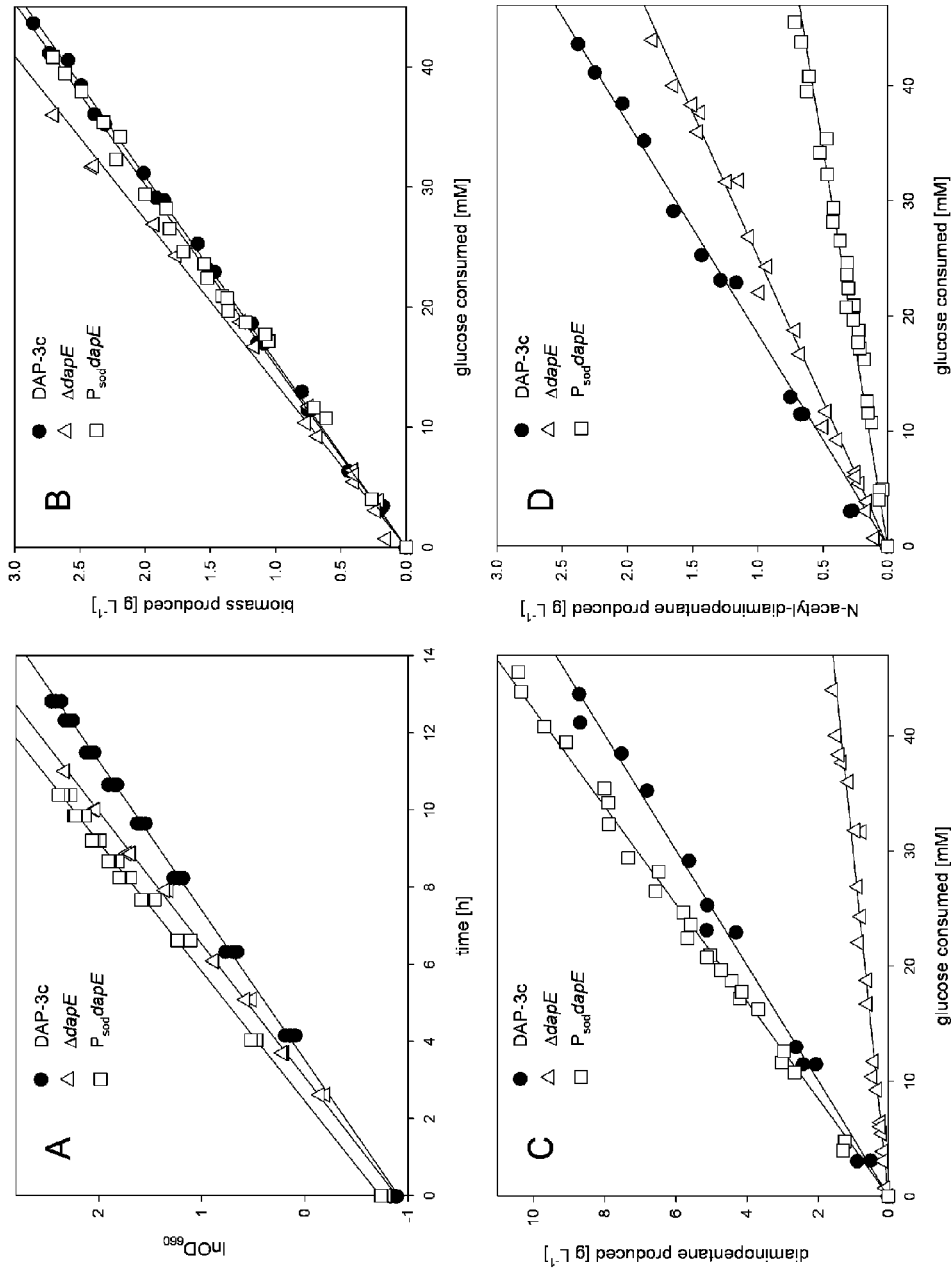
Figure 2: Comparison of growth (A), biomass yield (B), diaminopentane (C) and N-acetyl-diaminopentane yield (D) of C. glutamicum deltadapE, carrying a deletion of the cadaverine exporter polypeptide (diaminopentane exporter), and $P_{sod}dapE$, overexpressing the cadaverine exporter polypeptide under the sod promoter, and their parent strain DAP-3c.

PROCESSES AND RECOMBINANT MICROORGANISMS FOR THE PRODUCTION OF CADAVERINE

CROSS-REFERENCE TO RELATED APPLICATIONS

This application is the U.S. national phase of PCT/IB2012/050763, filed Feb. 20, 2012, which claims the benefit of U.S. Provisional Patent Application No. 61/445,098, filed Feb. 22, 2011, incorporated herein by reference in its entirety, and European Patent Application No. 11155432.5, filed Feb. 22, 2011.

FIELD OF THE INVENTION

The present invention relates to the use of recombinant microorganisms comprising DNA molecules in a deregulated form which improve the production of cadaverine or N-acetylcadaverine, as well as to recombinant DNA molecules and polypeptides used to produce the microorganism, said microorganism comprising an intracellular lysine decarboxylase activity and a deregulated cadaverine export activity or comprising a decreased cadaverine export activity and an enhanced N-acetylcadaverine forming activity. The present invention also relates to processes for the production of cadaverine or N-acetylcadaverine using recombinant microorganisms.

PRIOR ART

JP 2002223770 discloses a method for producing cadaverine by introducing a lysine decarboxylation gene and/or a lysine-cadaverine antiporter gene into a lysine producing microorganism.

JP 2004222569 discloses a method for producing cadaverine by culturing recombinant coryneform bacteria having L-lysine decarboxylase activity and a homoserine auxotrophy. WO 2007113127 discloses a method for producing cadaverine by culturing recombinant coryneform bacteria having a deregulated L-lysine decarboxylase activity, the detection of a cadaverine acetyltransferase and its deletion to improve cadaverine production.

U.S. Pat. No. 7,435,584, disclosing a method for enhanced production of L-lysine by culturing *corynebacteria* having a high expression of the lysE (lysine export carrier) gene.

WO 2008092720 discloses a method for producing cadaverine by fermenting high lysine producing microorganisms expressing an intracellular expressed decarboxylase, whereby such microorganisms may have a reduced or eliminated expression of a lysine/cadaverine antiporter.

SUMMARY OF THE INVENTION

In one aspect, the present invention provides a microorganism having a deregulated cadaverine export activity. Preferably the deregulated cadaverine exporter activity is at least partially due to deregulation of one or more cadaverine exporter polypeptides comprising an amino acid sequence being at least 80% identical to SEQ ID NO: 1. In one embodiment of the invention, the microorganism has an enhanced cadaverine exporter activity, while in another embodiment of the invention the microorganism has a decreased cadaverine exporter activity. Preferably the microorganism has an enhanced lysine decarboxylase activity, even more preferred, the enhanced lysine decarboxylase activity is due to expression of one or more lysine decarboxylase polypeptides comprising an amino acid sequence being at least 80% identical to SEQ ID NO: 3 or SEQ ID NO: 4. In a further embodiment of the invention, the microorganism described above have also at least one deregulated gene selected from the group consisting of the genes of aspartokinase, aspartatesemialdehyde dehydrogenase, dihydrodipicolinate synthase, dihydrodipicolinate reductase, tetrahydrodipicolinate succinylase, succinyl-amino-ketopimelate transaminase, succinyl-diamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase, homoserine dehydrogenase, phophoenolpyruvate carboxykinase, succinyl-CoA synthetase, methylmalonyl-CoA mutase, diamine acetyltransferase. Preferably the microorganisms described above have an enhanced lysine import activity. In an even more preferred embodiment, the microorganism has an enhanced lysine import activity being at least partially due to a decreased lysine exporter activity or an enhanced lysine permease activity or an enhanced lysine/cadaverin antiporter activity or any combination thereof. The enhanced lysine import activity is preferably due to a decreased activity of at least one lysine exporter polypeptide comprising an amino acid sequence which has at least 80% identity to SEQ ID NO: 5. In another embodiment of the invention, the microorganisms described above have an enhanced lysine import activity, being at least partially due to an enhanced lysine permease activity or at least partially due to an enhanced lysine/cadaverin antiporter activity or a combination of both.

The invention comprises further microorganisms, as described above, having further a deregulated N-acetylcadaverine-forming activity. In one embodiment of the invention the microorganism having a deregulated N-acetylcadaverine-forming activity has no, or a decreased N-acetylcadaverine-forming activity. In another embodiment of the invention, the microorganism having a deregulated N-acetylcadaverine-forming activity has an enhanced N-acetylcadaverine-forming activity and a decreased cadaverine exporter activity. Preferably the deregulated N-acetylcadaverine-forming activity of the microorganism described above is at least partially due to deregulation of a N-acetylcadaverine-forming polypeptide comprising an amino acid sequence, being at least 80% identical to SEQ ID NO: 13. Preferably any one of the microorganism described above belongs to the Glade Eubacteria, even more preferred, to the genus *Corynebacterium*, most preferred the microorganism described above belongs to the species *Corynebacterium glutamicum*.

The invention comprises further a process for the production of cadaverine using any one of the microorganism described above and a process for the production of N-acetylcadaverine using any one of the microorganism described above. Further the invention comprises the use of any one of the microorganism described above for the production of cadaverine or N-acetylcadaverine.

Other embodiments of the invention are the use of the cadaverine produced by fermenting any one of the microorganism described above and polyamines produced by using cadaverine produced by fermenting any one of the microorganism described above.

BRIEF DESCRIPTION OF THE DRAWINGS

FIG. 1: Dependence of specific lysine decarboxylase activity on present diaminopentane in diaminopentane producing C. glutamicum DAP-3c. The data represent mean values from two replicates.

FIG. 2: Comparison of growth (A), biomass yield (B), diaminopentane (C) and N-acetyldiaminopentane yield (D) of C. glutamicum$_{delta}$ dapE, carrying a deletion of the cadaverine exporter polypeptide of SEQ ID NO: 1 (diaminopentane exporter), and P$_{sod}$dapE, overexpressing the cadaverine exporter gene of SEQ ID NO: 2 coding for the polypeptide of SEQ ID NO: 1 under the sod promoter, and their parent strain DAP-3c. The data represent values of the exponential growth phase from three biological replicates cultivated in minimal medium with 10 g L−1 glucose as sole carbon source.

DETAILED DESCRIPTION OF THE INVENTION

In the description that follows, a number of terms are utilized extensively. Definitions are herein provided to facilitate understanding of the invention.

The term cadaverine means 1,5-diaminopentane (CAS-Number: 462-94-2).

The term N-acetylcadaverine means N-acetyldiaminopentan (CAS-Number: 102029-76-5)

The methodologies of the present invention feature recombinant microorganisms, preferably including vectors or genes (e.g., wild-type and/or mutated genes) as described herein and/or cultured in a manner which results in the production of cadaverine and/or N-acetylcadaverine.

The term "recombinant" microorganism includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived.

Promoter. A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent, if the promoter is a constitutive promoter.

Enhancer. A promoter element. An enhancer can increase the efficiency with which a particular gene is transcribed into mRNA irrespective of the distance or orientation of the enhancer relative to the start site of transcription.

Cloning vector. A DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Expression vector. A DNA molecule comprising a cloned structural gene encoding a foreign protein which provides the expression of the foreign protein in a recombinant host. Typically, the expression of the cloned gene is placed under the control of (i.e. operably linked to) certain regulatory sequences such as promoter and enhancer sequences. Promoter sequences may be either constitutive or inducible.

Recombinant host. A recombinant host may be any prokaryotic or eukaryotic cell which contains either a cloning vector or an expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989) ["Sambrook"].

The terms "express," "expressing," "expressed" and "expression" refer to expression of a gene product (e.g., a biosynthetic enzyme of a gene of a pathway or reaction defined and described in this application) at a level that the resulting enzyme activity of this protein encoded for, or the pathway or reaction that it refers to allows metabolic flux through this pathway or reaction in the organism in which this gene/pathway is expressed in. The expression can be done by genetic alteration of the microorganism that is used as a starting organism. In some embodiments, a microorganism can be genetically altered (e.g., genetically engineered) to express a gene product at an increased level relative to that produced by the starting microorganism or in a comparable microorganism which has not been altered. Genetic alteration includes, but is not limited to, altering or modifying regulatory sequences or sites associated with expression of a particular gene (e.g. by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins).

In some embodiments, a microorganism can be physically or environmentally altered to express a gene product at an increased or lower level relative to level of expression of the gene product by the starting microorganism. For example, a microorganism can be treated with, or cultured in the presence of an agent known, or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

The terms "deregulate," "deregulated" and "deregulation" refer to alteration or modification of at least one gene in a microorganism, wherein the alteration or modification results in increasing efficiency of cadaverine or N-acetylcadaverine production in the microorganism relative to cadaverine or N-acetylcadaverine production in absence of the alteration or modification. In some embodiments, a gene that is altered or modified encodes an enzyme in a biosynthetic pathway, or a transport protein, such that the level or activity of the biosynthetic enzyme in the microorganism is altered or modified, or that the transport specificity or efficiency is altered or modified. In some embodiments, at least one gene that encodes an enzyme in a biosynthetic pathway is altered or modified such that the level or activity of the enzyme is enhanced or increased relative to the level in presence of the unaltered or wild type gene. Deregulation also includes altering the coding region of one or more genes to yield, for example, an enzyme that is feedback resistant or has a higher or lower specific activity. Also, deregulation further encompasses genetic alteration of genes encoding transcriptional factors (e.g., activators, repressors) which regulate expression of genes coding for enzymes or transport proteins.

The terms "overexpress", "overexpressing", "overexpressed" and "overexpression" refer to expression of a gene product, in particular to enhancing the expression of a gene product (e.g. a lysine biosynthetic enzyme or sulfate reduction pathway enzyme or cysteine biosynthetic enzyme or a gene or a pathway or a reaction defined and described in this application) at a level greater than that present prior to a genetic alteration of the starting microorganism. In some embodiments, a microorganism can be genetically altered (e.g., genetically engineered) to express a gene product at an increased level relative to that produced by the starting microorganism. Genetic alteration includes, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins). Another way to overexpress a gene product is to enhance the stability of the gene product to increase its life time. Examples for the overexpression of genes in organisms such as *C. glutamicum* can be found in Eikmanns et al (*Gene*. (1991) 102, 93-8).

The term "deregulated" includes expression of a gene product (e.g., lysine decarboxylase) at a level lower or higher than that expressed prior to manipulation of the microorganism or in a comparable microorganism which has not been manipulated. In one embodiment, the microorganism can be genetically manipulated (e.g., genetically engineered) to express a level of gene product at a lesser or higher level than that expressed prior to manipulation of the microorganism or in a comparable microorganism which has not been manipulated. Genetic manipulation can include, but is not limited to, altering or modifying regulatory sequences or sites associated with expression of a particular gene (e.g., by removing strong promoters, inducible promoters or multiple promoters), modifying the chromosomal location of a particular gene, altering nucleic acid sequences adjacent to a particular gene such as a ribosome binding site or transcription terminator, decreasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, or other methods to knockout or block expression of the target protein).

The term "deregulated gene activity", e.g. deregulated lysine decarboxylase, also means that a gene activity, e.g. a lysine decarboxylase activity, is introduced into a microorganism where the respective gene activity, e.g. the lysine decarboxylase activity, has not been observed before, e.g. by introducing a heterologous gene, e.g. a lysine decarboxylase gene in one or more copies into the microorganism preferably by means of genetic engineering.

The phrase "deregulated pathway or reaction" refers to a biosynthetic pathway or reaction in which at least one gene that encodes an enzyme in a biosynthetic pathway or reaction is altered or modified such that the level or activity of at least one biosynthetic enzyme is altered or modified. The phrase "deregulated pathway" includes a biosynthetic pathway in which more than one gene has been altered or modified, thereby altering level and/or activity of the corresponding gene products/enzymes. In some cases the ability to "deregulate" a pathway (e.g., to simultaneously deregulate more than one gene in a given biosynthetic pathway) in a microorganism arises from the particular phenomenon of microorganisms in which more than one enzyme (e.g., two or three biosynthetic enzymes) are encoded by genes occurring adjacent to one another on a contiguous piece of genetic material termed an "operon." In other cases, in order to deregulate a pathway, a number of genes must be deregulated in a series of sequential engineering steps.

To express the deregulated genes according to the invention, the DNA sequence encoding the enzyme must be operably linked to regulatory sequences that control transcriptional expression in an expression vector and then, introduced into either a prokaryotic or eukaryotic host cell. In addition to transcriptional regulatory sequences, such as promoters and enhancers, expression vectors can include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, T5, Sp6 and T7 polymerases, the $P_R$ and $P_L$ promoters of bacteriophage lambda, the trp, recA, heat shock, lacUV5, tac, lpp-lac pr, phoA, gal, trc and lacZ promoters of *E. coli*, the alpha-amylase and the sigma 28-specific promoters of *B. subtilis*, the promoters of the bacteriophages of *Bacillus, Streptomyces* promoters, the int promoter of bacteriophage lambda, the bla promoter of the β-lactamase gene of pBR322, and the CAT promoter of the chloramphenicol acetyl transferase gene as well as PGRO, PSOD, PEFTU, PEFTS from *Corynebacterium* and combinations of these promoters as described in WO2005059144, WO2007011939, WO2007012078, WO2005059093, WO2008049782, WO2006069711, WO2007020295. Prokaryotic promoters are reviewed by Glick, J. Ind. Microbial. 1:277 (1987); Watson et al., MOLECULAR BIOLOGY OF THE GENE, 4th Ed., Benjamin Cummins (1987); Ausubel et al., supra, and Sambrook et al., supra.

A preferred promoter for the expression of the *E. coli* lysine decarboxylase is the PsodA, the PGRO and the PEFTU promoter of *C. glutamicum* described in WO2005059144, WO2007011939, WO2007012078, WO2005059093, WO2008049782, WO2006069711, WO2007020295.

Methods for expressing proteins in prokaryotic hosts are well-known to those of skill in the art. See, for example, Williams et al., "Expression of foreign proteins in *E. coli* using plasmid vectors and purification of specific polyclonal antibodies," in DNA CLONING 2: EXPRESSION SYSTEMS, 2nd Edition, Glover et al. (eds.), pages 15-58 (Oxford University Press 1995). Also see, Ward et al., "Genetic Manipulation and Expression of Antibodies," in MONOCLONAL ANTIBODIES: PRINCIPLES AND APPLICATIONS, pages 137-185 (Wiley-Liss, Inc. 1995); and Georgiou, "Expression of Proteins in Bacteria," in PROTEIN ENGINEERING: PRINCIPLES AND PRACTICE, Cleland et al. (eds.), pages 101-127 (John Wiley & Sons, Inc. 1996). Further methods to increase or decrease gene expression and protein production can be found in WO2008049782.

An expression vector can be introduced into bacterial host cells using a variety of techniques including calcium chloride transformation, electroporation, and the like. See, for example, Ausubel et al. (eds.), SHORT PROTOCOLS IN MOLECULAR BIOLOGY, 3rd Edition, pages 1-1 to 1-24 (John Wiley & Sons, Inc. 1995).

As used herein, a substantially pure protein means that the desired purified protein is essentially free from contaminating cellular components, as evidenced by a single band following polyacrylamide-sodium dodecyl sulfate gel electrophoresis (SDS-PAGE). The term "substantially pure" is further meant to describe a molecule which is homogeneous by one or more purity or homogeneity characteristics used by those of skill in the art. For example, a substantially pure lysine decarboxylase will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of lysine decarboxylase with other compounds. In addition, the term is not meant to exclude lysine decarboxylase fusion proteins isolated from a recombinant host.

In a first aspect, the present invention provides a microorganism having an intracellular lysine decarboxylase activity and an enhanced lysine import activity or comprising an intracellular and an extracellular lysine decarboxylase activity or comprising an intracellular and an extracellular lysine decarboxylase activity and an enhanced lysine import activity The microorganism can be any prokaryotic or eukaryotic microorganism, in particular bacteria, archaea, yeasts and fungi. Preferred are microorganisms being selected from the genus of *Corynebacterium* with a particular focus on *Corynebacterium glutamicum*, the genus of *Escherichia* with a particular focus on *Escherichia coli*, the genus of *Bacillus*, particularly *Bacillus subtilis*, and the genus of *Streptomyces*.

As set out above, a preferred embodiment of the invention relates to the use of host cells which are selected from coryneform bacteria such as bacteria of the genus *Corynebacterium*. Particularly preferred are the species *Corynebacterium glutamicum, Corynebacterium acetoglutamicum, Corynebacterium acetoacidophilum, Corynebacterium callunae, Corynebacterium ammoniagenes, Corynebacterium thermoaminogenes, Corynebacterium melassecola* and *Corynebacterium effiziens*. Other preferred embodiments of the invention relate to the use of *Brevibacteria* and particularly the species *Brevibacterium flavum, Brevibacterium lactofermenturn* and *Brevibacterium divarecatum*.

In other preferred embodiments of the invention the host cells may be selected from the group comprising *Corynebacterium glutamicum* ATCC13032, *Corynebacterium acetoglutamicum* ATCC15806, *Corynebacterium acetoacidophilum* ATCC13870, *Corynebacterium thermoaminogenes* FERMBP-1539, *Corynebacterium melassecola* ATCC17965, *Corynebacterium effiziens* DSM 44547, *Corynebacterium effiziens* DSM 44549, *Brevibacterium flavum* ATCC14067, *Brevibacterium lactoformentum* ATCC13869, *Brevibacterium divarecatum* ATCC 14020, *Corynebacterium glutamicum* KFCC10065 and *Corynebacterium glutamicum* ATCC21608 as well as strains that are derived thereof by e.g. classical mutagenesis and selection or by directed mutagenesis.

Other particularly preferred strains of *Corynebacterium glutamicum* may be selected from the group comprising ATCC13058, ATCC13059, ATCC13060, ATCC21492, ATCC21513, ATCC21526, ATCC21543, ATCC13287, ATCC21851, ATCC21253, ATCC21514, ATCC21516, ATCC21299, ATCC21300, ATCC39684, ATCC21488, ATCC21649, ATCC21650, ATCC19223, ATCC13869, ATCC21157, ATCC21158, ATCC21159, ATCC21355, ATCC31808, ATCC21674, ATCC21562, ATCC21563, ATCC21564, ATCC21565, ATCC21566, ATCC21567, ATCC21568, ATCC21569, ATCC21570, ATCC21571, ATCC21572, ATCC21573, ATCC21579, ATCC19049, ATCC19050, ATCC19051, ATCC19052, ATCC19053, ATCC19054, ATCC19055, ATCC19056, ATCC19057, ATCC19058, ATCC19059, ATCC19060, ATCC19185, ATCC13286, ATCC21515, ATCC21527, ATCC21544, ATCC21492, NRRL B8183, NRRL W8182, B12NRRLB12416, NRRLB12417, NRRLB12418 and NRRLB11476.

The abbreviation KFCC stands for Korean Federation of Culture Collection, ATCC stands for American-Type Strain Culture Collection and the abbreviation DSM stands for Deutsche Sammlung von Mikroorganismen. The abbreviation NRRL stands for ARS cultures collection Northern Regional Research Laboratory, Peorea, Ill., USA.

In certain embodiments, a microorganism of the invention is a "Campbell in" or "Campbell out" microorganism (or cell or transformant). As used herein, the phrase "Campbell in" transformant shall mean a transformant of an original host cell in which an entire circular double stranded DNA molecule (for example a plasmid) has integrated into a chromosome of the cell by a single homologous recombination event (a cross in event), and which effectively results in the insertion of a linearized version of the circular DNA molecule into a first DNA sequence of the chromosome that is homologous to a first DNA sequence of the circular DNA molecule. The phrase "Campbelled in" refers to the linearized DNA sequence that has been integrated into the chromosome of the "Campbell in" transformant. A "Campbell in" transformant contains a duplication of the first homologous DNA sequence, that includes and surrounds the homologous recombination crossover point.

"Campbell out" refers a cell descended from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of the linearized insert, the second recombination event resulting in the deletion (jettisoning) of a portion of the integrated DNA sequence, but, importantly, also resulting in a portion (this can be as little as a single base) of the integrated DNA sequence remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above).

A "Campbell out" cell or strain is usually, but not necessarily, obtained by a counter selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, and so on.

The homologous recombination events that leads to a "Campbell in" or "Campbell out" can occur over a range of DNA bases within the homologous DNA sequence, and since the homologous sequences will be identical to each other for at least part of this range it is not usually possible to specify exactly where the crossover event occurred. In other words, it is not possible to specify precisely which sequence was originally from the inserted DNA, and which was originally from the chromosomal DNA. Moreover, the first homologous DNA sequence and second homologous DNA sequence are usually separated by a region of partial non-homology, and it is this region of non-homology that remains deposited in the chromosome of the "Campbell out" cell.

For practicality, in *C. glutamicum*, typical first and second homologous DNA sequence are at least about 200 base pairs in length, and can be up to several thousand base pairs in length, however, the procedure can be made to work with shorter or longer sequences. A preferred length for the first and second homologous sequences is about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

Lysine decarboxylase activity refers to the decarboxylation of L-lysine into cadaverine, which is catalyzed by a Lysine decarboxylase. The enzyme has been classified as E.C. 4.1.1.18. For example, enzymes isolated from *Escherichia coli* having lysine decarboxylase activity are the cadA gene product (Kyoto Encyclopedia of Genes and Genomes, Entry b4131, SEQ ID NO: 4) and the ldcC gene product (Kyoto Encyclopedia of Genes and Genomes, Entry JW0181 SEQ ID NO: 3).

Methods to measure and compare enzymatic activities are known in the art and are described for example in "Handbook of *Corynebacetrium glutamicum* 2005 Eggeling, Borth eds. CRC Press Boca Raton USA and references within) or in Methods in Enzymology Volume 17, Part 1 pp. 3-1098 (1970), Volume 17, Part 2, pp. 3-961 (1971) Volume 41, pp. 3-564 (1975), Volume 42 pp. 3-537 (1975), Volume 63, pp. 3-547 (1979), Volume 64, pp. 3-418 (1980), Volume 89, pp. 3-656 (1982), Volume 90 pp. 3-602 (1982), Volume 142, pp. 3-732 (1987), Volume 143 pp. 3-582 (1987) and references therein.". A standard strain used for comparison of *Corynebacterium glutamicum* strains is ATCC13032 (Handbook of *Corynebacetrium glutamicum* 2005 Eggeling, Borth eds. CRC Press Boca Raton USA) The amino acid sequences of *E. coli* ldcC is disclosed in accession number SEQ ID NO 3: and of *E. coli* cadA is disclosed in SEQ ID NO: 4.

DNA molecules encoding the *E. coli* lysine decarboxylase gene can be obtained by screening cDNA or genomic libraries with polynucleotide probes having nucleotide sequences reverse-translated from the amino acid sequence of SEQ ID NO: 3 or 4.

Alternatively, the *E. coli* lysine decarboxylase genes or any genes described herein can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., Gene 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize DNA molecules at least 2 kilobases in length. Adang et al., Plant Molec. Biol. 21:1131 (1993); Bambot et al., PCR Methods and Applications 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., PCR Methods Appl. 4:299 (1995).

Variants of polypeptides e.g. cadaverine exporter polypeptides, or variants of any gene described herein can be produced that contain conservative amino acid changes, compared with the parent enzyme. That is, variants can be obtained that contain one or more amino acid substitutions of e.g. SEQ ID NO: 1, in which an alkyl amino acid is substituted for an alkyl amino acid in the polypeptide sequence, an aromatic amino acid is substituted for an aromatic amino acid e.g. in the cadaverine exporter polypeptide amino acid sequence, a sulfur-containing amino acid is substituted for a sulfur-containing amino acid e.g in the cadaverine exporter polypeptide amino acid sequence, a hydroxy-containing amino acid is substituted for a hydroxy-containing amino acid e.g. in the cadaverine exporter polypeptide amino acid sequence, an acidic amino acid is substituted for an acidic amino acid e.g. in the cadaverine exporter polypeptide amino acid sequence, a basic amino acid is substituted for a basic amino acid e.g. in the cadaverine exporter polypeptide amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) cysteine and methionine, (4) serine and threonine, (5) aspartate and glutamate, (6) glutamine and asparagine, and (7) lysine, arginine and histidine.

Conservative amino acid changes e. g. in the cadaverine exporter polypeptide can be introduced by substituting nucleotides for the nucleotides recited in SEQ ID NO: 1. Such "conservative amino acid" variants can be obtained, for example, by oligonucleotide-directed mutagenesis, linker-scanning mutagenesis, mutagenesis using the polymerase chain reaction, and the like. Ausubel et al., supra, at pages 8.0.3-8.5.9; Ausubel et al. (eds.), SHORT PROTOCOLS IN MOLECULAR BIOLOGY, 3rd Edition, pages 8-10 to 8-22 (John Wiley & Sons, Inc. 1995). Also see generally, McPherson (ed.), DIRECTED MUTAGENESIS: A PRACTICAL APPROACH, IRL Press (1991). The ability of cadaverine exporter polypeptide variants to export cadaverine can be determined using an HPLC Assay for extracellular cadaverine.

Preferred cadaverine exporter polypeptides according to the invention are the cadaverine exporter polypeptide from Corynebacterium glutamicum (dapE) and their equivalent genes, which have up to 80%, preferably 90% and most preferred 95% and 98% sequence identity (based on amino acid sequence) with the corresponding "original" gene product and have still the biological activity of a cadaverine exporter polypeptide. These equivalent genes can be easily constructed by introducing nucleotide substitutions, deletions or insertions by methods known in the art or by cloning homolog genes of other organisms, which can be identified and cloned according to methods well known in the art e.g. database searches, library screenings, complementation assays or enzymatic activity tests. Preferably the nucleotide sequence of cloned homolog genes is optimized for expression in the intended host microorganism e.g. by adapted to the codon usage of Corynebacterium glutamicum or Escherichia coli.

Sequences homologous to the sequence of SEQ ID NO: 1 can be found. Examples are given as the following: A4QH10_CORGB protein from Corynebacterium glutamicum strain R TX=40322 SEQ ID NO 25, Q8FMK8_COREF protein from Corynebacterium efficiens SEQ ID NO 26, ZP_03711358 protein from Corynebacterium matruchotii ATCC 33806 SEQ ID NO: 27, ZP_03392764 protein from Corynebacterium amycolatum SK46 SEQ ID NO: 28, YP_003696648 protein from Arcanobacterium haemolyticum DSM 20595 SEQ ID NO 29, ZP_06042915 protein from Corynebacterium aurimucosum ATCC 700975 SEQ ID NO 30, ZP_03936401 protein from Corynebacterium striatum ATCC 6940 SEQ ID NO 31, ZP_06837496 protein from Corynebacterium ammoniagenes DSM 20306 SEQ ID NO 32.

Accordingly, in a preferred embodiment the intracellular or the cadaverine exporter activity is at least partly, preferably to more than 30% or to more than 50% or to more than 60% or to more than 70% or to more than 75%, 80%, 85%, 90%, 95% 98%, 99% due to one or more polypeptides comprising an amino acid sequence being at least 80% or at least 85% or at least 90% or at least 95% or at least 98% identical to SEQ ID NO: 1 and having cadaverine exporter activity.

Other preferred embodiments of the invention use the cadaverine exporter polypeptide of Corynebacterium glutamicum (SEQ ID NO: 1) which may be retranslated into DNA by applying the codon usage of the microorganism intended to express the cadaverine exporter polypeptide e.g E. coli, or to optimize the codon usage for expression in Corynebacterium glutamicum.

A preferred microorganism of the invention comprises an intracellular lysine decarboxylase activity, preferably a high intracellular decarboxylase activity. An intracellular lysine decarboxylase activity can be created or enhanced by transforming the microorganism with one or more lysine decarboxylase genes to be expressed by the microorganism. Additionally or alternatively lysine decarboxylase genes can be mutated to enhance expression or the enzymatic activity of the encoded lysine decarboxylase.

In another embodiment, the intracellular lysine decarboxylase activity is combined with an extracellular lysine decarboxylase activity. A microorganism lacking either an intracellular or extracellular lysine decarboxylase activity may be transformed to express a lysine decarboxylase either intracellular or extracellular. Extracellular expression can be achieved by mutating a lysine decarboxylase gene in order to comprise signal sequences for extracellular expression, e.g. secretion signals or signals for molecular anchors, which are functional in the microorganism to be transformed. Examples for extracellular expression can be found in Choi and Lee Appl Microbiol Biotechnol 2004 64: 625-635, Current Opinion in Biotechnology 2005, 16:538-545, Trends in Biotechnology 2007 16 73-79.

In case the intracellular or extracellular lysine decarboxylase activity is due to expression of more than one lysine decarboxylase genes coding for different polypeptides having lysine decarboxylase activity, the total intracellular or extracellular lysine decarboxylase activity will be the result of those different lysine decarboxylase activities. The contribution of a particular lysine decarboxylase gene to the total lysine decarboxylase activity can be measured by comparing the expression level of different lysine decarboxylase genes in a particular microorganism and comparing the specific enzymatic activities of the lysine decarboxylases expressed from these genes. The expression level of different genes can be measured according to methods well known in the art, preferably the expression level is measured on the protein level, e.g. by Western Blots or ELISA assays. Methods to measure the specific enzymatic activity of a lysine decarboxylase are also well known in the art. A preferred method is disclosed in WO2007113127.

In case a endogenous lysine decarboxylase activity is enhanced by transgenic expression of at least one further polypeptide having lysine decarboxylase activity, the contribution of this or those additional polypeptides can be measured by comparing the total lysine decarboxylase activity of the transformed and untransformed microorganism.

In a preferred embodiment the intracellular or the extracellular decarboxylase activity or both activities are at least partly, preferably to more than 30% or to more than 50% or to more than 60% or to more than 70% or to more than 75%, 80%, 85%, 90%, 95% 98%, 99% due to one or more polypeptides comprising an amino acid sequence being at least 80% or at least 85% or at least 90% or at least 95% or at least 98% identical to SEQ ID NO: 3 and having lysine decarboxylase activity, preferably having a high lysine decarboxylase activity.

In one embodiment the intracellular or the extracellular decarboxylase activity or both activities are to more than 98% or to more than 99% due to one or more polypeptides comprising an amino acid sequence being at least 80% or at least 85% or at least 90% or at least 95% or at least 98% identical to SEQ ID NO: 3 and having lysine decarboxylase activity, preferably having a high lysine decarboxylase activity.

In one embodiment the intracellular or the extracellular decarboxylase activity or both activities are to more than 98% or to more than 99% due to one or more polypeptides comprising an amino acid sequence being at least 80% or at least 85% or at least 90% or at least 95% or at least 98% identical to SEQ ID NO: 4 and having lysine decarboxylase activity, preferably having a high lysine decarboxylase activity.

In one embodiment, the microorganisms comprising a cadaverine exporter activity does also comprise an enhanced lysine import capacity.

In improved lysine import capacity, can be achieved by any measure, which enhances the flow of lysine from the fermentation medium into the microorganism or by reducing the flow of lysine from microorganism to the fermentation medium.

Methods to determine the lysine export and import activity can be found in Bellmann, A, Vrljic, M, Patek, M, et al. MICROBIOLOGY-SGM 147 pp. 1765-1774, 2001, and in Burkovski, A, Kramer, R. APPLIED MICROBIOLOGY AND BIOTECHNOLOGY 58 pp. 265-274. 2002 and in references cited within.

For example, the lysine import capacity can be improved by reducing or eliminating lysine exporter activity or an enhancing lysine permease activity or an enhancing lysine/cadaverine antiporter activity or any combination thereof.

A lysine exporter activity can be due to any polypeptide, being able to transport lysine from the medium to the cell, e.g. lysine-exporter, -symporter or -antiporter polypeptides.

In case the microorganism has an extracellular lysine decarboxylase activity and a high lysine production capacity, it may be of advantage to enhance the lysine export capacity by taking measures contrary to the ones described for enhancing the lysine import capacity, e.g. by enhancing a certain gene expression instead of reducing the expression of a certain gene. Examples for microorganisms having a high lysine production capacity and a reduced or eliminated expression of a lysine exporter polypeptide, but lacking an extracellular lysine decarboxylase activity can be found in WO 97/23597 and WO2005073390, which disclose methods for enhanced production of amino acids by culturing microorganism having an enhanced expression or activity of amino acid export proteins and in U.S. Pat. No. 7,435,584, which discloses a method for enhanced production of L-lysine by culturing corynebacteria having a high expression of the lysE (lysine export carrier) gene.

In one embodiment of the invention the activity of at least one lysine exporter polypeptide is decreased, wherein the lysine exporter polypeptide comprises an amino acid sequence being at least 80% or at least 85% or at least 90% or at least 95% or at least 98% identical to SEQ ID NO: 5 and having lysine export activity or wherein the lysine exporter polypeptide comprises an amino acid sequence being at least 80% or at least 85% or at least 90% or at least 95% or at least 98% identical to SEQ ID NO: 5 and having lysine export activity, or wherein the activity of at least two lysine exporter polypeptides are decreased, at least one comprising an amino acid sequence being at least 80% or at least 85% or at least 90% or at least 95% or at least 98% identical to SEQ ID NO:5 and having lysine export activity and at least one comprising an amino acid sequence being at least 80% or at least 85% or at least 90% or at least 95% or at least 98% identical to SEQ ID NO: 5 and having lysine export activity.

The lysE gene has been described in the literature, Eggeling, L, Sahm, H JOURNAL OF BIOSCIENCE AND BIOENGINEERING 92, 3 201-213, Eggeling, L, Sahm, H ARCHIVES OF MICROBIOLOGY 180, 3 155-160 2003, see also the German patent application DE 95-01048222.

The YbjE gene product (SEQ ID NO: 6) and mutants thereof have been described, for example in WO2005073390.

The term "decreased activity" includes the expression of a gene product, e.g. of a cadaverine exporter polypeptide, or a lysine exporter polypeptide, at a lower level than expressed prior to manipulation of the microorganism or in a comparable microorganism which has not been manipulated, preferably the expression of a gene product is compared to a well known strain of a particular microorganism species, which is grown under the same conditions, e.g. in the case of Corynebacterium, the expression of a gene is preferably compared with the expression level in the strain ATCC13032. In case of E. coli, the expression of a gene is preferably compared with the expression level in the strain MG1665, deposited in the strain collection ATCC in the case of Saccharomyces cerevisiae, the expression level is compared to the strain W303 deposited in the strain collection ATCC. In one embodiment, the microorganism can be genetically manipulated (e.g., genetically engineered) to express a level of gene product at a lesser than that expressed prior to manipulation of the microorganism or in a comparable microorganism which has not been manipulated. Genetic manipulation can include, but is not limited to, altering or modifying regulatory sequences or sites associated with expression of a particular gene (e.g., by removing strong promoters, inducible promoters or multiple promoters), modifying the chromosomal location of a particular gene, altering nucleic acid sequences adjacent to a particular gene such as a ribosome binding site or transcription terminator, decreasing the copy number of a particular gene, modifying proteins (e.g., regulatory proteins, suppressors, enhancers, transcriptional activators and the like) involved in transcription of a particular gene and/or translation of a particular gene product, or any other conventional means of decreasing expression of a particular gene routine in the art (including but not limited to use of antisense nucleic acid molecules, or other methods to knock-out or block expression of the target protein). In particular the gene can be manipulated that one or more nucleotides are being deleted from the chromosome of the host organism. The decreased activity of the gene product e.g. of a lysine exporter polypeptide can also be obtained by introducing one or more gene mutations which lead to a decreased activity of the gene product. In addition the activity of a gene product can be also decreased by influencing regulatory proteins that are regulating the expression or activity of said gene product e.g. by influencing the transcription of the said gene. Examples are transcriptional repressors and transcriptional activators. For example lysE gene expression is negatively influenced by the lysG gene product. The sequence of the lysG gene (herein disclosed as SEQ ID NO: 7) and the LysG gene product (herein disclosed as SEQ ID NO: 8 can also be found under the following accession numbers: P94632, X96471

In another embodiment the lysine import capacity is enhanced by an enhanced lysine permease activity or by an enhanced lysine/cadaverine antiporter activity or a combination of both.

The lysine permease activity of a given microorganism can be enhanced for example by increasing the expression of one or more endogenous lysine permease genes for example as disclosed in SEQ ID NO: 9, or increasing the permease activity of lysine permease polypeptides for example as disclosed in SEQ ID NO: 10, e.g. by random mutagenesis of the microorganism or by transforming the microorganism with one or more lysine permease genes or by any combination thereof.

In one embodiment the lysine permease activity of the microorganism is enhanced, by recombinant expression of one or more lysine permease polypeptides comprising an amino acid sequence, which is at least 80% or at least 85% or at least 90% or at least 95% or at least 98% identical to SEQ ID NO: 10 and having lysine permeate activity, e.g. homologues or mutants having lysine permease activity. Methods to determine the lysine permease activity can be found in Bellmann, A, Vrljic, M, Patek, M, et al. MICRO- BIOLOGY-SGM 147 pp. 1765-1774 2001, and in Burkovski, A, Kramer, R APPLIED MICROBIOLOGY AND BIOTECHNOLOGY 58 pp. 265-274 2002, in Fujii, T, et al. as well as in BIOSCIENCE BIOTECHNOLOGY AND BIOCHEMISTRY 66, pp 1981-1984, 2002 and in references cited therein.)

Recombinant expression can be archived for example by transformation of one or more lysine permease genes, by providing endogenous lysine permease genes with a deregulated promoter having a higher expression activity or by reducing negative regulators of lysine permease gene expression or gene product activity.

In another embodiment the lysine import capacity is enhanced by an enhanced lysine/cadaverine antiporter activity. Lysine/cadaverine antiporter are proteins transporting lysine and cadaverine at the same time in different directions across the membrane of the cell. Enhanced lysine/cadaverine antiporter activity can be archived by increasing the expression of one or more endogenous lysine/cadaverine antiporter genes, by random mutation of the microorganism, transforming the microorganism with one or more lysine/cadaverine antiporter genes or by optimizing the lysine/cadaverine antiporter activity of lysine/cadaverine antiporter polypeptides e.g. for a preference of lysine import and cadaverine export, or by any combination thereof.

In one embodiment the lysine/cadaverine antiporter activity of a microorganism is enhanced by recombinant expression of one or more lysine/cadaverine antiporter polypeptides comprising an amino acid sequence, which is at least 80% or at least 85% or at least 90% or at least 95% or at least 98% identical to SEQ ID NO: 11 having lysine/cadaverine antiporter activity, e.g. homologues or mutants having lysine/cadaverine antiporter activity.

Recombinant expression can be archived for example by transformation of one or more lysine/cadaverine antiporter genes, by providing endogenous lysine/cadaverine antiporter genes with a deregulated promoter having a higher expression activity or by reducing negative regulators of lysine/cadaverine antiporter gene expression or gene product activity.

It is known that the import or export activity of the cadB gene product, herein disclosed as SEQ ID NO: 11, depends on the lysine and cadaverine concentrations in the cell and the fermentation medium. Therefore, the lysine import capacity of a certain microorganism expressing a functional cadB gene product can be improved by enhancing the lysine concentration in the fermentation medium, preventing a low pH-value of the fermentation medium or by inserting mutations, which promote the lysine import at a given lysine concentration or pH-value in the fermentation medium or by a combination thereof (Soksawatmaekhin W. et al.; Excretion and uptake of cadaverine by CadB and its physiological functions in *Escherichia coli*; Molecular Microbiology; 2004; volume 51, 5; pages 1401 to 1412).

Several mutations are described, which promote the lysine import of the *Escherichia coli* cadB gene product a given lysine concentration or pH-value in the fermentation medium (Soksawatmaekhin W. et al.; Identification of the Cadaverine Recognition Site on the Cadaverine-Lysine Antiporter CadB; The Journal of Biological Chemistry; 2006; volume 281, 39; pages 29213 to 29220). A person having skill in the art will be able to identify similar mutations in other cadB proteins, e.g. homologues or mutants of cadB.

Accordingly, in one embodiment the lysine/cadaverine antiporter polypeptides comprise an amino acid sequence, which is at least 80% or at least 85% or at least 90% or at least 95% or at least 98% identical to SEQ ID NO: 11 comprises one or more of the following mutations: C12S, W41 L, W43L, Y55L, Y57L, Y73L, Y73F, Y73W, Y89L, Y89F, Y89W, Y90L, Y90F, Y90W, Y107L, Y174L, C125S, D185N, E204Q, E204D, Y235L, Y235F, Y235W, W289L, D303N, D303E, Y310L, Y366L, Y368L, D372N, E377Q, E408Q, Y423L, Y423F and Y423W. The mutations mentioned above are named according to the amino acid sequence of the cadB gene product. A person skilled in the art will be able to transfer these mutations to other gene products, e.g. gene products being homologous of the cadB gene product, by using sequence comparison tools e.g. by using sequence alignments.

Preferably the lysine/cadaverine antiporter polypeptides comprising an amino acid sequence, which is at least 80% or at least 85% or at least 90% or at least 95% or at least 98% identical to SEQ ID NO: 11 comprises one or more of the following mutations: W41 L, W43L, Y57L, Y89L, Y107L, Y174L, D185N, E204Q, Y235L, W289L, D303N, Y366L, Y368L, D372N and E408Q.

More preferred the lysine/cadaverine antiporter polypeptide comprising an amino acid sequence, which is at least 80% or at least 85% or at least 90% or at least 95% or at least 98% identical to SEQ ID NO: 11 comprises one or more of the following mutations: W41L, W43L, Y57L, Y107L, Y174L, D185N, Y366L, Y368L and E408Q.

In a further embodiment the invention provides for a microorganism comprising an intracellular lysine decarboxylase activity and an enhanced lysine import activity or comprising an intracellular and an extracellular lysine decarboxylase activity or comprising an intracellular and an extracellular lysine decarboxylase activity and an enhanced lysine import activity and having a high lysine production capacity. A microorganism having a high lysine production capacity is able to enrich lysine e.g. inside the cell or in the surrounding medium, if the lysine is not further metabolized e.g. to cadaverine.

Preferably the microorganism having a high lysine production capacity has at least one deregulated gene selected from the group (i). The group (i) is a group of genes which play a key role in the biosynthesis of lysine and consists of the genes of aspartokinase, aspartatesemialdehyde dehydrogenase, dihydrodipicolinate synthase, dihydrodipicolinate reductase, tetrahydrodipicolinate succinylase, succinyl-amino-ketopimelate transaminase, succinyl-diamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase, homoserine dehydrogenase, phophoenolpyruvate carboxykinase, succinyl-CoA synthetase, methylmalonyl-CoA mutase, diamine-acteyltransferase.

At least one gene of the group (i) has to be deregulated according to the inventive process. Preferably more than one gene of group (i), e.g. two, three, four, five, six, seven, eight, nine, ten genes are deregulated in the microorganism according to the invention.

Preferred genes of the group (i) to be deregulate are: aspartokinase, aspartatesemialdehyde dehydrogenase, dihydrodipicolinate synthase, dihydrodipicolinate reductase, diaminopimelate dehydrogenase, diaminopimelate decarboxylase, pyruvate carboxylase, glucose-6-phosphate dehydrogenase, transketolase, transaldolase, 6-phosphogluconolactonase, fructose 1,6-biphosphatase, homoserine dehydrogenase, succinyl-CoA synthetase, diamineacyltransferase.

The genes and gene products of group (i) are known in the art. EP 1108790 discloses mutations in the genes of homoserinedehydrogenase and pyruvate carboxylase which have a beneficial effect on the productivity of recombinant *corynebacteria* in the production of lysine. WO 00/63388 discloses mutations in the gene of aspartokinase which have a beneficial effect on the productivity of recombinant *corynebacteria* in the production of lysine. EP 1108790 and WO 00/63388 are incorporated by reference with respect to the mutations in these genes described above.

In the table below for every gene/gene product possible ways of deregulation of the respective gene are mentioned. The literature and documents cited in the row "Deregulation" of the table are herewith incorporated by reference with respect to gene deregulation. The ways mentioned in the table are preferred embodiments of a deregulation of the respective gene.

phatase is an "up"-mutation which increases the gene activity e.g. by gene amplification using strong expression signals and/or point mutations which enhance the enzymatic activity.

A preferred way of deregulation of the genes of homoserine dehydrogenase, phophoenolpyruvate carboxykinase, succinyl-CoA synthetase, methylmalonyl-CoA mutase Acetyltransferase is a "down"-mutation which decreases the gene activity e.g. by gene deletion or disruption, using weak expression signals and/or point mutations which destroy or decrease the enzymatic activity.

If aspartokinase is deregulated as a member of gene (i) group at least a second gene (i) member—other than aspartokinase—has to be deregulated also.

It has been observed that a significant portion of the cadaverine produced in the microorganism according to the inventive process may become acetylated later on (WO 2007/113127). In order to block the acetylation reaction which is attributed to an N-acetylcadaverine-forming polypeptide, which is defined as an enzymatic active polypeptide

TABLE 1

| Enzyme (gene product) | Gene | Deregulation |
| --- | --- | --- |
| Aspartokinase | ask | Releasing feedback inhibition by point mutation (Eggeling et al., (eds.), Handbook of *Corynebacterium glutamicum*, pages 20.2.2 (CRC press, 2005)) and amplification) |
| Aspartatesemialdehyde dehydrogenase | asd | Amplification |
| Dihydrodipicolinate synthase | dapA | Amplification |
| Dihydrodipicolinate reductase | dapB | Amplification |
| Tetrahydrodipicolinate succinylase | dapD | Amplification |
| Succinyl-amino-ketopimelate transaminase | dapC | Amplification |
| Succinyl-diamino-pimelate desuccinylase | dapE | Amplification |
| Diaminopimelate dehydrogenase | ddh | Amplification |
| Diaminopimelate epimerase | dapF | Amplification |
| Arginyl-tRNA synthetase | argS | Amplification |
| Diaminopimelate decarboxylase | lysA | Amplification |
| Pyruvate carboxylase | pycA | Releasing feedback inhibition by point mutation (EP1108790) and amplification |
| Phosphoenolpyruvate carboxylase | ppc | Amplification |
| Glucose-6-phosphate dehydrogenase | G6PDH zwf | Releasing feedback inhibition by point mutation (US2003/0175911) and amplification |
| Transketolase | tkt | Amplification |
| Transaldolase | tal | Amplification |
| 6-Phosphogluconolactonase | pgl | Amplification |
| 6-Phosphogluconate dehydrogenase | | point mutation and amplification |
| Fructose 1,6-biphosphatase | fbp | Amplification |
| Homoserine dehydrogenase | hom | Attenuating by point mutation (EP1108790) decrease of gene activity, Knock-out or silencing by mutation |
| Phophoenolpyruvate carboxykinase | pck | Knock-out or silencing by mutation, decrease of gene activity or others |
| Succinyl-CoA synthetase | sucC | Attenuating by point mutation (WO 05/58945) decrease of gene activity silencing by mutation |
| Methylmalonyl-CoA mutase | MMCM | Attenuating by point mutation (WO 05/58945) decrease of gene activity, Knock-out or silencing by mutation |
| Diamine Acetyltransferase | RXA2240 | Weakening by decrease of gene activity, Knock-out or silencing by mutation, deletion |

A preferred way of deregulation of the genes of aspartokinase, aspartatesemialdehyde dehydrogenase, dihydrodipicolinate synthase, dihydrodipicolinate reductase, tetrahydrodipicolinate succinylase, succinyl-amino-ketopimelate transaminase, succinyl-diamino-pimelate desucdiaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase is an "up"-mutation which increases the gene activity e.g. by gene amplification using strong expression signals and/or point mutations which enhance the enzymatic activity.

being able to produce N-acetylcadaverine. In order to increase the yield of cadaverine it is a preferred embodiment of the invention to deregulate the diamine acetyltransferase of the producing microorganism, especially to decrease its activity, e.g by deletion or disruption of the gene.

One example for an N-acetylcadaverine-forming polypeptide is the acetyl-CoA dependent diamine acetyltransferase of *Corynebacterium glutamicum* (NP_600742 protein) for example as disclosed in SEQ ID NO: 12 and SEQ ID NO: 13

In one embodiment of the invention, the N-acetylcadaverine-forming activity is decreased by decreasing the activity of at least one N-acetylcadaverine-forming polypeptide comprising an amino acid sequence, being at least 80%, or at least 85%, or at least 90%, or at least 95%, or at least 98% identical to SEQ ID NO: 13 and has N-acetylcadaverine-forming activity. N-actylcadaverine-forming activity can be tested as described in WO 2007/113127.

It has been observed that a significant portion of the cadaverine produced in the microorganism according to the inventive process may be converted to aminopropylcadaverine by an aminopropylcadaverine-forming polypeptide. In order to block this reaction and in order to increase the yield of cadaverine it is a preferred embodiment of the invention to deregulate the aminopropylcadaverine-forming polypeptide of the producing microorganism, especially to decrease its activity, e.g. by deletion or disruption of the gene.

One example for an aminopropylcadaverine-forming polypeptide is the spermidine synthase of *Escherichia coli*, as described in Soksawatmaekhin W. et al; Molecular Microbiology; (2004) Vol. 51, 5; pages 1401 to 1412)), SEQ ID NO: 14

Accordingly, in one embodiment of the invention, the aminopropylcadaverine-forming activity is decreased by decreasing the activity of at least one aminopropylcadaverine-forming polypeptide comprising an amino acid sequence, being at least 80%, or at least 85%, or at least 90%, or at least 95%, or at least 98% identical to SEQ ID NO: 14.

It has been observed that the production capacity of a microorganism for lysine can be improved by deregulating the activity of a homoserine dehydrogenase polypeptide of the cadaverine producing microorganism as described in JP2004222569, preferably by decreasing its activity via deletion or disruption of the gene coding for the homoserine dehydrogenase polypeptide.

One example of a homoserine dehydrogenase polypeptide is the homoserine dehydrogenase of *Corynebacterium glutamicum*, herein disclosed as SEQ ID NO: 15, or homoserine dehydrogenases of *Escherichia coli*, herein disclosed as SEQ ID NO: 16 and SEQ ID NO: 17.

Accordingly, in one embodiment of the invention, the homoserine dehydrogenase activity is decreased by decreasing the activity of a homoserine dehydrogenase polypeptide comprising an amino acid sequence, being at least 80%, or at least 85%, or at least 90%, or at least 95%, or at least 98% identical to SEQ ID NO: 15, 16 or 17.

Methods for the determination of homoserine dehydrogenase activity can be found in. M. B. Jenkins, V. W. Woodward, Biochimica et Biophysica Acta, 1970, 212, 21-32.

In another embodiment of the invention the microorganism has a reduced capacity to degrade lysine other than by decarboxylation, e.g. by having a decreased lysine hydroxylase activity.

A lysine hydroxylase polypeptide is a polypeptide having lysine hydroxylase activity also described as lysine N6-hydroxylase [EC:1.14.13.59]. Tests for having lysine hydroxylase activity can be found in Meneely K M, and Lamb A L BIOCHEMISTRY 46 Pages: 11930-11937 2007 and in I J, Hsueh L C, Baldwin J E, et al. EUROPEAN JOURNAL OF BIOCHEMISTRY 268 Pages: 6625-6636.

One example is the lysine hydroxylase iucD of *Escherichia coli* CFT073 (SEQ ID NO: 18).

In a further embodiment of the invention, the lysine degradation activity is decreased by decreasing the activity of at least one polypeptide comprising an amino acid sequence being at least 80%, or at least 85%, or at least 90%, or at least 95%, or at least 98% identical to SEQ ID NO: 18 lysine hydroxylase, having lysine hydroxylase activity.

In a further embodiment of the invention, the microorganism has a deregulated spermidine forming or uptake activity or putrescine forming or uptake activity or a combination thereof.

A spermidine forming activity is brought about by a polypeptide being able to synthesize spermidine. One example for a spermidine forming polypeptide is the spermidine synthase of SEQ ID NO: 14.

A putrescine forming activity is brought about by a polypeptide being able to synthesize putrescine. One example for a putrescine forming polypeptide are the putrescine synthase of *E. coli* speE (e.g. as disclosed in SEQ ID NO: 19) or the ornithin decarboxylases of *E. coli*, speF (e.g as disclosed in SEQ ID NO: 20)

A polypeptide having spermidine or putrescine uptake activity is a polypeptide being able to transport spermidine or putrescine or both into the cell. One example for an spermidine and or an putrescine uptake polypeptide is potE of *E. coli* (e.g as disclosed in SEQ ID NO: 21), which functions as a putrescine/ornithine antiporter.

In one embodiment of the invention, the microorganism has a decreased spermidine forming or uptake activity or putrescine forming or uptake activity, wherein
a) the spermidine forming activity is deregulated by decreasing the activity of a spermidine forming polypeptide comprising an amino acid sequence being at least 80%, or at least 85%, or at least 90%, or at least 95%, or at least 98% identical to SEQ ID NO: 14 or,
b) the putrescine forming activity is deregulated by decreasing the activity of a putrescine forming polypeptide comprising an amino acid sequence being at least 80%, or at least 85%, or at least 90%, or at least 95%, or at least 98% identical to SEQ ID NO: 19, or
c) the putrescine forming activity is deregulated by decreasing the activity of a ornithine decarboxylase polypeptide comprising an amino acid sequence being at least 80%, or at least 85%, or at least 90%, or at least 95%, or at least 98% identical to SEQ ID NO: 20, or
d) the spermidine or putrescine or spermidine and putrescine uptake activity is deregulated by decreasing the activity of a spermidine or putrescine or spermidine and putrescine uptake polypeptide comprising an amino acid sequence being at least 80%, or at least 85%, or at least 90%, or at least 95%, or at least 98% identical to SEQ ID NO: 21 or
e) wherein the spermidine forming or uptake activity or the putrescine forming or uptake activity or a combination thereof is decreased by decreasing the activity of a combination of a), b), c) or d).

An important aspect of the present invention involves cultivating or culturing the recombinant microorganisms described herein, such that the desired compound cadaverine is produced.

Accordingly one embodiment of the invention is a cadaverine production system comprising a microorganism, comprising an intracellular lysine decarboxylase activity and an enhanced lysine import activity or comprising an intracellular and an extracellular lysine decarboxylase activity or comprising an intracellular and an extracellular lysine decarboxylase activity and an enhanced lysine import activity and a fermentation medium suitable to cultivate this microorganism, preferably the fermentation medium comprises lysine.

A cadaverine production system is a technical system for the production of cadaverine, e.g. a culture medium comprising a cadaverine producing microorganism or a lysine comprising solution or culture medium and a lysine decarboxylase producing microorganism. Usually the cadaverine production system comprises technical systems to support the production of cadaverine, e.g. a fermenter.

The term "cultivating" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured on solid media or semi-solid media. In a preferred embodiment, a microorganism of the invention is cultured in media (e.g., a sterile, liquid media) comprising nutrients essential or beneficial to the maintenance and/or growth of the microorganism.

Carbon sources which may be used include sugars and carbohydrates, such as for example glucose, sucrose, lactose, fructose, maltose, molasses, starch and cellulose, oils and fats, such as for example soy oil, sunflower oil, peanut oil and coconut oil, fatty acids, such as for example palmitic acid, stearic acid and linoleic acid, alcohols, such as for example glycerol and ethanol, and organic acids, such as for example acetic acid. In one preferred embodiment, glucose, fructose or sucrose are used as carbon sources. These substances may be used individually or as a mixture.

In another preferred embodiment, the microorganisms described herein are cultivated in or on liquid, solid or semi-solid media comprising xylose, arabinose, cellobiose or mixtures thereof, such media may or may not comprise other carbon sources like the ones described above. Media for cultivating microorganisms of the invention can comprise only a limited number of different carbon sources e.g. 1, 2, 3, 4, 5 or more carbon sources, or might comprise very complex mixtures of carbon sources, hydrolysates of lignocellulose substrates or agricultural residues, e.g. hydrolysates of starches from sources such as but not limited to corn, wheat, rye, barley, rice, cassava, or hydrolysates of straw, wood, paper, or other material of plant origin. Preferred combinations of carbon sources are media comprising a high content of glucose and xylose, fructose and xylose, sucrose and xylose, or sucrose and glucose, or sucrose and fructose, or sucrose, glucose and fructose and sucrose, glucose, fructose and xylose, or glucose, fructose and xylose or glucose, fructose, xylose and arabinose or sucrose, xylose and arabinose, or glucose, xylose and arabinose and of other combination of sugars mentioned.

In case the media comprises xylose it is of advantage to use a microorganism of the invention expressing or overexpressing genes of the xylose metabolism.

Genes of the xylose metabolism are for example the genes of the xylABFGHR locus of *E. coli*, comprising genes for a xylose transport systems (xylE, xylT and the xylFGH gene), genes for xylose utilization (xylA and xylB gene) and genes for xylose transcriptional activator (xylR gene). Microorganisms overexpressing genes of the xylABFGHR locus are described in EP1577396 and EP1577369. *Corynebacteria* overexpressing genes of the xylA alone or with the xylB gene of *E. coli*, encoding a xylose isomerase and xylB encoding a xylulokinase have been described e.g. (Kawaguchi, et al. Engineering of a xylose metabolic pathway in *Corynebacterium gutamicum*, Applied and Environmental Microbiology, 2006, Vol. 72, 5, pages 3418 to 3428).

In a preferred embodiment, the microorganism of the invention expresses or over expresses at least the xylA or the xylB gene or even more preferred the xylA and the xylB gene.

In case the media comprises arabinose, it is of advantage to use a microorganism of the invention expressing or overexpressing genes of the arabinose metabolism. Genes of the arabinose metabolism are for example genes of the araBAD operons, e.g. the araA, araB, araD and araE genes of *E. coli*, coding for L-arabinose isomerase (araA), L-ribolokinase (araB) and L-ribulose-5-phosphate-4-epimerase (araD) or the genes of the araBDA operon of *Corynebacterium gluctamicum*, comprising homologs of the araA, araB and araD genes and the araE coding for a L-arabinose isomerase, the araR gene coding for a transcriptional regulator and the galM gene coding for a putative aldose 1-epimerase. Preferably the microorganism of the invention expresses or overexpresses at least the araA, araB and araD gene, more preferably at least the araA, araB, araD and the araE gene. Kawaguchi et al. Identification and Functional Analysis of the Gene Cluster for L-Arabinose Utilization in *Corynebacterium glutamicum*, Applied and Environmental Microbiology, 2009, 75, Vol. 11, pages 3419-3429).

The *E. coli* homologs of the genes of the arabinose metabolism can also be used in heterologous microorganism such as *Corynebacterium glutamicum* (Kawaguchi et al. Engineering of an L-arabinose metabolic pathway in *Corynebacterium glutamicum*, Applied Microbiology and Biotechnology, 2008, 77, Vol, 5, pages 1053 to 1062).

In case the media comprises cellobiose, it is of advantage to use a microorganism of the invention expressing or overexpressing genes of the cellobiose metabolism. Genes of the cellobiose metabolism are for example the bglA genes of *Corynebacterium glutamicum*, encoding phosphenolpyruvate:carbohydratephosphotransferase system (PTS) beta-glucoside-specific enzyme IIBCA component and phosphor-beta-glucosidase examples of these genes and the respective proteins from the *Corynebacterium* R strain can be found under the accession number AF508972.

In case the media comprises combinations of xylose, arabinose, cellobiose or other carbon sources, it is of advantage to use microorganisms of the invention expressing or overexpressing genes of the xylose metabolism, arabinose metabolism or cellobiose metabolism. For example, in case the media has a high content of xylose- and arabinose it is of advantage to use microorganisms expressing or overexpressing genes of the xylose- and arabinose metabolism for example expressing the xylA and xylB genes and the araA, araB, araD genes, preferably the xylA and xylB araA, araB, araD and araE gene.

In case the media has a high content xylose and cellubiose it is of advantage to use microorganisms expressing or overexpressing genes of the xylose- and cellobiose metabolism for example expressing the xylA and xylB and the bglA genes (Sasaki et al. Simultaneous utilization of D-cellobiose, D-glucose, and D-xylose by recombinant *Corynebacterium glutamicum* under oxygen-deprived conditions, Applied Microbiology and Biotechnology, 2008, Vol. 81, 4, pages 691 to 699)

Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium must furthermore contain metal salts, such as for example magnesium sulfate or iron sulfate, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during cultivation.

Preferably, microorganisms of the present invention are cultured under controlled pH. The term "controlled pH" includes any pH which results in production of the desired fine chemical, e.g. cadaverine. In one embodiment, microorganisms are cultured at a pH of about 7. In another embodiment, microorganisms are cultured at a pH of between 6.0 and 8.5. The desired pH may be maintained by any number of methods known to those skilled in the art. For example, basic compounds such as sodium hydroxide, potassium hydroxide, ammonia, or ammonia water, or acidic compounds, such as phosphoric acid or sulfuric acid, are used to appropriately control the pH of the culture.

Also preferably, microorganisms of the present invention are cultured under controlled aeration. The term "controlled aeration" includes sufficient aeration (e.g., oxygen) to result in production of the desired fine chemical, e.g., cadaverine. In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermenter) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents such as fatty acid polyglycol esters).

Moreover, microorganisms of the present invention can be cultured under controlled temperatures. The term "controlled temperature" includes any temperature which results in production of the desired fine chemical, e.g., cadaverine. In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermenter (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation medium is added continuously to a fermenter and an equal amount of used or "conditioned" medium is simultaneously removed, preferably for recovery of the desired cadaverine. A variety of such processes have been developed and are well-known in the art.

The methodology of the present invention can further include a step of recovering cadaverine. The term "recovering" cadaverine includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example cadaverine can be recovered from culture media by first removing the microorganisms. The broth removed biomass is then passed through or over a cation exchange resin to remove unwanted cations and then through or over an anion exchange resin to remove unwanted inorganic anions and organic acids having stronger acidities than cadaverine. In addition the broth can be treated with caustic agents and the cadaverine be extracted with organic solvents such as alkohols by phase separation. The cadaverine can be retrieved from the extracted phase by distillation to purity sufficient for diverse applications. Possible applications include the production of polyamides by polycondensation with dicarboxylic organic acids.

Accordingly, in another aspect, the present invention provides a process for the production of polyamides (e.g. Nylon™) comprising a step as mentioned above for the production of cadaverine. The cadaverine is reacted in a known manner with di-, tri- or polycarboxylic acids to get polyamides. Preferably the cadaverine is reacted with dicarboxylic acids containing 4 to 10 carbons such as succinic acid, glutaric acid, adipic acid, pimelic acid, suberic acid, azelaic acid, sebacic acid, and so forth. The dicarboxylic acid is preferably a free acid.

The microorganism of the invention are useful for producing cadaverine by fermenting these microorganism, which is growing the microorganism in culture, preferably growing the microorganism under culture conditions as described above.

Accordingly the invention includes a process for the production of cadaverine, comprising fermenting a microorganism, comprising an intracellular lysine decarboxylase activity and an enhanced lysine import activity or comprising an intracellular and an extracellular lysine decarboxylase activity or comprising an intracellular and an extracellular lysine decarboxylase activity and an enhanced lysine import activity. Preferably the process includes recovering of cadaverine from the culture medium.

In one embodiment the microorganism comprises an enhanced lysine/cadaverine antiporter activity, e.g. a microorganism overexpressing a polypeptide which is at least 80% or at least 85% or at least 90% or at least 95% or at least 98% identical to SEQ ID NO: 11 and having lysine/cadaverine antiporter activity, e.g. homologues or mutants having lysine/cadaverine antiporter activity and the process includes fermenting the microorganism in a medium comprising lysine. Preferably the culture medium comprises more than 0.1 mM, or more than 0.5 mM, or more than 1 mM or more than 3 mM, or more than 5 mM, or more than 7 mM, or more than 8 mM, or more than 9 mM, or more than 10 mM lysine. More preferred the culture medium comprises more than 15 mM lysine. Even more preferred, the culture medium comprises more than 20 mM lysine. Most preferred the culture medium comprises more than 30 mM lysine In a further embodiment the microorganism comprises an extracellular lysine decarboxylase activity or comprises an extracellular lysine decarboxylase activity and an enhanced lysine/cadaverine antiporter activity.

In another embodiment of the invention is a process to produce cadaverine, wherein the concentration (mol/l) of cadaverine in the culture medium is at least 1.2 times higher, or more than 1.3 times higher, or more than 1.4 times, or more than 1.5 times, or more than 1.6 times, or more than 1.7 times, or more than 1.8 times, or more than 1.9 times or more than 2 times, 3 times, 4 times, 5 times, 6 times, 7 times, 8 times, 9 times higher than the concentration (mol/l) of N-acetylcadaverine or aminopropylcadaverine or of both. Another embodiment of the invention is the culture medium produced in the process.

The cadaverine produced by the processes described above can be recovered or purified by a work up of the cadaverine (DAP) comprising fermentation broth, i.e. the culture medium in its state after the process to produce cadaverine is finished or has been terminated.

The process to recover or purify the cadaverine from the fermentation broth as described in the following medium is solely for exemplary reasons. The person skilled in the art will know alternative methods or variants of the process described below, which can also successfully be applied.

In order to recover the produced cadaverine, it is of advantage to thicken or to concentrate the fermentation broth. The fermentation broth can be thickened or concentrated by known methods, such as, for example, with the aid of a rotary evaporator, thin-film evaporator, falling film evaporator, by reverse osmosis or by nanofiltration. If necessary, salts which may have precipitated due to the concentration procedure may be removed, for example by filtration or centrifugation. This concentrated fermentation broth can then be worked up in the manner of the invention to obtain cadaverine. For the work up in accordance with the present invention, such a concentration procedure is feasible, but not absolutely necessary.

According to the invention, cadaverine is extracted from the fermentation broth with the aid of an organic extractant. More specifically, use is made of an organic solvent having a miscibility gap with water that is as polar as possible and stable at alkaline pH, such as in particular a polar, dipolar protic, organic solvent. Suitable solvents are in particular cyclic or open-chain, optionally branched alkanols having from 3 to 8 carbon atoms, in particular n- and iso-propanol, n-, sec- and iso-butanol, or cyclohexanol, and also n-pentanol, n-hexanol-n-heptanol, n-octanol, 2-octanol and the mono- or polybranched isomeric forms thereof. Particular mention is to be made here of n-butanol.

In a preferred embodiment, the extraction and/or subsequent phase separation are carried out batchwise at an elevated temperature which is limited by the boiling points of water and of the extractant or of possibly forming azeotropes. Using the extractant n-butanol, extraction and phase separation could be carried out, for example, at about 25-90° C. or, preferably, at 40-70° C. For extraction, the two phases are stirred until the partition equilibrium has been established, for example over a period of from 10 seconds to 2 hours, preferably 5 to 15 min. The phases are then left to settle until they have separated completely; this takes preferably from 10 seconds to 5 hours, for example 15 to 120 or 30 to 90 minutes, in particular also at a temperature in the range from about 25-90° C. or 40-70° C. in the case of n-butanol.

In further preferred embodiments, cadaverine is extracted from the fermentation broth continuously in a multi-stage process (for example in mixer-settler combinations) or continuously in an extraction column.

The skilled working may establish the configuration of the extraction columns which can be employed according to the invention for the phases to be separated in each case as part of optimization routines. Suitable extraction columns are in principle those without power input or those with power input, for example pulsed columns or columns with rotating internals. The skilled worker may also, as part of routine work, select in a suitable manner types and materials of internals, such as sieve trays, and column trays, to optimize phase separation. The basic theories of liquid-liquid extraction of small molecules are well known (cf. e.g. H.-J. Rehm and G. Reed, Eds., (1993), Biotechnology, Volume 3 Bioprocessing, Chapter 21, VCH, Weinheim). The configuration of industrially applicable extraction columns is described, for example, in Lo et al., Eds., (1983) Handbook of Solvent Extraction, JohnWiley& Sons, New York. Explicit reference is made to the disclosure of the textbooks above.

After phase separation, cadaverine is isolated and purified from the cadaverine-comprising extract phase in a manner known per se. Possible measures of recovering cadaverine are in particular, without being limited thereto, distillation, precipitation as salt with suitable organic or inorganic acids, or combinations of such suitable measures.

Distillation may be carried out continuously or batchwise. A single distillation column or a plurality of distillation columns coupled to one another may be used. Configuring the distillation column apparatus and establishing the operational parameters are the responsibilities of the skilled worker. The distillation columns used in each case may be designed in a manner known per se (see e.g. Sattler, Thermische Trennverfahren [Thermal separation methods], 2nd Edition 1995, Weinheim, p. 135ff; Perry's Chemical Engineers Handbook, 7th Edition 1997, New York, Section 13). Thus, the distillation columns used may comprise separation-effective internals, such as separation trays, e.g. perforated trays, bubble-cap trays or valve trays, arranged packings, e.g. sheet-metal or fabric packings, or random beds of packings. The number of plates required in the column(s) used and the reflux ratio are essentially governed by the purity requirements and the relative boiling position of the liquids to be separated, with the skilled worker being able to ascertain the specific design and operating data by known methods.

Precipitation as salt may be achieved by adding suitable organic or inorganic acids, for example sulfuric acid, hydrochloric acid, phosphoric acid, acetic acid, formic acid, carbonic acid, oxalic acid, etc. In another preferred embodiment, an organic dicarboxylic acid is used, forming a salt which can be used, either directly or after purification, for example by recrystallization, in a subsequent polycondensation to give the polyamide. More specifically, such dicarboxylic acids are $C_4$-$C_{12}$-dicarboxylic acids.

The organic cadaverine phase produced in the extraction procedure may also be worked up chromatographically. For chromatography, the cadaverine phase is applied to a suitable resin, for example a strongly or weakly acidic ion exchanger (such as Lewatit 1468 S, Dowex Marathan C, Amberlyst 119 Wet or others), with the desired product or the contaminants being partially or fully retained on the chromatographic resin. These chromatographic steps may be repeated, if necessary, using the same or other chromatographic resins. The skilled worker is familiar with selecting the appropriate chromatographic resins and their most effective application. The purified product may be concentrated by filtration or ultrafiltration and stored at an appropriate temperature.

The identity and purity of the compound(s) isolated may be determined by prior art technologies. These comprise high performance liquid chromatography (HPLC), gas chromatography (GC), spectroscopic methods, staining methods, thin layer chromatography, NIRS, enzyme assay or microbiological assays. These analytical methods are summarized in: Patek et al. (1994) Appl, Environ. Microbiol. 60:133-140; Malakhova et al. (1996) Biotekhnologiya 11 27-32; and Schmidt et al. (1998) Bioprocess Engineer. 19:67-70. Ullmann's Encyclopedia of Industrial Chemistry (1996) Vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Vol. 17.

As the cadaverine produced and recovered or purified by the processes described above can be used to produce polyamides by known techniques, those polyamides represent another embodiment of the invention.

The invention will now be described in more detail on the basis of the following non-limiting examples and with reference to the accompanying figures

EXAMPLES

Strains and Plasmids.

The diaminopentane-producer *Corynebacterium glutamicum* DAP-3c has been rationally derived from *C. glutamicum* 11424 by codon optimized expression of lysine decarboxylase (Kind, S., Jeong, W. K., Schröder, H. and Wittmann, C. (Kind et al., 2010a) "Systems-wide metabolic pathway engineering in *Corynebacterium glutamicum* for bio-based production of diaminopentane." Metab Eng.; and Kind, S., Jeong, W. K., Schröder, H., Zelder, O. and Wittmann, C. (Kind et al. 2010b). "Identification and elimination of the competing N-acetyl-diaminopentane pathway for improved production of diaminopentane by *Corynebacterium glutamicum*." Appl Environ Microbiol 76(15), 5175-80.). Both strains were used in the present work. For strain construction, the *Escherichia coli* strains DH5α and NM522 (invitrogen, Karlsruhe, Germany) and the plasmids pTc and pClik int sacB were applied as described previously (Kind et al., 2010a).

Medium.

The first pre-culture was grown in complex medium (Kind et al., 2010a). For the second pre-culture and the subsequent main culture a minimal medium was applied (Becker, J., Klopprogge, C. and Wittmann, C. (2008) (Becker et al., 2008). "Metabolic responses to pyruvate kinase deletion in lysine producing *Corynebacterium glutamicum*." Microb Cell Fact 7, 8.).

Cultivation.

All cultivations were performed at 30° C. and 230 rpm on a rotary shaker (shaking diameter 5 cm, Multitron, Infors AG, Bottmingen, Switzerland). For the first pre-culture, single colonies were used as inoculum. After an incubation for about 8 h, the cells were harvested by centrifugation (8800×g, 2 min, 4° C.), washed twice with sterile 5% NaCl solution and then used as inoculum for the second pre-cultivation (50 mL in 500 mL baffled flasks). The cells were harvested in the exponential growth phase under the same conditions as described above and used as inoculum for the main cultures which were performed in triplicate (50 mL in 500 mL baffled flasks). During the cultivations, the pH remained constant at 7.0±0.2.

Chemicals.

Tryptone, beef extract, yeast extract and agar were obtained from Difco Laboratories (Detroit, USA). All other chemicals were of analytical grade and obtained from Aldrich (Steinheim, Germany), Merck (Darmstadt, Germany) or Fluka (Buchs, Switzerland).

Genetic Engineering of *C. glutamicum*.

The construction, the purification and the analysis of plasmid DNA and the transformation of *E. coli* and *C. glutamicum* were performed as described previously (Kind et al., 2010a). The targeted deletion of genes and the exchange of native *C. glutamicum* promoters were carried out as described recently (Bolten, C. J., Schr, H., Dickschat, J. and Wittmann, C. (2010) (Bolten et al., 2010). "Towards methionine overproduction in *Corynebacterium glutamicum*—methanethiol and dimethyldisulfide as reduced sulfur sources." J Microbiol Biotechnol 20(8), 1196-203; Dickschat, J. S., Wickel, S., Bolten, C. J., Nawrath, T., Schulz, S. and Wittmann, C. (2010) (Dickschat et. 2010). "Pyrazine Biosynthesis in *Corynebacterium glutamicum*." European Journal of Organic Chemistry 2010(14), 2687-2695. al.), Shortly, genes were deleted by replacement of the coding region by a shortened gene fragment. For genome-based amplification of expression, the native promoter of the corresponding was replaced by the strong promoter of the sod gene (NCg12826) (Becker, J., Klopprogge, C., Herold, A., Zelder, O., Bolten, C. J. and Wittmann, C. (2007) (Becker et al., 2007). "Metabolic flux engineering of L-lysine production in *Corynebacterium glutamicum*—overexpression and modification of G6P dehydrogenase." J Biotechnol.) For this purpose, the integrative plasmid pClik int sacB, which cannot replicate in *C. glutamicum*, was used (Becker, J., Klopprogge, C., Zelder, O., Heinzle, E. and Wittmann, C. (2005) (Becker et al., 2005). "Amplified Expression of Fructose 1,6-bisphosphatase in *Corynebacterium glutamicum* increases in vivo flux through the pentose phosphate pathway and lysine production on different carbon sources." Appl Environ Microbiol 71(12), 8587-8596; The plasmid pClik 5a MCS, which replicates in *C. glutamicum*, was utilized for plasmid-based over-expression of genes in combination with the promoter of the tuf gene (NCgl0480) (Kind et al., 2010a)). The genetic modifications were verified by PCR. The primers used for construction and verification of the genetic changes are listed in Table 2.

TABLE 2

Wild-type and derived mutant gene, corresponding modification and site-specific sequences of primers used for the construction (1-4/6) and the verification (1, 4/6) of allelic replacement in the mutant strains of C. glutamicum by PCR.

| Wild-type gene, mutant gene | Modification | Primer Sequences |
|---|---|---|
| Cg2893, cg2893 | Deletion | cg2893-1: 5'-GATCGGATCCTTTCTGATCGGIGTAGACAA-3'<br>cg2893-2: 5'-CAAACCATCAGTATGAGTCGTCATCCTCAAACGTAATGC-3'<br>cg2893-3: 5'-GCATTACGTTTGAGGATGACGACTCATACTGATGGTTTG-3'<br>cg2893-4: 5'-GATCCTCGAGTACTAGGGCAATGATCAACA-3' |
| lysE, · lysE | Deletion | lysE-1: 5'-GATCACTAGTGCAGCAAGGATAATGTGTGC-3'<br>lysE-2: 5'-CACGACGACGTTGATCCAGCGGTCCGATGGACAGTAAAAG-3'<br>lysE-3: 5'-CTTTTACTGTCCATCGGACCGCTGGATCAACGTCGTCGTG-3'<br>lysE-4: 5'-GATCTCTAGAGCTGCCAACAATGGTCTTGG-3' |
| Cg2893, $P_{sod}2893$ | Replacement of the native promoter by the sod promotor | $P_{sod}2893$-1: 5'-GATCCTCGAGTAATTGTTCTGCGTAGCTGT-3'<br>$P_{sod}2893$-2: 5'-CCCGGAATAATTGGCAGCTAGGATCGTAACTGTAACGAAT-3'<br>$P_{sod}2893$-3: 5'-ATTCGTTACAGTTACGATCCTAGCTGCCAATTATTCCGGG-3'<br>$P_{sod}2893$-4: 5'-TGTAAGGTTTCTGAAGTCATGGGTAAAAAATCCTTTCGTA-3'<br>$P_{sod}2893$-5: 5'-TACGAAAGGATTTTTTACCCATGACTTCAGAAACCTTACA-3'<br>$P_{sod}2893$-6: 5'-GATCGGATCCGTTAATGAGGAAAACCGAAC-3' |
| Cg2893, $P_{tuf}2893$ | Replacement of the native promoter by the tuf promotor | $P_{tuf}2893$-1: 5'-GATCCTCGAGTGGCCGTTACCCTGCGAATG-3'<br>$P_{tuf}2893$-2: 5'-TGTAAGGTTTCTGAAGTCATTGTATGTCCTCCTGGACTTC-3'<br>$P_{tuf}2893$-3: 5'-GAAGTCCAGGAGGACATACAATGACTTCAGAAACCTTACA-3'<br>$P_{tuf}2893$-4: 5'-CTAGCCTAGGCTAGTGCGCATTATTGGCTCCCTT-3' |

Analysis of Substrates and Products.

The concentration of glucose was quantified in 1:10 diluted cultivation supernatants by a glucose analyzer (2300 STAT Plus, Yellow Springs Instrument, Ohio). Trehalose and organic acids were quantified in 1:10 diluted culture supernatants by HPLC (LaChrom Elite, VWR Hitachi, West Chester, Pa., USA), employing an Aminex HPX-87H column (300×7.8 mm; Bio-Rad, Hercules, Calif., USA) as stationary phase and 12.5 mM $H_2SO_4$ as mobile phase at 0.5 mL min$^{-1}$ and 40° C. The detection was performed using UV light at 220 nm (organic acids) and refractive index (trehalose), respectively. The determination of the cell concentration as optical density at 660 nm and as cell dry mass was performed as described previously (Kiefer, P., Heinzle, E., Zelder, O. and Wittmann, C. (2004) (Kiefer et al., 2004). "Comparative metabolic flux analysis of lysine-producing Corynebacterium glutamicum cultured on glucose or fructose." Appl Environ Microbiol 70(1), 229-39.). Amino acid quantification in culture supernatants (1:10 diluted) and cell extract was carried out by HPLC (Krömer, J. O., Fritz, M., Heinzle, E. and Wittmann, C. (2005). (Krömer et al., 2005) "In vivo quantification of intracellular amino acids and intermediates of the methionine pathway in Corynebacterium glutamicum."). The same method was adapted by a modified elution gradient to the quantification of biological polyamines, including 1,5-diaminopentane and N-acetyl-1,5-diaminopentane (Kind et al., 2010a).

Intracellular Metabolite Analysis.

Intracellular metabolite sampling was performed via fast filtration and extraction in boiling water (Wittmann, C., Kromer, J. O., Kiefer, P., Binz, T. and Heinzle, E. (2004) (Wittmann et al., 2004). "Impact of the cold shock phenomenon on quantification of intracellular metabolites in bacteria." Anal Biochem 327(1), 135-9; Bolten et al., 2007). This included a washing step of the cells on the filter with 15 ml 5% NaCl solution, matching the ionic strength of the cultivation medium to avoid metabolite leakage (Bolten et al., 2007).

RNA Extraction and Gene Expression Analysis.

Total RNA extraction from exponentially growing cells was performed as described previously (Kind et al., 2010b). For comparative gene expression analysis, a custom DNA microarray was designed from the C. glutamicum genome NC_306958 using the online software Agilent eArray. Design of the oligonucleotide probes for the genes of interest, fluorescence labelling, hybridization, scanning and data processing were carried out as described by Kind et al. (2010b). The custom DNA microarray used in these experiments contained 14363 probes with up to five replicates for each of the 3057 open reading frames.

Lysine Decarboxylase Activity.

The activity of lysine decarboxylase was determined in crude cell extract. The preparation of the cell extract, the determination of the protein concentration and the measurement of lysine decarboxylase activity was performed as described previously (Kind et al., 2010a). For the experiments on enzyme kinetics, diaminopentane was added to the reaction mixture to a final concentration of 10, 15, 20, 30 and 35 mmol L$^{-1}$, respectively.

Kinetic Properties of Lysine Decarboxylase Expressed in C. glutamicum.

A first important study unraveled the general relevance of the product export as potential bottleneck for production. It focussed on the kinetic properties of lysine decarboxylase, especially on the aspect of inhibition by its end-product, diaminopentane. For this purpose, crude cell extract was obtained during exponential growth of C. glutamicum DAP 3-c and assayed for lysine decarboxylase activity expressed in this diaminopentane-producer. The specific in vitro activity of lysine decarboxylase was 97.0±3.5 mmol g$^{-1}$h$^{-1}$. This is almost hundredfold higher than the specific in vivo product flux of 1.07±0.02 mmol g$^{-1}$ h$^{-1}$, determined from the accumulation of diaminopentane and N-acetyl diaminopentane in the culture medium. Obviously, only a small fraction of the available catalytic power of lysine decarboxylase was recruited for product formation.

In order to analyse to which extent this involved end-product inhibition of the enzyme, its specific activity was additionally determined at varied concentrations of diaminopentane. Clearly, the specific lysine decarboxylase activity strongly decreased with increasing concentration of diaminopentane (FIG. 1). The relevance of this inhibition was then assessed by quantification of the corresponding intracellular diaminopentane level in the production strain. Using an appropriate fast filtration approach with complete removal of the surrounding medium the intracellular pool size of diaminopentane determined from three biological replicates was 20.3±1.6 mM. Under these conditions, the LdcC activity in vitro is reduced by about 40% (FIG. 1). This suggested that the terminal step of the biosynthetic pathway is significantly inhibited in vivo by the elevated intracellular product level and revealed the relevance of product export as valuable metabolic engineering target. An active transport process, involving one or several so far unknown export proteins appeared likely, due to the chemical properties of diaminopentane at cytoplasmic neutral pH, i.e. its high positive charge.

Identification of Potential Candidates for Diaminopentane Export.

For identification of potentially encoding genes, genome-wide transcription profiling was carried out. For this purpose, the global gene expression pattern was compared between the diaminopentane-producing strain C. glutamicum DAP-3c and its parent strain C. glutamicum 11424 which produces lysine, but not diaminopentane. For the analysis, RNA was extracted from cells, harvested during the exponential growth phase, i.e. at an optical density of 3. RNA for the reference was obtained from four biological replicates and for DAP-3c from seven biological replicates, respectively. Reference RNA was pooled before labelling and competitive hybridization to a genome-wide micro array.

Among the 3000 genes analysed and statistically treated, about 35 genes exhibited a statistically significant up-regulation in the diaminopentane producer (Table 2). These belonged to different functional categories and, most interestingly, included different transporters. Out of the up-regulated transporters, four could be attributed to iron and sugar transport and therefore were not related to the function of interest.

Seven genes, belonging to five operons, however, represented so far uncharacterized transport systems. They displayed potential candidates for diaminopentane export. The relevant transporters comprised an ABC transporter (cg2181 and cg2184) and a permease (cg2893) and its regulator (cg2894). Moreover the transport regulator AsnC family regulatory protein (cg2942), a regulator of a LysE type translocator (cg2941), was up-regulated. Among all candidates the highest expression increase was found for the permease (Table 3). This gene belongs to a superfamily of facilitators and was chosen as first candidate to be tested for the export of diaminopentane. It should be mentioned, that the expression of the lysine exporter lysE was reduced about 3.8-fold. In addition to the above mentioned genes, five genes encoded for proteins with so far unknown function.

TABLE 3

Comparative transcriptome analysis of lysine producing C. glutamicum 11424 and di-aminopentane producing C. glutamicum DAP-3c. The data, originating from at least four biological replicates for each strain, are given as ratio of expression of strain 11424 versus strain DAP-3c and comprise the significantly up-regulated genes. The cut-off considered for a significantly different expression ratio was taken as 1.7. Genes functionally linked to transport are highlighted in bold.

| Name | Fold change | Description | Function |
|---|---|---|---|
| YP_224856.1 | 1.8 | DNA-directed RNA polymerase alpha subunit | transcription |
| YP_224855.1 | 1.9 | 30S ribosomal protein S4 | translation |
| YP_224833.1 | 1.9 | 50S ribosomal protein L18 | |
| YP_224793.1 | 1.8 | 30S ribosomal protein S12 | |
| YP_224806.1 | 1.8 | 50S ribosomal protein L2 | |
| YP_224795.1 | 1.7 | elongation factor G | |
| YP_227230.1 | 1.7 | 50S ribosomal protein L9 | |
| YP_226853.1 | 2.3 | TetR family regulatory protein | regulators |
| YP_227034.1 | 2.3 | transcriptional regulator MERR family | |
| YP_226897.1 | 2.1 | AsnC family regulatory protein | |
| YP_226846.1 | 3.2 | dithiobiotin synthetase | anabolism |
| YP_224548.2 | 2.4 | 2-isopropylmalate synthase | |
| YP_225282.1 | 2.1 | phospho-2-dehydro-3-deoxyheptonate aldolase | |
| YP_226831.1 | 1.8 | phosphoribosylformylglycinamidine synthase subunit PurS | |
| YP_227246.1 | 1.7 | myo-inositol-1-phosphate synthase | |
| YP_225870.1 | 1.9 | triosephosphate isomerase | carbon metabolism |
| YP_226490.1 | 1.8 | pyruvate dehydrogenase subunit E1 | |
| YP_224671.1 | 1.7 | succinate dehydrogenase A | |
| YP_227126.1 | 2.1 | flavin-containing monooxygenase (FMO) | stress |
| YP_227166.1 | 1.9 | manganese superoxide dismutase | response |
| YP_224936.1 | 2.1 | NAD-dependent deacetylase | unknown |
| YP_224429.1 | 2.0 | probable transmembrane protein | |
| YP_226704.1 | 1.9 | hypothetical protein | |
| YP_224523.1 | 1.8 | putative oxidoreductase protein | |
| YP_225935.1 | 1.7 | putative secreted protein | |
| YP_227210.1 | 1.7 | probable two component sensor kinase | |
| YP_226852.1 | 2.6 | major facilitator superfamily permease | transporter |
| YP_225102.1 | 2.2 | ABC-type cobalamin/Fe3+-siderophores transport system | |
| YP_226232.1 | 1.9 | ABC-type peptide transport system, secreted component | |
| YP_226616.1 | 1.8 | putative secreted or membrane protein | |
| YP_226705.1 | 1.8 | ABC-type sugar transport system, ATPase component | |

TABLE 3-continued

Comparative transcriptome analysis of lysine producing *C. glutamicum* 11424 and di-
aminopentane producing *C. glutamicum* DAP-3c. The data, originating from at least four biological
replicates for each strain, are given as ratio of expression of strain 11424 versus strain
DAP-3c and comprise the significantly up-regulated genes. The cut-off considered for a significantly
different expression ratio was taken as 1.7. Genes functionally linked to transport are
highlighted in bold.

| Name | Fold change | Description | Function |
|---|---|---|---|
| YP_225125.1 | 1.7 | Na+/proline, Na+/panthothenate symporter or related permease | |
| YP_225645.1 | 1.7 | glucose-specific enzyme II BC component of PTS | |
| YP_225848.1 | 1.7 | iron-regulated ABC-type transporter | |
| YP_226235.1 | 1.7 | peptide ABC transporter ATPase | |

Targeted Deletion of the Putative Diaminopentane Exporter cg2893.

The gene, encoding the major facilitator superfamily permease, cg2893, was deleted first as potential candidate. For this purpose, a recombinant plasmid, allowing marker-free replacement of the target gene by a shortened fragment, lacking 659 by of the coding region, was constructed. Clones from the second recombination were validated for the desired deletion by site specific PCR using the primers cg2893-1 and cg2893-4 (Table 1). A positive clone was identified by a shortened PCR product of 670 bp, clearly differing from the fragment length of 1329 bp, resulting for the wild type. The deletion mutant, lacking the permease was compared with the parent strain. The study included cultivation in minimal medium on glucose, followed by subsequent analysis of the product spectrum in the broth. The strain lacking the permease revealed a substantially reduced diaminopentane secretion (FIG. 2, Table 4). The reduction of the diaminopentane yield from 200 mmol (mol$^{-1}$ glucose) to 32 mmol (mol$^{-1}$ glucose) corresponded to a 84% decrease. Obviously, the permease cg2893 displayed the main exporter for diaminopentane in *C. glutamicum*. Based on its functional role, it was annotated as diaminopentane exporter dapE. Interestingly, the effect of the dapE deletion on the export of N-acetyl-diaminopentane was rather different. In the designated *C. glutamicum*•dapE, the acetylated variant of the product was still significantly exported (FIG. 2, Table 3). This underlines that the identified export protein is rather specific for diaminopentane, but not for N-acetyl diaminopentane. As in the parent strain, lysine secretion was negligible. It should be noticed that the diaminopentane export was not entirely disabled by deletion of the permease. This indicates that this enzyme is the major, but not the exclusive export system.

Functional Role of the Lysine Exporter LysE for Diaminopentane Export.

*C. glutamicum* $_{delta}$dapE, lacking the major diaminopentane exporter, still exhibited secretion of diaminopentane into the medium. This indicated the presence of another diaminopentane export protein. Due to the structural similarity of diaminopentane and its precursor lysine, the lysine exporter LysE was additionally checked as possible candidate. The encoding gene lysE was deleted in *C. glutamicum* $_{delta}$dapE. Growth and production characteristics of the double deletion mutant *C. glutamicum* $_{delta}$dapE $_{delta}$lysE in minimal medium, however, revealed no significant difference compared to its parent strain (Table 4). This indicates that LysE is not involved in the export of diaminopentane.

Metabolic Engineering of Diaminopentane Production by Amplification of dapE.

The novel exporter dapE emerged as promising metabolic engineering target to increase diaminopentane production. It was amplified in the best producing strain *C. glutamicum* DAP-3c. This was realized by genome-based over-expression. For this purpose the natural dapE promoter was replaced by the strong promoter of the superoxide dismutase (sod). A plasmid that allowed the marker-free integration of the sod promoter directly in front of the start codon of dapE was constructed using the primers R$_{sod}$2893-1 to P$_{sod}$2893-6 (Table 3). Positive clones, carrying the sod promoter between the upstream sequence of the gene and the start codon, were validated by PCR on the basis of a 200 bp extended PCR fragment as compared to the wild type. The obtained mutant was designated as *C. glutamicum* P$_{sod}$dapE.

FIG. 2 shows the impact of the engineered export. Overall, the amplification of dapE resulted in a significantly enhanced product secretion. It 20% increased of the diaminopentane yield to 240 mmol (mol glucose)$^{-1}$ in P$_{sod}$dapE compared to DAP-3c (Table 3). The specific production rate (q$_{DAP}$) was even enhanced by 40% to 1.1 mmol g$^{-1}$ h$^{-1}$. As beneficial side effect, the formation of N-acetyl-diaminopentane was reduced by more than 75%, indicating that the undesirable acetylation of the product is decreased by an optimized export. In addition the exporter mutant showed a higher viability which was reflected by a higher specific growth rate (0.30 compared to 0.25 h$^{-1}$) and a high

TABLE 4

Growth and production characteristics of diaminopentane producing *C. glutamicum*
DAP-3c, $_{delta}$dapE and $_{delta}$dapE $_{delta}$lysE in minimal medium with glucose as
sole carbon source.

| Strain | μh$^{-1}$ | Y$_{Dap/S}$ mmol mol$^{-1}$ | Y$_{N-Ace-Dap/S}$ mmol mol$^{-1}$ | Y$_{Lys/S}$ mmol mol$^{-1}$ | Y$_{X/S}$ g mol$^{-1}$ |
|---|---|---|---|---|---|
| DAP-3c | 0.25 ± 0.00 | 200 ± 5 | 52 ± 3 | 2 ± 0 | 64.2 ± 0.8 |
| $_{delta}$dapE | 0.29 ± 0.01 | 32 ± 1 | 39 ± 1 | <0.1 | 73.7 ± 1.1 |
| $_{delta}$dapE $_{delta}$lysE | 0.27 ± 0.01 | 24 ± 1 | 44 ± 2 | <0.1 | 74.3 ± 1.3 | specific glucose uptake rare (4.5 as compared to 4.2 mmol $g^{-1}$ $h^{-1}$) (FIG. 2, Table 4). The biomass yield was rather similar in both strains. The same also holds for other by-products. Trehalose, lactate, glycine, alanine, glutamate and α-ketoglutarate occurred all at rather low amount, but were not affected. Overall, the engineered mutant with increased expression of dapE showed a remarkable improvement of key production properties. It should be mentioned that plasmid-based overexpression of dapE under control of the tuf promoter, additionally tested, resulted in a substantially retarded cell growth (μ=0.18 $h^{-1}$) and a slightly reduced diaminopentane yield ($Y_{Dap/S}$=192 mmol (mol glucose)$^{-1}$).

The gene sequence and the polypeptide sequence of dapE is disclosed below:

dapE Gene Sequence:

```
atgacttcagaaaccttacaggcgcaagcgcctacgaaaacccaacgtt-
gggctttcctcgccgttatcagcggtggtctctttctgatcggtgtagacaactcgattctc-
tacaccgcactccctctgctgcgtgaacagctcgcagccaccgaaacccaagcgttgtg-
gatcatcaacgcatatcccctgctcatggcgggccttcttttgggtaccggcacttt-
gggtgacaaaatcggcaaccgccggatgttcctcatgggcttgagcatttcg-
gaatcgcttcacttggtgctgcgtttgctccaactgcgtgggctcttgttgctgcga-
gagcttccttggcatcggtgcggcaacgatgatgcctgcaaccttggctctgatccg-
cattacgtttgaggatgagcgtgagcgcaacactgcaattggtatttggggttccgtgg-
caattcttggcgctgcggcaggcccgatcattggtggtgcgctgtt-
ggaattcttctggtggggttcggttttcctcattaacgttccggtggctgttatcgcgtt-
gatcgctacgcttttgtggcgccgccaatatcgcgaatccgtctaagcattgggat-
ttcttgtcgtcgttctatgcgctgctcacacttgctgggttgatcatcac-
gatcaaggaatctgtgaatactgcacgccatatgcctcttcttttgggtgcagtcatcatgtt-
gatcattggtgcggtgttgtttagcagtcgtcagaagaagatcgaggagccacttcta-
gatctgtcgttgttccgtaatcgccttttcttaggcggtgtggttgctgcggg-
catggcgatgtttactgtgtccggtttggaaatgactacctcgcagcgtttccagtt-
gtctgtgggtttcactccacttgaggctggtttgctcatgatcccagctgcattggg-
tagcttcccgatgtctattatcggtggtgcaaacctgcatcgttggggcttcaaac-
cgctgatcagtggtggttttgctgccactgccgttggcatcgccctgtgtattt-
ggggcgcgactcatactgatggtttgccgttttcatcgcgggtc-
tattcttcatgggcgcgggtgctggttcggtaatgtctgtgtcttccactgcgat-
tatcggttccgcgccggtgcgtaaggctggcatggcgtcgtcgatcgaa-
gaggtctcttatgagttcggcacgctgttgtctgtcgcgattttgggtagctt-
gttcccattcttctactcgctgcatgccccggcagaggttgcgga-
taacttctcggcgggtgttcaccacgcgattgatggcgatcggcgcgtgcatctttt-
ggacaccgcatacattaacgtgttgatcattgccctagtatgcgcag-
tagcggctgctctgatcagcagttaccttttccgcggaaatccgaagggagccaataatgcgcactag
``` dapE Protein Sequence:

```
MTSETLQAQAPTKTQRWAFLAVISGGLFLIGVDNSILYTALPLLREQLAATETQAL-
WIINAYPLLMAGLLLGTGTLGDKIGHRRMFLMGLSIFGIASLGAAFAPTAWALVAARAFLGI-
GAATMMPATLALIRITFEDERERNTAIGIWGSVAILGAAAGPIIGGALLE-
FFWWGSVFLINVPVAVIALIATLFVAPANIANPSKHWDFLSSFYALLTLAG-
LIITIKESVNTARHMPLLLGAVIMLIIGAVLFSSRQKKIEEPLLDLSLFRN-
RLFLGGVVAAGMAMFTVSGLEMTTSQRFQLSVGFTPLEAGLLMIPAALGSFPMSI-
```

-continued

```
IGGANLHRWGFKPLISGGFAATAVGIALCIWGATHTDGLPFFIAGLFF-

MGAGAGSVMSVSSTAIIGSAPVRKAGMASSIEEVSYEFGTLLSVAILGSLFPFFYSLHAPAE-

VADNFSAGVHHAIDGDAARASLDTAYINVLIIALVCAVAAALISSYLFRGNPKGANNAH
```

The invention claimed is:

1. A microorganism comprising a deregulated cadaverine exporter activity, wherein the deregulated cadaverine exporter activity is at least partially due to deregulation of at least one cadaverine exporter polypeptide comprising an amino acid sequence being 90% to 99% identical to SEQ ID NO: 1, wherein at least one gene encoding the cadaverine exporter polypeptide is overexpressed, and wherein the microorganism is a *Corynebacterium glutamicum* and the deregulated cadaverine exporter activity is in comparison to cadaverine exporter activity in *Corynebacterium glutamicum* ATCC 13032.

2. A microorganism as claimed in claim 1, wherein the cadaverine exporter activity is increased in comparison to cadaverine exporter activity in *Corynebacterium glutamicum* ATCC 13032.

3. A process for the production of cadaverine, comprising fermenting a microorganism as claimed in claim 1.

* * * * *

SEQUENCE LISTING

<160> NUMBER OF SEQ ID NOS: 50

<210> SEQ ID NO 1
<211> LENGTH: 494
<212> TYPE: PRT
<213> ORGANISM: Corynebacterium glutamicum

<400> SEQUENCE: 1

```
Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320
```

```
Phe Pro Met Ser Ile Ile Gly Gly Ala Asn Leu His Arg Trp Gly Phe
            325                 330                 335

Lys Pro Leu Ile Ser Gly Gly Phe Ala Ala Thr Ala Val Gly Ile Ala
        340                 345                 350

Leu Cys Ile Trp Gly Ala Thr His Thr Asp Gly Leu Pro Phe Phe Ile
    355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490
```

<210> SEQ ID NO 2
<211> LENGTH: 1485
<212> TYPE: DNA
<213> ORGANISM: Corynebacterium glutamicum

<400> SEQUENCE: 2

```
atgacttcag aaaccttaca ggcgcaagcg cctacgaaaa cccaacgttg ggctttcctc        60
gccgttatca gcgtggtctc tttctgatc ggtgtagaca actcgattct ctacaccgca       120
ctccctctgc tgcgtgaaca gctcgcagcc accgaaaccc aagcgttgtg atcatcaac       180 gcatatcccc tgctcatggc gggccttctt ttgggtaccg cactttggg tgacaaaatc       240 ggccaccgcc ggatgttcct catgggcttg agcattttcg gaatcgcttc acttggtgct       300
gcgtttgctc caactgcgtg gctcttgtt gctgcgagag ctttccttgg catcggtgcg       360
gcaacgatga tgcctgcaac cttggctctg atccgcatta cgtttgagga tgagcgtgag       420
cgcaacactg caattggtat tggggttcc gtggcaattc ttggcgctgc ggcaggcccg       480
atcattggtg gtgcgctgtt ggaattcttc tggtggggtt cggttttcct cattaacgtt       540
ccggtggctg ttatcgcgtt gatcgctacg cttttgtgg cgccggccaa tatcgcgaat       600
ccgtctaagc attgggattt cttgtcgtcg ttctatgcgc tgctcacact tgctgggttg       660
atcatcacga tcaaggaatc tgtgaatact gcacgccata tgcctcttct tttgggtgca       720
gtcatcatgt tgatcattgg tgcggtgttg tttagcagtc gtcagaagaa gatcgaggag       780
ccacttctag atctgtcgtt gttccgtaat cgcctttcct taggcggtgt ggttgctgcg       840
ggcatggcga tgtttactgt gtccggtttg gaaatgacta cctcgcagcg tttccagttg       900
tctgtgggtt tcactccact tgaggctggt tgctcatga tcccagctgc attgggtagc       960
ttcccgatgt ctattatcgg tggtgcaaac ctgcatcgtt ggggcttcaa accgctgatc      1020
agtggtggtt tgctgccac tgccgttggc atcgccctgt gtatttgggg cgcgactcat      1080
actgatggtt tgccgttttt catcgcgggt ctattcttca tgggcgcggg tgctggttcg      1140
```

-continued

```
gtaatgtctg tgtcttccac tgcgattatc ggttccgcgc cggtgcgtaa ggctggcatg    1200
gcgtcgtcga tcgaagaggt ctcttatgag ttcggcacgc tgttgtctgt cgcgattttg    1260
ggtagcttgt tcccattctt ctactcgctg catgccccgg cagaggttgc ggataacttc    1320
tcggcgggtg ttcaccacgc gattgatggc gatgcggcgc gtgcatcttt ggacaccgca    1380
tacattaacg tgttgatcat tgccctagta tgcgcagtag cggctgctct gatcagcagt    1440
taccttttcc gcggaaatcc gaagggagcc aataatgcgc actag                    1485
```

<210> SEQ ID NO 3
<211> LENGTH: 713
<212> TYPE: PRT
<213> ORGANISM: Escherichia coli

<400> SEQUENCE: 3

```
Met Asn Ile Ile Ala Ile Met Gly Pro His Gly Val Phe Tyr Lys Asp
  1               5                  10                  15

Glu Pro Ile Lys Glu Leu Glu Ser Ala Leu Val Ala Gln Gly Phe Gln
             20                  25                  30

Ile Ile Trp Pro Gln Asn Ser Val Asp Leu Leu Lys Phe Ile Glu His
         35                  40                  45

Asn Pro Arg Ile Cys Gly Val Ile Phe Asp Trp Asp Glu Tyr Ser Leu
     50                  55                  60

Asp Leu Cys Ser Asp Ile Asn Gln Leu Asn Glu Tyr Leu Pro Leu Tyr
 65                  70                  75                  80

Ala Phe Ile Asn Thr His Ser Thr Met Asp Val Ser Val Gln Asp Met
                 85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
    290                 295                 300

Asn Ser Thr Tyr Asp Gly Leu Leu Tyr Asn Thr Asp Trp Ile Lys Gln
305                 310                 315                 320
```

-continued

```
Thr Leu Asp Val Pro Ser Ile His Phe Asp Ser Ala Trp Val Pro Tyr
                325                 330                 335
Thr His Phe His Pro Ile Tyr Gln Gly Lys Ser Gly Met Ser Gly Glu
            340                 345                 350
Arg Val Ala Gly Lys Val Ile Phe Glu Thr Gln Ser Thr His Lys Met
        355                 360                 365
Leu Ala Ala Leu Ser Gln Ala Ser Leu Ile His Ile Lys Gly Glu Tyr
    370                 375                 380
Asp Glu Glu Ala Phe Asn Glu Ala Phe Met Met His Thr Thr Thr Ser
385                 390                 395                 400
Pro Ser Tyr Pro Ile Val Ala Ser Val Glu Thr Ala Ala Ala Met Leu
                405                 410                 415
Arg Gly Asn Pro Gly Lys Arg Leu Ile Asn Arg Ser Val Glu Arg Ala
            420                 425                 430
Leu His Phe Arg Lys Glu Val Gln Arg Leu Arg Glu Glu Ser Asp Gly
        435                 440                 445
Trp Phe Phe Asp Ile Trp Gln Pro Pro Gln Val Asp Glu Ala Glu Cys
    450                 455                 460
Trp Pro Val Ala Pro Gly Glu Gln Trp His Gly Phe Asn Asp Ala Asp
465                 470                 475                 480
Ala Asp His Met Phe Leu Asp Pro Val Lys Val Thr Ile Leu Thr Pro
                485                 490                 495
Gly Met Asp Glu Gln Gly Asn Met Ser Glu Glu Gly Ile Pro Ala Ala
            500                 505                 510
Leu Val Ala Lys Phe Leu Asp Glu Arg Gly Ile Val Val Glu Lys Thr
        515                 520                 525
Gly Pro Tyr Asn Leu Leu Phe Leu Phe Ser Ile Gly Ile Asp Lys Thr
    530                 535                 540
Lys Ala Met Gly Leu Leu Arg Gly Leu Thr Glu Phe Lys Arg Ser Tyr
545                 550                 555                 560
Asp Leu Asn Leu Arg Ile Lys Asn Met Leu Pro Asp Leu Tyr Ala Glu
                565                 570                 575
Asp Pro Asp Phe Tyr Arg Asn Met Arg Ile Gln Asp Leu Ala Gln Gly
            580                 585                 590
Ile His Lys Leu Ile Arg Lys His Asp Leu Pro Gly Leu Met Leu Arg
        595                 600                 605
Ala Phe Asp Thr Leu Pro Glu Met Ile Met Thr Pro His Gln Ala Trp
    610                 615                 620
Gln Arg Gln Ile Lys Gly Glu Val Glu Thr Ile Ala Leu Glu Gln Leu
625                 630                 635                 640
Val Gly Arg Val Ser Ala Asn Met Ile Leu Pro Tyr Pro Pro Gly Val
                645                 650                 655
Pro Leu Leu Met Pro Gly Glu Met Leu Thr Lys Glu Ser Arg Thr Val
            660                 665                 670
Leu Asp Phe Leu Leu Met Leu Cys Ser Val Gly Gln His Tyr Pro Gly
        675                 680                 685
Phe Glu Thr Asp Ile His Gly Ala Lys Gln Asp Glu Asp Gly Val Tyr
    690                 695                 700
Arg Val Arg Val Leu Lys Met Ala Gly
705                 710

<210> SEQ ID NO 4
<211> LENGTH: 715
```

<212> TYPE: PRT
<213> ORGANISM: Escherichia coli

<400> SEQUENCE: 4

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400
```

```
Pro His Tyr Gly Ile Val Ala Ser Thr Glu Thr Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
            595                 600                 605

Ala Phe Glu Val Leu Pro Thr Met Val Met Thr Pro Tyr Ala Ala Phe
            610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
            690                 695                 700

Thr Val Lys Val Leu Lys Glu Glu Ser Lys Lys
705                 710                 715

<210> SEQ ID NO 5
<211> LENGTH: 233
<212> TYPE: PRT
<213> ORGANISM: Corynebacterium glutamicum

<400> SEQUENCE: 5

Met Glu Ile Phe Ile Thr Gly Leu Leu Leu Gly Ala Ser Leu Leu Leu
1               5                   10                  15

Ser Ile Gly Pro Gln Asn Val Leu Ile Lys Gln Gly Ile Lys Arg
            20                  25                  30

Glu Gly Leu Ile Ala Val Leu Leu Val Cys Leu Ile Ser Asp Val Phe
        35                  40                  45

Leu Phe Ile Ala Gly Thr Leu Gly Val Asp Leu Leu Ser Asn Ala Ala
```

```
                50                  55                  60
Pro Ile Val Leu Asp Ile Met Arg Trp Gly Gly Ile Ala Tyr Leu Leu
65                  70                  75                  80

Trp Phe Ala Val Met Ala Ala Lys Asp Ala Met Thr Asn Lys Val Glu
                85                  90                  95

Ala Pro Gln Ile Ile Glu Glu Thr Glu Pro Thr Val Pro Asp Asp Thr
            100                 105                 110

Pro Leu Gly Gly Ser Ala Val Ala Thr Asp Thr Arg Asn Arg Val Arg
        115                 120                 125

Val Glu Val Ser Val Asp Lys Gln Arg Val Trp Val Lys Pro Met Leu
130                 135                 140

Met Ala Ile Val Leu Thr Trp Leu Asn Pro Asn Ala Tyr Leu Asp Ala
145                 150                 155                 160

Phe Val Phe Ile Gly Gly Val Gly Ala Gln Tyr Gly Asp Thr Gly Arg
                165                 170                 175

Trp Ile Phe Ala Ala Gly Ala Phe Ala Ala Ser Leu Ile Trp Phe Pro
            180                 185                 190

Leu Val Gly Phe Gly Ala Ala Ala Leu Ser Arg Pro Leu Ser Ser Pro
        195                 200                 205

Lys Val Trp Arg Trp Ile Asn Val Val Ala Val Val Met Thr Ala
210                 215                 220

Leu Ala Ile Lys Leu Met Leu Met Gly
225                 230
```

<210> SEQ ID NO 6
<211> LENGTH: 299
<212> TYPE: PRT
<213> ORGANISM: Escherichia coli

<400> SEQUENCE: 6

```
Met Phe Ser Gly Leu Leu Ile Ile Leu Val Pro Leu Ile Val Gly Tyr
1               5                   10                  15

Leu Ile Pro Leu Arg Gln Gln Ala Ala Leu Lys Val Ile Asn Gln Leu
                20                  25                  30

Leu Ser Trp Met Val Tyr Leu Ile Leu Phe Phe Met Gly Ile Ser Leu
            35                  40                  45

Ala Phe Leu Asp Asn Leu Ala Ser Asn Leu Leu Ala Ile Leu His Tyr
        50                  55                  60

Ser Ala Val Ser Ile Thr Val Ile Leu Leu Cys Asn Ile Ala Ala Leu
65                  70                  75                  80

Met Trp Leu Glu Arg Gly Leu Pro Trp Arg Asn His Gln Gln Glu
                85                  90                  95

Lys Leu Pro Ser Arg Ile Ala Met Ala Leu Glu Ser Lys Leu Cys
            100                 105                 110

Gly Val Val Ile Gly Phe Ala Ile Gly Leu Ser Gly Leu Ala Phe
        115                 120                 125

Leu Gln His Ala Thr Glu Ala Ser Glu Tyr Thr Leu Ile Leu Leu Leu
130                 135                 140

Phe Leu Val Gly Ile Gln Leu Arg Asn Asn Gly Met Thr Leu Lys Gln
145                 150                 155                 160

Ile Val Leu Asn Arg Arg Gly Met Ile Val Ala Val Val Val Val
                165                 170                 175

Ser Ser Leu Ile Gly Gly Leu Ile Asn Ala Phe Ile Leu Asp Leu Pro
            180                 185                 190
```

```
Ile Asn Thr Ala Leu Ala Met Ala Ser Gly Phe Gly Trp Tyr Ser Leu
            195                 200                 205

Ser Gly Ile Leu Leu Thr Glu Ser Phe Gly Pro Val Ile Gly Ser Ala
        210                 215                 220

Ala Phe Phe Asn Asp Leu Ala Arg Glu Leu Ile Ala Ile Met Leu Ile
225                 230                 235                 240

Pro Gly Leu Ile Arg Arg Ser Arg Ser Thr Ala Leu Gly Leu Cys Gly
                245                 250                 255

Ala Thr Ser Met Asp Phe Thr Leu Pro Val Leu Gln Arg Thr Gly Gly
            260                 265                 270

Leu Asp Met Val Pro Ala Ala Ile Val His Gly Phe Ile Leu Ser Leu
        275                 280                 285

Leu Val Pro Ile Leu Ile Ala Phe Phe Ser Ala
        290                 295

<210> SEQ ID NO 7
<211> LENGTH: 873
<212> TYPE: DNA
<213> ORGANISM: Corynebacterium glutamicum

<400> SEQUENCE: 7
atgaacccca ttcaactgga cactttgctc tcaatcattg atgaaggcag cttcgaaggc      60
gcctccttag ccctttccat ttccccctcg gcggtgagtc agcgcgttaa agctctcgag     120
catcacgtgg gtcgagtgtt ggtatcgcgc acccaaccgg ccaaagcaac cgaagcgggt     180
gaagtccttg tgcaagcagc gcggaaaatg tgttgctgc aagcagaaac taaagcgcaa      240
ctatctggac gccttgctga atcccgttta accatcgcca tcaacgcaga ttcgctatcc     300
acatggtttc ctcccgtgtt caacgaggta gcttcttggg gtggagcaac gctcacgctg     360
cgcttggaag atgaagcgca cacattatcc ttgctgcggc gtggagatgt tttaggagcg     420
gtaacccgtg aagctaatcc cgtggcggga tgtgaagtag tagaacttgg aaccatgcgc     480
cacttggcca ttgcaacccc ctcattgcgg gatgcctaca tggttgatgg gaaactagat     540
tgggctgcga tgcccgtctt acgcttcggt cccaaagatg tgcttcaaga ccgtgacctg     600
gacgggcgcg tcgatggtcc tgtggggcgc aggcgcgtat ccattgtccc gtcggcggaa     660 ggtttttggtg aggcaattcg ccgaggcctt ggttggggac ttcttcccga aacccaagct     720
gctcccatgc taaaagcagg agaagtgatc ctcctcgatg agatacccat tgacacaccg     780
atgtattggc aacgatggcg cctggaatct agatctctag ctagactcac agacgccgtc     840
gttgatgcag caatcgaggg attgcggcct tag                                 873

<210> SEQ ID NO 8
<211> LENGTH: 290
<212> TYPE: PRT
<213> ORGANISM: Corynebacterium glutamicum

<400> SEQUENCE: 8

Met Asn Pro Ile Gln Leu Asp Thr Leu Leu Ser Ile Ile Asp Glu Gly
1               5                   10                  15

Ser Phe Glu Gly Ala Ser Leu Ala Leu Ser Ile Ser Pro Ser Ala Val
            20                  25                  30

Ser Gln Arg Val Lys Ala Leu Glu His His Val Gly Arg Val Leu Val
        35                  40                  45

Ser Arg Thr Gln Pro Ala Lys Ala Thr Glu Ala Gly Glu Val Leu Val
    50                  55                  60
```

Gln Ala Ala Arg Lys Met Val Leu Leu Gln Ala Glu Thr Lys Ala Gln
65                  70                  75                  80

Leu Ser Gly Arg Leu Ala Glu Ile Pro Leu Thr Ile Ala Ile Asn Ala
            85                  90                  95

Asp Ser Leu Ser Thr Trp Phe Pro Pro Val Phe Asn Glu Val Ala Ser
            100                 105                 110

Trp Gly Gly Ala Thr Leu Thr Leu Arg Leu Glu Asp Glu Ala His Thr
            115                 120                 125

Leu Ser Leu Leu Arg Arg Gly Asp Val Leu Gly Ala Val Thr Arg Glu
        130                 135                 140

Ala Asn Pro Val Ala Gly Cys Glu Val Val Glu Leu Gly Thr Met Arg
145                 150                 155                 160

His Leu Ala Ile Ala Thr Pro Ser Leu Arg Asp Ala Tyr Met Val Asp
            165                 170                 175

Gly Lys Leu Asp Trp Ala Ala Met Pro Val Leu Arg Phe Gly Pro Lys
            180                 185                 190

Asp Val Leu Gln Asp Arg Asp Leu Asp Gly Arg Val Asp Gly Pro Val
            195                 200                 205

Gly Arg Arg Arg Val Ser Ile Val Pro Ser Ala Glu Gly Phe Gly Glu
        210                 215                 220

Ala Ile Arg Arg Gly Leu Gly Trp Gly Leu Leu Pro Glu Thr Gln Ala
225                 230                 235                 240

Ala Pro Met Leu Lys Ala Gly Glu Val Ile Leu Leu Asp Glu Ile Pro
            245                 250                 255

Ile Asp Thr Pro Met Tyr Trp Gln Arg Trp Arg Leu Glu Ser Arg Ser
            260                 265                 270

Leu Ala Arg Leu Thr Asp Ala Val Val Asp Ala Ala Ile Glu Gly Leu
        275                 280                 285

Arg Pro
    290

<210> SEQ ID NO 9
<211> LENGTH: 1470
<212> TYPE: DNA
<213> ORGANISM: Escherichia coli

<400> SEQUENCE: 9
atggtttccg aaactaaaac cacagaagcg ccgggcttac gccgtgaatt aaaggcgcgt      60
cacctgacga tgattgccat tggcggttcc atcggtacag tctttttgt tgcctctggc     120 gcaacgattt ctcaggcagg tccgggcggg gcattgctct cgtatatgct gattggcctg     180
atggtttact tcctgatgac cagtctcggt gaactggctg catatatgcc ggtttccggt     240
tcgtttgcca cttacggtca gaactatgtt gaagaaggct ttggcttcgc gctgggctgg     300
aactactggt acaactgggc ggtgactatc gccgttgacc tggttgcagc tcagctggtc     360
atgagctggt ggtccccgga tacaccgggc tggatctgga gtgcgttgtt cctcggcgtt     420
atcttcctgc tgaactacat ctcagttcgt ggctttggtg aagcggaata ctggttctca     480
ctgatcaaag tcacgacagt tattgtcttt atcatcgttg cgtgctgat gattatcggt     540 atcttcaaag gcgcgcagcc tgcgggctgg agcaactgga caatcggcga agcgccgttt     600
gctggtggtt ttgcggcgat gatcggcgta gctatgattg tcggcttctc tttccaggga     660
accgagctga tcgtattgc tgcaggcgag tccgaagatc cggcgaaaaa cattccacgc     720
gcggtacgtc aggtgttctg gcgaatcctg ttgttctatg tgttcgcgat cctgattatc     780

-continued

```
agcctgatta ttccgtacac cgatccgagc ctgctgcgta acgatgttaa agacatcagc    840
gttagtccgt tcaccctggt gttccagcac gcgggtctgc tctctgcggc ggcggtgatg    900
aacgcagtta ttctgacggc ggtgctgtca gcgggtaact ccggtatgta tgcgtctact    960
cgtatgctgt acaccctggc gtgtgacggt aaagcgccgc gcattttcgc taaactgtcg   1020
cgtggtggcg tgccgcgtaa tgcgctgtat gcgacgacgg tgattgccgg tctgtgcttc   1080
ctgacctcca tgtttggcaa ccagacggta tacctgtggc tgctgaacac ctccgggatg   1140
acgggtttta tcgcctggct ggggattgcc attagccact atcgcttccg tcgcggttac   1200
gtattgcagg acacgacat taacgatctg ccgtaccgtt caggtttctt cccactgggg   1260
ccgatcttcg cattcattct gtgtctgatt atcactttgg gccagaacta cgaagcgttc   1320
ctgaaagata ctattgactg gggcggcgta gcggcaacgt atattggtat cccgctgttc   1380
ctgattattt ggttcggcta caagctgatt aaaggaactc acttcgtacg ctacagcgaa   1440
atgaagttcc gcagaacga taagaaataa                                     1470
```

```
<210> SEQ ID NO 10
<211> LENGTH: 489
<212> TYPE: PRT
<213> ORGANISM: Escherichia coli

<400> SEQUENCE: 10
```

```
Met Val Ser Glu Thr Lys Thr Thr Glu Ala Pro Gly Leu Arg Arg Glu
1               5                   10                  15

Leu Lys Ala Arg His Leu Thr Met Ile Ala Ile Gly Gly Ser Ile Gly
            20                  25                  30

Thr Gly Leu Phe Val Ala Ser Gly Ala Thr Ile Ser Gln Ala Gly Pro
        35                  40                  45

Gly Gly Ala Leu Leu Ser Tyr Met Leu Ile Gly Leu Met Val Tyr Phe
    50                  55                  60

Leu Met Thr Ser Leu Gly Glu Leu Ala Ala Tyr Met Pro Val Ser Gly
65                  70                  75                  80

Ser Phe Ala Thr Tyr Gly Gln Asn Tyr Val Glu Glu Gly Phe Gly Phe
                85                  90                  95

Ala Leu Gly Trp Asn Tyr Trp Tyr Asn Trp Ala Val Thr Ile Ala Val
            100                 105                 110

Asp Leu Val Ala Ala Gln Leu Val Met Ser Trp Trp Phe Pro Asp Thr
        115                 120                 125

Pro Gly Trp Ile Trp Ser Ala Leu Phe Leu Gly Val Ile Phe Leu Leu
    130                 135                 140

Asn Tyr Ile Ser Val Arg Gly Phe Gly Glu Ala Glu Tyr Trp Phe Ser
145                 150                 155                 160

Leu Ile Lys Val Thr Thr Val Ile Val Phe Ile Ile Val Gly Val Leu
                165                 170                 175

Met Ile Ile Gly Ile Phe Lys Gly Ala Gln Pro Ala Gly Trp Ser Asn
            180                 185                 190

Trp Thr Ile Gly Glu Ala Pro Phe Ala Gly Gly Phe Ala Ala Met Ile
        195                 200                 205

Gly Val Ala Met Ile Val Gly Phe Ser Phe Gln Gly Thr Glu Leu Ile
    210                 215                 220

Gly Ile Ala Ala Gly Glu Ser Glu Asp Pro Ala Lys Asn Ile Pro Arg
225                 230                 235                 240

Ala Val Arg Gln Val Phe Trp Arg Ile Leu Leu Phe Tyr Val Phe Ala
                245                 250                 255
```

```
Ile Leu Ile Ile Ser Leu Ile Ile Pro Tyr Thr Asp Pro Ser Leu Leu
            260                 265                 270

Arg Asn Asp Val Lys Asp Ile Ser Val Ser Pro Phe Thr Leu Val Phe
        275                 280                 285

Gln His Ala Gly Leu Leu Ser Ala Ala Ala Val Met Asn Ala Val Ile
    290                 295                 300

Leu Thr Ala Val Leu Ser Ala Gly Asn Ser Gly Met Tyr Ala Ser Thr
305                 310                 315                 320

Arg Met Leu Tyr Thr Leu Ala Cys Asp Gly Lys Ala Pro Arg Ile Phe
                325                 330                 335

Ala Lys Leu Ser Arg Gly Gly Val Pro Arg Asn Ala Leu Tyr Ala Thr
            340                 345                 350

Thr Val Ile Ala Gly Leu Cys Phe Leu Thr Ser Met Phe Gly Asn Gln
        355                 360                 365

Thr Val Tyr Leu Trp Leu Leu Asn Thr Ser Gly Met Thr Gly Phe Ile
    370                 375                 380

Ala Trp Leu Gly Ile Ala Ile Ser His Tyr Arg Phe Arg Arg Gly Tyr
385                 390                 395                 400

Val Leu Gln Gly His Asp Ile Asn Asp Leu Pro Tyr Arg Ser Gly Phe
                405                 410                 415

Phe Pro Leu Gly Pro Ile Phe Ala Phe Ile Leu Cys Leu Ile Ile Thr
            420                 425                 430

Leu Gly Gln Asn Tyr Glu Ala Phe Leu Lys Asp Thr Ile Asp Trp Gly
        435                 440                 445

Gly Val Ala Ala Thr Tyr Ile Gly Ile Pro Leu Phe Leu Ile Ile Trp
    450                 455                 460

Phe Gly Tyr Lys Leu Ile Lys Gly Thr His Phe Val Arg Tyr Ser Glu
465                 470                 475                 480

Met Lys Phe Pro Gln Asn Asp Lys Lys
                485

<210> SEQ ID NO 11
<211> LENGTH: 444
<212> TYPE: PRT
<213> ORGANISM: Escherichia coli

<400> SEQUENCE: 11

Met Ser Ser Ala Lys Lys Ile Gly Leu Phe Ala Cys Thr Gly Val Val
1               5                   10                  15

Ala Gly Asn Met Met Gly Ser Gly Ile Ala Leu Leu Pro Ala Asn Leu
            20                  25                  30

Ala Ser Ile Gly Gly Ile Ala Ile Trp Gly Trp Ile Ile Ser Ile Ile
        35                  40                  45

Gly Ala Met Ser Leu Ala Tyr Val Tyr Ala Arg Leu Ala Thr Lys Asn
    50                  55                  60

Pro Gln Gln Gly Gly Pro Ile Ala Tyr Ala Gly Glu Ile Ser Pro Ala
65                  70                  75                  80

Phe Gly Phe Gln Thr Gly Val Leu Tyr Tyr His Ala Asn Trp Ile Gly
                85                  90                  95

Asn Leu Ala Ile Gly Ile Thr Ala Val Ser Tyr Leu Ser Thr Phe Phe
            100                 105                 110

Pro Val Leu Asn Asp Pro Val Pro Ala Gly Ile Ala Cys Ile Ala Ile
        115                 120                 125

Val Trp Val Phe Thr Phe Val Asn Met Leu Gly Gly Thr Trp Val Ser
```

```
                130             135             140
Arg Leu Thr Thr Ile Gly Leu Val Leu Val Leu Ile Pro Val Met
145                 150                 155                 160

Thr Ala Ile Val Gly Trp His Trp Phe Asp Ala Ala Thr Tyr Ala Ala
                165                 170                 175

Asn Trp Asn Thr Ala Asp Thr Thr Asp Gly His Ala Ile Ile Lys Ser
            180                 185                 190

Ile Leu Leu Cys Leu Trp Ala Phe Val Gly Val Glu Ser Ala Ala Val
        195                 200                 205

Ser Thr Gly Met Val Lys Asn Pro Lys Arg Thr Val Pro Leu Ala Thr
    210                 215                 220

Met Leu Gly Thr Gly Leu Ala Gly Ile Val Tyr Ile Ala Ala Thr Gln
225                 230                 235                 240

Val Leu Ser Gly Met Tyr Pro Ser Ser Val Met Ala Ala Ser Gly Ala
                245                 250                 255

Pro Phe Ala Ile Ser Ala Ser Thr Ile Leu Gly Asn Trp Ala Ala Pro
            260                 265                 270

Leu Val Ser Ala Phe Thr Ala Phe Ala Cys Leu Thr Ser Leu Gly Ser
        275                 280                 285

Trp Met Met Leu Val Gly Gln Ala Gly Val Arg Ala Ala Asn Asp Gly
    290                 295                 300

Asn Phe Pro Lys Val Tyr Gly Glu Val Asp Ser Asn Gly Ile Pro Lys
305                 310                 315                 320

Lys Gly Leu Leu Leu Ala Ala Val Lys Met Thr Ala Leu Met Ile Leu
                325                 330                 335

Ile Thr Leu Met Asn Ser Ala Gly Gly Lys Ala Ser Asp Leu Phe Gly
            340                 345                 350

Glu Leu Thr Gly Ile Ala Val Leu Leu Thr Met Leu Pro Tyr Phe Tyr
        355                 360                 365

Ser Cys Val Asp Leu Ile Arg Phe Glu Gly Val Asn Ile Arg Asn Phe
    370                 375                 380

Val Ser Leu Ile Cys Ser Val Leu Gly Cys Val Phe Cys Phe Ile Ala
385                 390                 395                 400

Leu Met Gly Ala Ser Ser Phe Glu Leu Ala Gly Thr Phe Ile Val Ser
                405                 410                 415

Leu Ile Ile Leu Met Phe Tyr Ala Arg Lys Met His Glu Arg Gln Ser
            420                 425                 430

His Ser Met Asp Asn His Thr Ala Ser Asn Ala His
        435                 440

<210> SEQ ID NO 12
<211> LENGTH: 558
<212> TYPE: DNA
<213> ORGANISM: Corynebacterium glutamicum

<400> SEQUENCE: 12
atgagtccca ccgttttgcc tgctacacaa gctgacttcc ctaagatcgt cgatgttctg      60
gttgaagcat cgccaacga tccagcattt ttacgatgga tcccgcagcc ggaccccggt     120
tcagcaaagc ttcgagcact tttcgaactg cagattgaga agcagtatgc agtggcggga     180
aatattgatg tcgcgcgtga ttctgaggga gaaatcgtcg gcgtcgcgtt atgggatcgg     240
ccagatggta atcacagtgc caaagatcaa gcagcgatgc tccccgggct cgtctccatt     300
ttcgggatca aggctgcgca ggtggcgtgg acggatttga gttcggctcg tttccacccc     360
```

```
aaattccccc attggtacct ctacaccgtg gcaacatcta gttctgcccg tggaacgggt     420
gttggcagtg cgcttcttaa tcacggaatc gctcgcgcgg gtgatgaagc tatctatttg     480
gaggcgacgc cgactcgtgc ggctcaacta tataaccgtc tgggattcgt gcccttgggt     540
tatatccccc tcagatga                                                   558
```

<210> SEQ ID NO 13
<211> LENGTH: 185
<212> TYPE: PRT
<213> ORGANISM: Corynebacterium glutamicum

<400> SEQUENCE: 13

```
Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Pro Thr Arg Ala Ala Gln Leu Tyr Asn Arg Leu Gly Phe
                165                 170                 175

Val Pro Leu Gly Tyr Ile Pro Leu Arg
            180                 185
```

<210> SEQ ID NO 14
<211> LENGTH: 288
<212> TYPE: PRT
<213> ORGANISM: Escherichia coli

<400> SEQUENCE: 14

```
Met Ala Glu Lys Lys Gln Trp His Glu Thr Leu His Asp Gln Phe Gly
1               5                   10                  15

Gln Tyr Phe Ala Val Asp Asn Val Leu Tyr His Glu Lys Thr Asp His
            20                  25                  30

Gln Asp Leu Ile Ile Phe Glu Asn Ala Ala Phe Gly Arg Val Met Ala
        35                  40                  45

Leu Asp Gly Val Val Gln Thr Thr Glu Arg Asp Glu Phe Ile Tyr His
    50                  55                  60

Glu Met Met Thr His Val Pro Leu Leu Ala His Gly His Ala Lys His
65                  70                  75                  80

Val Leu Ile Ile Gly Gly Gly Asp Gly Ala Met Leu Arg Glu Val Thr
                85                  90                  95

Arg His Lys Asn Val Glu Ser Ile Thr Met Val Glu Ile Asp Ala Gly
```

```
            100                 105                 110
Val Val Ser Phe Cys Arg Gln Tyr Leu Pro Asn His Asn Ala Gly Ser
        115                 120                 125

Tyr Asp Asp Pro Arg Phe Lys Leu Val Ile Asp Gly Val Asn Phe
130                 135                 140

Val Asn Gln Thr Ser Gln Thr Phe Asp Val Ile Ile Ser Asp Cys Thr
145                 150                 155                 160

Asp Pro Ile Gly Pro Gly Glu Ser Leu Phe Thr Ser Ala Phe Tyr Glu
                165                 170                 175

Gly Cys Lys Arg Cys Leu Asn Pro Gly Gly Ile Phe Val Ala Gln Asn
            180                 185                 190

Gly Val Cys Phe Leu Gln Gln Glu Glu Ala Ile Asp Ser His Arg Lys
        195                 200                 205

Leu Ser His Tyr Phe Ser Asp Val Gly Phe Tyr Gln Ala Ala Ile Pro
    210                 215                 220

Thr Tyr Tyr Gly Gly Ile Met Thr Phe Ala Trp Ala Thr Asp Asn Asp
225                 230                 235                 240

Ala Leu Arg His Leu Ser Thr Glu Ile Ile Gln Ala Arg Phe Leu Ala
                245                 250                 255

Ser Gly Leu Lys Cys Arg Tyr Tyr Asn Pro Ala Ile His Thr Ala Ala
            260                 265                 270

Phe Ala Leu Pro Gln Tyr Leu Gln Asp Ala Leu Ala Ser Gln Pro Ser
        275                 280                 285

<210> SEQ ID NO 15
<211> LENGTH: 445
<212> TYPE: PRT
<213> ORGANISM: Corynebacterium glutamicum

<400> SEQUENCE: 15

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
                20                  25                  30

Val Met Arg Leu Met Thr Glu Tyr Gly Asp Glu Leu Ala His Arg Ile
            35                  40                  45

Gly Gly Pro Leu Glu Val Arg Gly Ile Ala Val Ser Asp Ile Ser Lys
        50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190
```

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
                260                 265                 270

Glu Gly Lys Ser Ala Ile Ser Ala Arg Val His Pro Thr Leu Leu Pro
            275                 280                 285

Val Ser His Pro Leu Ala Ser Val Asn Lys Ser Phe Asn Ala Ile Phe
        290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Arg Ala Pro Gly Glu Ser Thr Tyr
                340                 345                 350

Ala Asn Leu Pro Ile Ala Asp Phe Gly Glu Thr Thr Thr Arg Tyr His
            355                 360                 365

Leu Asp Met Asp Val Glu Asp Arg Val Gly Val Leu Ala Glu Leu Ala
        370                 375                 380

Ser Leu Phe Ser Glu Gln Gly Ile Ser Leu Arg Thr Ile Arg Gln Glu
385                 390                 395                 400

Glu Arg Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
            435                 440                 445

<210> SEQ ID NO 16
<211> LENGTH: 810
<212> TYPE: PRT
<213> ORGANISM: Escherichia coli

<400> SEQUENCE: 16

Met Ser Val Ile Ala Gln Ala Gly Ala Lys Gly Arg Gln Leu His Lys
1               5                   10                  15

Phe Gly Gly Ser Ser Leu Ala Asp Val Lys Cys Tyr Leu Arg Val Ala
                20                  25                  30

Gly Ile Met Ala Glu Tyr Ser Gln Pro Asp Asp Met Met Val Val Ser
            35                  40                  45

Ala Ala Gly Ser Thr Thr Asn Gln Leu Ile Asn Trp Leu Lys Leu Ser
        50                  55                  60

Gln Thr Asp Arg Leu Ser Ala His Gln Val Gln Gln Thr Leu Arg Arg
65                  70                  75                  80

Tyr Gln Cys Asp Leu Ile Ser Gly Leu Leu Pro Ala Glu Glu Ala Asp
                85                  90                  95

Ser Leu Ile Ser Ala Phe Val Ser Asp Leu Glu Arg Leu Ala Ala Leu
            100                 105                 110

Leu Asp Ser Gly Ile Asn Asp Ala Val Tyr Ala Glu Val Val Gly His
        115                 120                 125

```
Gly Glu Val Trp Ser Ala Arg Leu Met Ser Ala Val Leu Asn Gln Gln
130                 135                 140

Gly Leu Pro Ala Ala Trp Leu Asp Ala Arg Glu Phe Leu Arg Ala Glu
145                 150                 155                 160

Arg Ala Ala Gln Pro Gln Val Asp Glu Gly Leu Ser Tyr Pro Leu Leu
                165                 170                 175

Gln Gln Leu Leu Val Gln His Pro Gly Lys Arg Leu Val Val Thr Gly
            180                 185                 190

Phe Ile Ser Arg Asn Asn Ala Gly Glu Thr Val Leu Leu Gly Arg Asn
        195                 200                 205

Gly Ser Asp Tyr Ser Ala Thr Gln Ile Gly Ala Leu Ala Gly Val Ser
210                 215                 220

Arg Val Thr Ile Trp Ser Asp Val Ala Gly Val Tyr Ser Ala Asp Pro
225                 230                 235                 240

Arg Lys Val Lys Asp Ala Cys Leu Leu Pro Leu Leu Arg Leu Asp Glu
                245                 250                 255

Ala Ser Glu Leu Ala Arg Leu Ala Ala Pro Val Leu His Ala Arg Thr
            260                 265                 270

Leu Gln Pro Val Ser Gly Ser Glu Ile Asp Leu Gln Leu Arg Cys Ser
        275                 280                 285

Tyr Thr Pro Asp Gln Gly Ser Thr Arg Ile Glu Arg Val Leu Ala Ser
290                 295                 300

Gly Thr Gly Ala Arg Ile Val Thr Ser His Asp Asp Val Cys Leu Ile
305                 310                 315                 320

Glu Phe Gln Val Pro Ala Ser Gln Asp Phe Lys Leu Ala His Lys Glu
                325                 330                 335

Ile Asp Gln Ile Leu Lys Arg Ala Gln Val Arg Pro Leu Ala Val Gly
            340                 345                 350

Val His Asn Asp Arg Gln Leu Leu Gln Phe Cys Tyr Thr Ser Glu Val
        355                 360                 365

Ala Asp Ser Ala Leu Lys Ile Leu Asp Glu Ala Gly Leu Pro Gly Glu
370                 375                 380

Leu Arg Leu Arg Gln Gly Leu Ala Leu Val Ala Met Val Gly Ala Gly
385                 390                 395                 400

Val Thr Arg Asn Pro Leu His Cys His Arg Phe Trp Gln Gln Leu Lys
                405                 410                 415

Gly Gln Pro Val Glu Phe Thr Trp Gln Ser Asp Asp Gly Ile Ser Leu
            420                 425                 430

Val Ala Val Leu Arg Thr Gly Pro Thr Glu Ser Leu Ile Gln Gly Leu
        435                 440                 445

His Gln Ser Val Phe Arg Ala Glu Lys Arg Ile Gly Leu Val Leu Phe
450                 455                 460

Gly Lys Gly Asn Ile Gly Ser Arg Trp Leu Glu Leu Phe Ala Arg Glu
465                 470                 475                 480

Gln Ser Thr Leu Ser Ala Arg Thr Gly Phe Glu Phe Val Leu Ala Gly
                485                 490                 495

Val Val Asp Ser Arg Arg Ser Leu Leu Ser Tyr Asp Gly Leu Asp Ala
            500                 505                 510

Ser Arg Ala Leu Ala Phe Phe Asn Asp Glu Ala Val Glu Gln Asp Glu
        515                 520                 525

Glu Ser Leu Phe Leu Trp Met Arg Ala His Pro Tyr Asp Asp Leu Val
530                 535                 540
```

-continued

Val Leu Asp Val Thr Ala Ser Gln Gln Leu Ala Asp Gln Tyr Leu Asp
545                 550                 555                 560

Phe Ala Ser His Gly Phe His Val Ile Ser Ala Asn Lys Leu Ala Gly
            565                 570                 575

Ala Ser Asp Ser Asn Lys Tyr Arg Gln Ile His Asp Ala Phe Glu Lys
            580                 585                 590

Thr Gly Arg His Trp Leu Tyr Asn Ala Thr Val Gly Ala Gly Leu Pro
            595                 600                 605

Ile Asn His Thr Val Arg Asp Leu Ile Asp Ser Gly Asp Thr Ile Leu
            610                 615                 620

Ser Ile Ser Gly Ile Phe Ser Gly Thr Leu Ser Trp Leu Phe Leu Gln
625                 630                 635                 640

Phe Asp Gly Ser Val Pro Phe Thr Glu Leu Val Asp Gln Ala Trp Gln
            645                 650                 655

Gln Gly Leu Thr Glu Pro Asp Pro Arg Asp Asp Leu Ser Gly Lys Asp
            660                 665                 670

Val Met Arg Lys Leu Val Ile Leu Ala Arg Glu Ala Gly Tyr Asn Ile
            675                 680                 685

Glu Pro Asp Gln Val Arg Val Glu Ser Leu Val Pro Ala His Cys Glu
            690                 695                 700

Gly Gly Ser Ile Asp His Phe Phe Glu Asn Gly Asp Glu Leu Asn Glu
705                 710                 715                 720

Gln Met Val Gln Arg Leu Glu Ala Ala Arg Glu Met Gly Leu Val Leu
            725                 730                 735

Arg Tyr Val Ala Arg Phe Asp Ala Asn Gly Lys Ala Arg Val Gly Val
            740                 745                 750

Glu Ala Val Arg Glu Asp His Pro Leu Ala Ser Leu Leu Pro Cys Asp
            755                 760                 765

Asn Val Phe Ala Ile Glu Ser Arg Trp Tyr Arg Asp Asn Pro Leu Val
            770                 775                 780

Ile Arg Gly Pro Gly Ala Gly Arg Asp Val Thr Ala Gly Ala Ile Gln
785                 790                 795                 800

Ser Asp Ile Asn Arg Leu Ala Gln Leu Leu
            805                 810

<210> SEQ ID NO 17
<211> LENGTH: 820
<212> TYPE: PRT
<213> ORGANISM: Escherichia coli

<400> SEQUENCE: 17

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
            35                  40                  45

Ala Met Ile Glu Lys Thr Ile Ser Gly Gln Asp Ala Leu Pro Asn Ile
        50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
            85                  90                  95

Glu Phe Ala Gln Ile Lys His Val Leu His Gly Ile Ser Leu Leu Gly
            100                 105                 110

```
Gln Cys Pro Asp Ser Ile Asn Ala Ala Leu Ile Cys Arg Gly Glu Lys
            115                 120                 125

Met Ser Ile Ala Ile Met Ala Gly Val Leu Glu Ala Arg Gly His Asn
130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
            195                 200                 205

Tyr Ser Ala Ala Val Leu Ala Ala Cys Leu Arg Ala Asp Cys Cys Glu
210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
            275                 280                 285

Gln Ala Pro Gly Thr Leu Ile Gly Ala Ser Arg Asp Glu Asp Glu Leu
290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
            355                 360                 365

Arg Ala Glu Arg Ala Met Gln Glu Glu Phe Tyr Leu Glu Leu Lys Glu
370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Val Asn Asn Asp Asp Ala
            435                 440                 445

Thr Thr Gly Val Arg Val Thr His Gln Met Leu Phe Asn Thr Asp Gln
450                 455                 460

Val Ile Glu Val Phe Val Ile Gly Val Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
            515                 520                 525
```

-continued

Lys Glu Pro Phe Asn Leu Gly Arg Leu Ile Arg Leu Val Lys Glu Tyr
            530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
            565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
            595                 600                 605

Val Gly Ala Gly Leu Pro Val Ile Glu Asn Leu Gln Asn Leu Leu Asn
610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
            645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
            675                 680                 685

Glu Thr Gly Arg Glu Leu Glu Leu Ala Asp Ile Glu Ile Glu Pro Val
690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
            725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
            755                 760                 765

Phe Lys Val Lys Asn Gly Glu Asn Ala Leu Ala Phe Tyr Ser His Tyr
770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
            805                 810                 815

Lys Leu Gly Val
            820

<210> SEQ ID NO 18
<211> LENGTH: 445
<212> TYPE: PRT
<213> ORGANISM: Escherichia coli

<400> SEQUENCE: 18

Met Lys Lys Ser Val Asp Phe Ile Gly Val Gly Thr Gly Pro Phe Asn
1               5                   10                  15

Leu Ser Ile Ala Ala Leu Ser His Gln Ile Glu Glu Leu Asn Cys Leu
            20                  25                  30

Phe Phe Asp Glu His Pro His Phe Ser Trp His Pro Gly Met Leu Val
        35                  40                  45

Pro Asp Cys His Met Gln Thr Val Phe Leu Lys Asp Leu Val Ser Ala
    50                  55                  60

Val Ala Pro Thr Asn Pro Tyr Ser Phe Val Asn Tyr Leu Val Lys His
65                  70                  75                  80

```
Lys Lys Phe Tyr Arg Phe Leu Thr Ser Arg Leu Arg Thr Val Ser Arg
                85                  90                  95

Glu Glu Phe Ser Asp Tyr Leu Arg Trp Ala Ala Glu Asp Met Asn Asn
            100                 105                 110

Leu Tyr Phe Ser His Thr Val Glu Asn Ile Asp Phe Asp Lys Lys Ser
        115                 120                 125

Arg Leu Phe Leu Val Gln Thr Ser Arg Gly Glu Tyr Phe Ala Arg Asn
    130                 135                 140

Ile Cys Leu Gly Thr Gly Lys Gln Pro Tyr Leu Pro Pro Cys Val Lys
145                 150                 155                 160

His Val Thr Gln Ser Cys Phe His Ala Ser Glu Met Asn Leu Arg Arg
                165                 170                 175

Pro Asp Leu Ser Gly Lys Arg Ile Thr Val Val Gly Gly Gln Ser
            180                 185                 190

Gly Ala Asp Leu Phe Leu Asn Ala Leu Arg Gly Glu Trp Gly Glu Ala
        195                 200                 205

Ala Glu Ile Asn Trp Val Ser Arg Arg Asn Asn Phe Asn Ala Leu Asp
    210                 215                 220

Glu Ala Ala Phe Ala Asp Glu Tyr Phe Thr Pro Glu Tyr Ile Ser Gly
225                 230                 235                 240

Phe Ser Gly Leu Lys Glu Asp Ile Arg His Gln Leu Leu Asp Glu Gln
                245                 250                 255

Lys Met Thr Ser Asp Gly Ile Thr Ala Asp Ser Leu Leu Thr Ile Tyr
            260                 265                 270

Arg Glu Leu Tyr His Arg Phe Glu Val Leu Arg Lys Pro Arg Asn Ile
        275                 280                 285

Arg Leu Leu Pro Ser Arg Ser Val Thr Thr Leu Glu Ser Ser Gly Pro
    290                 295                 300

Gly Trp Lys Leu Leu Met Glu His His Leu Asp Arg Gly Arg Glu Ser
305                 310                 315                 320

Leu Glu Ser Asp Val Val Ile Phe Ala Thr Gly Tyr Arg Ser Ala Leu
                325                 330                 335

Pro Gln Ile Leu Pro Ser Leu Met Pro Leu Ile Thr Met His Asp Lys
            340                 345                 350

Asn Thr Phe Lys Val Arg Asp Asp Phe Thr Leu Glu Trp Ser Gly Pro
        355                 360                 365

Lys Glu Asn Asn Ile Phe Ala Val Asn Ala Ser Met Gln Thr His Gly
    370                 375                 380

Ile Ala Glu Pro Gln Leu Ser Leu Met Ala Trp Arg Ser Ala Arg Ile
385                 390                 395                 400

Leu Asn Arg Val Leu Gly Arg Asp Leu Phe Asp Leu Ser Met Pro Pro
                405                 410                 415

Ala Leu Ile Gln Trp Arg Ser Gly Ser Arg Lys Lys Pro Gln Pro Glu
            420                 425                 430

Ala Ala Ala Leu Thr His Tyr Thr Thr Asn Ile Gln Glu
        435                 440                 445

<210> SEQ ID NO 19
<211> LENGTH: 472
<212> TYPE: PRT
<213> ORGANISM: Escherichia coli

<400> SEQUENCE: 19

Met Glu Thr Asn Ile Val Glu Val Glu Asn Phe Val Gln Gln Ser Glu
```

-continued

```
1               5                   10                  15
Glu Arg Arg Gly Ser Ala Phe Thr Gln Glu Val Lys Arg Tyr Leu Glu
                20                  25                  30
Arg Tyr Pro Asn Thr Gln Tyr Val Asp Val Leu Leu Thr Asp Leu Asn
                35                  40                  45
Gly Cys Phe Arg Gly Lys Arg Ile Pro Val Ser Ser Leu Lys Lys Leu
 50                  55                  60
Glu Lys Gly Cys Tyr Phe Pro Ala Ser Val Phe Ala Met Asp Ile Leu
 65                  70                  75                  80
Gly Asn Val Val Glu Glu Ala Gly Leu Gly Gln Glu Met Gly Glu Pro
                85                  90                  95
Asp Arg Thr Cys Val Pro Val Leu Gly Ser Leu Thr Pro Ser Ala Ala
                100                 105                 110
Asp Pro Glu Phe Ile Gly Gln Met Leu Leu Thr Met Val Asp Glu Asp
                115                 120                 125
Gly Ala Pro Phe Asp Val Glu Pro Arg Asn Val Leu Asn Arg Leu Trp
130                 135                 140
Gln Gln Leu Arg Gln Arg Gly Leu Phe Pro Val Val Ala Val Glu Leu
145                 150                 155                 160
Glu Phe Tyr Leu Leu Asp Arg Gln Arg Asp Ala Glu Gly Tyr Leu Gln
                165                 170                 175
Pro Pro Cys Ala Pro Gly Thr Asp Asp Arg Asn Thr Gln Ser Gln Val
                180                 185                 190
Tyr Ser Val Asp Asn Leu Asn His Phe Ala Asp Val Leu Asn Asp Ile
                195                 200                 205
Asp Glu Leu Ala Gln Leu Gln Leu Ile Pro Ala Asp Gly Ala Val Ala
                210                 215                 220
Glu Ala Ser Pro Gly Gln Phe Glu Ile Asn Leu Tyr His Thr Asp Asn
225                 230                 235                 240
Val Leu Glu Ala Cys Asp Asp Ala Leu Ala Leu Lys Arg Leu Val Arg
                245                 250                 255
Leu Met Ala Glu Lys His Lys Met His Ala Thr Phe Met Ala Lys Pro
                260                 265                 270
Tyr Glu Glu His Ala Gly Ser Gly Met His Ile His Ile Ser Met Gln
                275                 280                 285
Asn Asn Arg Gly Glu Asn Val Leu Ser Asp Ala Glu Gly Glu Asp Ser
                290                 295                 300
Pro Leu Leu Lys Lys Met Leu Ala Gly Met Ile Asp Leu Met Pro Ser
305                 310                 315                 320
Ser Met Ala Leu Leu Ala Pro Asn Val Asn Ser Tyr Arg Arg Phe Gln
                325                 330                 335
Pro Gly Met Tyr Val Pro Thr Gln Ala Ser Trp Gly His Asn Asn Arg
                340                 345                 350
Thr Val Ala Leu Arg Ile Pro Cys Gly Asp Arg His Asn His Arg Val
                355                 360                 365
Glu Tyr Arg Val Ala Gly Ala Asp Ala Asn Pro Tyr Leu Val Met Ala
                370                 375                 380
Ala Ile Phe Ala Gly Ile Leu His Gly Leu Asp Asn Glu Leu Pro Leu
385                 390                 395                 400
Gln Glu Glu Val Glu Gly Asn Gly Leu Glu Gln Glu Gly Leu Pro Phe
                405                 410                 415
Pro Ile Arg Gln Ser Asp Ala Leu Gly Glu Phe Ile Glu Asn Asp His
                420                 425                 430
```

Leu Arg Arg Tyr Leu Gly Glu Arg Phe Cys His Val Tyr His Ala Cys
        435                 440                 445

Lys Asn Asp Glu Leu Leu Gln Phe Glu Arg Leu Ile Thr Glu Thr Glu
    450                 455                 460

Ile Glu Trp Met Leu Lys Asn Ala
465                 470

<210> SEQ ID NO 20
<211> LENGTH: 732
<212> TYPE: PRT
<213> ORGANISM: Escherichia coli

<400> SEQUENCE: 20

Met Ser Lys Leu Lys Ile Ala Val Ser Asp Ser Cys Pro Asp Cys Phe
1               5                   10                  15

Thr Thr Gln Arg Glu Cys Ile Tyr Ile Asn Glu Ser Arg Asn Ile Asp
            20                  25                  30

Val Ala Ala Ile Val Leu Ser Leu Asn Asp Val Thr Cys Gly Lys Leu
        35                  40                  45

Asp Glu Ile Asp Ala Thr Gly Tyr Gly Ile Pro Val Phe Ile Ala Thr
    50                  55                  60

Glu Asn Gln Glu Arg Val Pro Ala Glu Tyr Leu Pro Arg Ile Ser Gly
65                  70                  75                  80

Val Phe Glu Asn Cys Glu Ser Arg Arg Glu Phe Tyr Gly Arg Gln Leu
                85                  90                  95

Glu Thr Ala Ala Ser His Tyr Glu Thr Gln Leu Arg Pro Pro Phe Phe
            100                 105                 110

Arg Ala Leu Val Asp Tyr Val Asn Gln Gly Asn Ser Ala Phe Asp Cys
        115                 120                 125

Pro Gly His Gln Gly Gly Glu Phe Phe Arg Arg His Pro Ala Gly Asn
    130                 135                 140

Gln Phe Val Glu Tyr Phe Gly Glu Ala Leu Phe Arg Ala Asp Leu Cys
145                 150                 155                 160

Asn Ala Asp Val Ala Met Gly Asp Leu Leu Ile His Glu Gly Ala Pro
                165                 170                 175

Cys Ile Ala Gln Gln His Ala Ala Lys Val Phe Asn Ala Asp Lys Thr
            180                 185                 190

Tyr Phe Val Leu Asn Gly Thr Ser Ser Ser Asn Lys Val Val Leu Asn
        195                 200                 205

Ala Leu Leu Thr Pro Gly Asp Leu Val Leu Phe Asp Arg Asn Asn His
    210                 215                 220

Lys Ser Asn His His Gly Ala Leu Leu Gln Ala Gly Ala Thr Pro Val
225                 230                 235                 240

Tyr Leu Glu Thr Ala Arg Asn Pro Tyr Gly Phe Ile Gly Gly Ile Asp
                245                 250                 255

Ala His Cys Phe Glu Glu Ser Tyr Leu Arg Glu Leu Ile Ala Glu Val
            260                 265                 270

Ala Pro Gln Arg Ala Lys Glu Ala Arg Pro Phe Arg Leu Ala Val Ile
        275                 280                 285

Gln Leu Gly Thr Tyr Asp Gly Thr Ile Tyr Asn Ala Arg Gln Val Val
    290                 295                 300

Asp Lys Ile Gly His Leu Cys Asp Tyr Ile Leu Phe Asp Ser Ala Trp
305                 310                 315                 320

Val Gly Tyr Glu Gln Phe Ile Pro Met Met Ala Asp Cys Ser Pro Leu

```
                    325                 330                 335
Leu Leu Asp Leu Asn Glu Asn Asp Pro Gly Ile Leu Val Thr Gln Ser
            340                 345                 350

Val His Lys Gln Gln Ala Gly Phe Ser Gln Thr Ser Gln Ile His Lys
            355                 360                 365

Lys Asp Ser His Ile Lys Gly Gln Gln Arg Tyr Val Pro His Lys Arg
            370                 375                 380

Met Asn Asn Ala Phe Met Met His Ala Ser Thr Ser Pro Phe Tyr Pro
385                 390                 395                 400

Leu Phe Ala Ala Leu Asn Ile Asn Ala Lys Met His Glu Gly Val Ser
                405                 410                 415

Gly Arg Asn Met Trp Met Asp Cys Val Val Asn Gly Ile Asn Ala Arg
                420                 425                 430

Lys Leu Ile Leu Asp Asn Cys Gln His Ile Arg Pro Phe Val Pro Glu
                435                 440                 445

Leu Val Asp Gly Lys Pro Trp Gln Ser Tyr Glu Thr Ala Gln Ile Ala
            450                 455                 460

Val Asp Leu Arg Phe Phe Gln Phe Val Pro Gly Glu His Trp His Ser
465                 470                 475                 480

Phe Glu Gly Tyr Ala Glu Asn Gln Tyr Phe Val Asp Pro Cys Lys Leu
                485                 490                 495

Leu Leu Thr Thr Pro Gly Ile Asp Ala Arg Asn Gly Glu Tyr Glu Ala
            500                 505                 510

Phe Gly Val Pro Ala Thr Ile Leu Ala Asn Phe Leu Arg Glu Asn Gly
            515                 520                 525

Val Val Pro Glu Lys Cys Asp Leu Asn Ser Ile Leu Phe Leu Leu Thr
530                 535                 540

Pro Ala Glu Asp Met Ala Lys Leu Gln Gln Leu Val Ala Leu Leu Val
545                 550                 555                 560

Arg Phe Glu Lys Leu Leu Glu Ser Asp Ala Pro Leu Ala Glu Val Leu
                565                 570                 575

Pro Ser Ile Tyr Lys Gln His Glu Glu Arg Tyr Ala Gly Tyr Thr Leu
            580                 585                 590

Arg Gln Leu Cys Gln Glu Met His Asp Leu Tyr Ala Arg His Asn Val
            595                 600                 605

Lys Gln Leu Gln Lys Glu Met Phe Arg Lys Glu His Phe Pro Arg Val
            610                 615                 620

Ser Met Asn Pro Gln Glu Ala Asn Tyr Ala Tyr Leu Arg Gly Glu Val
625                 630                 635                 640

Glu Leu Val Arg Leu Pro Asp Ala Glu Gly Arg Ile Ala Ala Glu Gly
                645                 650                 655

Ala Leu Pro Tyr Pro Pro Gly Val Leu Cys Val Val Pro Gly Glu Ile
                660                 665                 670

Trp Gly Gly Ala Val Leu Arg Tyr Phe Ser Ala Leu Glu Glu Gly Ile
            675                 680                 685

Asn Leu Leu Pro Gly Phe Ala Pro Glu Leu Gln Gly Val Tyr Ile Glu
            690                 695                 700

Glu His Asp Gly Arg Lys Gln Val Trp Cys Tyr Val Ile Lys Pro Arg
705                 710                 715                 720

Asp Ala Gln Ser Thr Leu Leu Lys Gly Glu Lys Leu
                725                 730
```

<210> SEQ ID NO 21

-continued

```
<211> LENGTH: 439
<212> TYPE: PRT
<213> ORGANISM: Escherichia coli

<400> SEQUENCE: 21
```

| Met | Ser | Gln | Ala | Lys | Ser | Asn | Lys | Met | Gly | Val | Val | Gln | Leu | Thr | Ile |
|---|---|---|---|---|---|---|---|---|---|---|---|---|---|---|---|
| 1 | | | | 5 | | | | | 10 | | | | | 15 | |

| Leu | Thr | Met | Val | Asn | Met | Met | Gly | Ser | Gly | Ile | Ile | Met | Leu | Pro | Thr |
|---|---|---|---|---|---|---|---|---|---|---|---|---|---|---|---|
| | | | 20 | | | | | 25 | | | | | 30 | | |

| Lys | Leu | Ala | Glu | Val | Gly | Thr | Ile | Ser | Ile | Ile | Ser | Trp | Leu | Val | Thr |
|---|---|---|---|---|---|---|---|---|---|---|---|---|---|---|---|
| | | 35 | | | | | 40 | | | | | 45 | | | |

| Ala | Val | Gly | Ser | Met | Ala | Leu | Ala | Trp | Ala | Phe | Ala | Lys | Cys | Gly | Met |
|---|---|---|---|---|---|---|---|---|---|---|---|---|---|---|---|
| 50 | | | | | 55 | | | | | 60 | | | | | |

| Phe | Ser | Arg | Lys | Ser | Gly | Gly | Met | Gly | Gly | Tyr | Ala | Glu | Tyr | Ala | Phe |
|---|---|---|---|---|---|---|---|---|---|---|---|---|---|---|---|
| 65 | | | | | 70 | | | | | 75 | | | | | 80 |

| Gly | Lys | Ser | Gly | Asn | Phe | Met | Ala | Asn | Tyr | Thr | Tyr | Gly | Val | Ser | Leu |
|---|---|---|---|---|---|---|---|---|---|---|---|---|---|---|---|
| | | | | 85 | | | | | 90 | | | | | 95 | |

| Leu | Ile | Ala | Asn | Val | Ala | Ile | Ala | Ile | Ser | Ala | Val | Gly | Tyr | Gly | Thr |
|---|---|---|---|---|---|---|---|---|---|---|---|---|---|---|---|
| | | | 100 | | | | | 105 | | | | | 110 | | |

| Glu | Leu | Leu | Gly | Ala | Ser | Leu | Ser | Pro | Val | Gln | Ile | Gly | Leu | Ala | Thr |
|---|---|---|---|---|---|---|---|---|---|---|---|---|---|---|---|
| | | 115 | | | | | 120 | | | | | 125 | | | |

| Ile | Gly | Val | Leu | Trp | Ile | Cys | Thr | Val | Ala | Asn | Phe | Gly | Gly | Ala | Arg |
|---|---|---|---|---|---|---|---|---|---|---|---|---|---|---|---|
| 130 | | | | | 135 | | | | | 140 | | | | | |

| Ile | Thr | Gly | Gln | Ile | Ser | Ser | Ile | Thr | Val | Trp | Gly | Val | Ile | Ile | Pro |
|---|---|---|---|---|---|---|---|---|---|---|---|---|---|---|---|
| 145 | | | | | 150 | | | | | 155 | | | | | 160 |

| Val | Val | Gly | Leu | Cys | Ile | Ile | Gly | Trp | Phe | Trp | Phe | Ser | Pro | Thr | Leu |
|---|---|---|---|---|---|---|---|---|---|---|---|---|---|---|---|
| | | | | 165 | | | | | 170 | | | | | 175 | |

| Tyr | Val | Asp | Ser | Trp | Asn | Pro | His | His | Ala | Pro | Phe | Phe | Ser | Ala | Val |
|---|---|---|---|---|---|---|---|---|---|---|---|---|---|---|---|
| | | | 180 | | | | | 185 | | | | | 190 | | |

| Gly | Ser | Ser | Ile | Ala | Met | Thr | Leu | Trp | Ala | Phe | Leu | Gly | Leu | Glu | Ser |
|---|---|---|---|---|---|---|---|---|---|---|---|---|---|---|---|
| | | 195 | | | | | 200 | | | | | 205 | | | |

| Ala | Cys | Ala | Asn | Thr | Asp | Val | Val | Glu | Asn | Pro | Glu | Arg | Asn | Val | Pro |
|---|---|---|---|---|---|---|---|---|---|---|---|---|---|---|---|
| 210 | | | | | 215 | | | | | 220 | | | | | |

| Ile | Ala | Val | Leu | Gly | Gly | Thr | Leu | Gly | Ala | Ala | Val | Ile | Tyr | Ile | Val |
|---|---|---|---|---|---|---|---|---|---|---|---|---|---|---|---|
| 225 | | | | | 230 | | | | | 235 | | | | | 240 |

| Ser | Thr | Asn | Val | Ile | Ala | Gly | Ile | Val | Pro | Asn | Met | Glu | Leu | Ala | Asn |
|---|---|---|---|---|---|---|---|---|---|---|---|---|---|---|---|
| | | | | 245 | | | | | 250 | | | | | 255 | |

| Ser | Thr | Ala | Pro | Phe | Gly | Leu | Ala | Phe | Ala | Gln | Met | Phe | Thr | Pro | Glu |
|---|---|---|---|---|---|---|---|---|---|---|---|---|---|---|---|
| | | | 260 | | | | | 265 | | | | | 270 | | |

| Val | Gly | Lys | Val | Ile | Met | Ala | Leu | Met | Val | Met | Ser | Cys | Cys | Gly | Ser |
|---|---|---|---|---|---|---|---|---|---|---|---|---|---|---|---|
| | | 275 | | | | | 280 | | | | | 285 | | | |

| Leu | Leu | Gly | Trp | Gln | Phe | Thr | Ile | Ala | Gln | Val | Phe | Lys | Ser | Ser | Ser |
|---|---|---|---|---|---|---|---|---|---|---|---|---|---|---|---|
| 290 | | | | | 295 | | | | | 300 | | | | | |

| Asp | Glu | Gly | Tyr | Phe | Pro | Lys | Ile | Phe | Ser | Arg | Val | Thr | Lys | Val | Asp |
|---|---|---|---|---|---|---|---|---|---|---|---|---|---|---|---|
| 305 | | | | | 310 | | | | | 315 | | | | | 320 |

| Ala | Pro | Val | Gln | Gly | Met | Leu | Thr | Ile | Val | Ile | Gln | Ser | Gly | Leu |
|---|---|---|---|---|---|---|---|---|---|---|---|---|---|---|
| | | | | 325 | | | | | 330 | | | | | 335 |

| Ala | Leu | Met | Thr | Ile | Ser | Pro | Ser | Leu | Asn | Ser | Gln | Phe | Asn | Val | Leu |
|---|---|---|---|---|---|---|---|---|---|---|---|---|---|---|---|
| | | | 340 | | | | | 345 | | | | | 350 | | |

| Val | Asn | Leu | Ala | Val | Val | Thr | Asn | Ile | Ile | Pro | Tyr | Ile | Leu | Ser | Met |
|---|---|---|---|---|---|---|---|---|---|---|---|---|---|---|---|
| | | 355 | | | | | 360 | | | | | 365 | | | |

| Ala | Ala | Leu | Val | Ile | Ile | Gln | Lys | Val | Ala | Asn | Val | Pro | Pro | Ser | Lys |
|---|---|---|---|---|---|---|---|---|---|---|---|---|---|---|---|
| 370 | | | | | 375 | | | | | 380 | | | | | |

| Ala | Lys | Val | Ala | Asn | Phe | Val | Ala | Phe | Val | Gly | Ala | Met | Tyr | Ser | Phe |
|---|---|---|---|---|---|---|---|---|---|---|---|---|---|---|---|

```
                385                 390                 395                 400
Tyr Ala Leu Tyr Ser Ser Gly Glu Glu Ala Met Leu Tyr Gly Ser Ile
                    405                 410                 415

Val Thr Phe Leu Gly Trp Thr Leu Tyr Gly Leu Val Ser Pro Arg Phe
                420                 425                 430

Glu Leu Lys Asn Lys His Gly
            435
```

<210> SEQ ID NO 22
<211> LENGTH: 445
<212> TYPE: PRT
<213> ORGANISM: Corynebacterium glutamicum

<400> SEQUENCE: 22

```
Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
                20                  25                  30

Val Met Arg Leu Met Thr Glu Tyr Gly Asp Glu Leu Ala His Arg Ile
                35                  40                  45

Gly Gly Pro Leu Glu Val Arg Gly Ile Ala Val Ser Asp Ile Ser Lys
            50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
                100                 105                 110

Ser Val Val Thr Ala Asn Lys Ala Leu Val Ala Ala His Ser Ala Glu
            115                 120                 125

Leu Ala Asp Ala Ala Glu Ala Ala Asn Val Asp Leu Tyr Phe Glu Ala
        130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
                180                 185                 190

Ser Leu Ala Glu Ala Thr Arg Leu Gly Tyr Ala Glu Ala Asp Pro Thr
            195                 200                 205

Ala Asp Val Glu Gly His Asp Ala Ala Ser Lys Ala Ala Ile Leu Ala
        210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
                260                 265                 270

Glu Gly Lys Ser Ala Ile Ser Ala Arg Val His Pro Thr Leu Leu Pro
            275                 280                 285

Val Ser His Pro Leu Ala Ser Val Asn Lys Ser Phe Asn Ala Ile Phe
        290                 295                 300

Val Glu Ala Glu Ala Ala Gly Arg Leu Met Phe Tyr Gly Asn Gly Ala
305                 310                 315                 320
```

```
Gly Gly Ala Pro Thr Ala Ser Ala Val Leu Gly Asp Val Val Gly Ala
                325                 330                 335

Ala Arg Asn Lys Val His Gly Arg Ala Pro Gly Glu Ser Thr Tyr
            340                 345                 350

Ala Asn Leu Pro Ile Ala Asp Phe Gly Glu Thr Thr Thr Arg Tyr His
            355                 360                 365

Leu Asp Met Asp Val Glu Asp Arg Val Gly Val Leu Ala Glu Leu Ala
            370                 375                 380

Ser Leu Phe Ser Glu Gln Gly Ile Ser Leu Arg Thr Ile Arg Gln Glu
385                 390                 395                 400

Glu Arg Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
            435                 440                 445
```

<210> SEQ ID NO 23
<211> LENGTH: 810
<212> TYPE: PRT
<213> ORGANISM: Escherichia coli

<400> SEQUENCE: 23

```
Met Ser Val Ile Ala Gln Ala Gly Ala Lys Gly Arg Gln Leu His Lys
1               5                   10                  15

Phe Gly Gly Ser Ser Leu Ala Asp Val Lys Cys Tyr Leu Arg Val Ala
                20                  25                  30

Gly Ile Met Ala Glu Tyr Ser Gln Pro Asp Asp Met Met Val Val Ser
            35                  40                  45

Ala Ala Gly Ser Thr Thr Asn Gln Leu Ile Asn Trp Leu Lys Leu Ser
        50                  55                  60

Gln Thr Asp Arg Leu Ser Ala His Gln Val Gln Gln Thr Leu Arg Arg
65                  70                  75                  80

Tyr Gln Cys Asp Leu Ile Ser Gly Leu Leu Pro Ala Glu Glu Ala Asp
                85                  90                  95

Ser Leu Ile Ser Ala Phe Val Ser Asp Leu Glu Arg Leu Ala Ala Leu
                100                 105                 110

Leu Asp Ser Gly Ile Asn Asp Ala Val Tyr Ala Glu Val Val Gly His
            115                 120                 125

Gly Glu Val Trp Ser Ala Arg Leu Met Ser Ala Val Leu Asn Gln Gln
        130                 135                 140

Gly Leu Pro Ala Ala Trp Leu Asp Ala Arg Glu Phe Leu Arg Ala Glu
145                 150                 155                 160

Arg Ala Ala Gln Pro Gln Val Asp Glu Gly Leu Ser Tyr Pro Leu Leu
                165                 170                 175

Gln Gln Leu Leu Val Gln His Pro Gly Lys Arg Leu Val Val Thr Gly
            180                 185                 190

Phe Ile Ser Arg Asn Asn Ala Gly Glu Thr Val Leu Leu Gly Arg Asn
        195                 200                 205

Gly Ser Asp Tyr Ser Ala Thr Gln Ile Gly Ala Leu Ala Gly Val Ser
    210                 215                 220

Arg Val Thr Ile Trp Ser Asp Val Ala Gly Val Tyr Ser Ala Asp Pro
225                 230                 235                 240

Arg Lys Val Lys Asp Ala Cys Leu Leu Pro Leu Leu Arg Leu Asp Glu
                245                 250                 255
```

-continued

```
Ala Ser Glu Leu Ala Arg Leu Ala Ala Pro Val Leu His Ala Arg Thr
            260                 265                 270

Leu Gln Pro Val Ser Gly Ser Glu Ile Asp Leu Gln Leu Arg Cys Ser
        275                 280                 285

Tyr Thr Pro Asp Gln Gly Ser Thr Arg Ile Glu Arg Val Leu Ala Ser
    290                 295                 300

Gly Thr Gly Ala Arg Ile Val Thr Ser His Asp Asp Val Cys Leu Ile
305                 310                 315                 320

Glu Phe Gln Val Pro Ala Ser Gln Asp Phe Lys Leu Ala His Lys Glu
                325                 330                 335

Ile Asp Gln Ile Leu Lys Arg Ala Gln Val Arg Pro Leu Ala Val Gly
            340                 345                 350

Val His Asn Asp Arg Gln Leu Leu Gln Phe Cys Tyr Thr Ser Glu Val
        355                 360                 365

Ala Asp Ser Ala Leu Lys Ile Leu Asp Glu Ala Gly Leu Pro Gly Glu
    370                 375                 380

Leu Arg Leu Arg Gln Gly Leu Ala Leu Val Ala Met Val Gly Ala Gly
385                 390                 395                 400

Val Thr Arg Asn Pro Leu His Cys His Arg Phe Trp Gln Gln Leu Lys
                405                 410                 415

Gly Gln Pro Val Glu Phe Thr Trp Gln Ser Asp Asp Gly Ile Ser Leu
            420                 425                 430

Val Ala Val Leu Arg Thr Gly Pro Thr Glu Ser Leu Ile Gln Gly Leu
        435                 440                 445

His Gln Ser Val Phe Arg Ala Glu Lys Arg Ile Gly Leu Val Leu Phe
    450                 455                 460

Gly Lys Gly Asn Ile Gly Ser Arg Trp Leu Glu Leu Phe Ala Arg Glu
465                 470                 475                 480

Gln Ser Thr Leu Ser Ala Arg Thr Gly Phe Glu Phe Val Leu Ala Gly
                485                 490                 495

Val Val Asp Ser Arg Arg Ser Leu Leu Ser Tyr Asp Gly Leu Asp Ala
            500                 505                 510

Ser Arg Ala Leu Ala Phe Phe Asn Asp Glu Ala Val Glu Gln Asp Glu
        515                 520                 525

Glu Ser Leu Phe Leu Trp Met Arg Ala His Pro Tyr Asp Asp Leu Val
    530                 535                 540

Val Leu Asp Val Thr Ala Ser Gln Gln Leu Ala Asp Gln Tyr Leu Asp
545                 550                 555                 560

Phe Ala Ser His Gly Phe His Val Ile Ser Ala Asn Lys Leu Ala Gly
                565                 570                 575

Ala Ser Asp Ser Asn Lys Tyr Arg Gln Ile His Asp Ala Phe Glu Lys
            580                 585                 590

Thr Gly Arg His Trp Leu Tyr Asn Ala Thr Val Gly Ala Gly Leu Pro
        595                 600                 605

Ile Asn His Thr Val Arg Asp Leu Ile Asp Ser Gly Asp Thr Ile Leu
    610                 615                 620

Ser Ile Ser Gly Ile Phe Ser Gly Thr Leu Ser Trp Leu Phe Leu Gln
625                 630                 635                 640

Phe Asp Gly Ser Val Pro Phe Thr Glu Leu Val Asp Gln Ala Trp Gln
                645                 650                 655

Gln Gly Leu Thr Glu Pro Asp Pro Arg Asp Asp Leu Ser Gly Lys Asp
            660                 665                 670
```

```
Val Met Arg Lys Leu Val Ile Leu Ala Arg Glu Ala Gly Tyr Asn Ile
            675                 680                 685

Glu Pro Asp Gln Val Arg Val Glu Ser Leu Val Pro Ala His Cys Glu
690                 695                 700

Gly Gly Ser Ile Asp His Phe Phe Glu Asn Gly Asp Glu Leu Asn Glu
705                 710                 715                 720

Gln Met Val Gln Arg Leu Glu Ala Ala Arg Glu Met Gly Leu Val Leu
                725                 730                 735

Arg Tyr Val Ala Arg Phe Asp Ala Asn Gly Lys Ala Arg Val Gly Val
            740                 745                 750

Glu Ala Val Arg Glu Asp His Pro Leu Ala Ser Leu Leu Pro Cys Asp
        755                 760                 765

Asn Val Phe Ala Ile Glu Ser Arg Trp Tyr Arg Asp Asn Pro Leu Val
770                 775                 780

Ile Arg Gly Pro Gly Ala Gly Arg Asp Val Thr Ala Gly Ala Ile Gln
785                 790                 795                 800

Ser Asp Ile Asn Arg Leu Ala Gln Leu Leu
                805                 810

<210> SEQ ID NO 24
<211> LENGTH: 820
<212> TYPE: PRT
<213> ORGANISM: Escherichia coli

<400> SEQUENCE: 24

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240
```

```
Pro Asp Ala Arg Leu Leu Lys Ser Met Ser Tyr Gln Glu Ala Met Glu
            245                 250                 255

Leu Ser Tyr Phe Gly Ala Lys Val Leu His Pro Arg Thr Ile Thr Pro
        260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
    370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Val Asn Asn Asp Asp Ala
        435                 440                 445

Thr Thr Gly Val Arg Val Thr His Gln Met Leu Phe Asn Thr Asp Gln
    450                 455                 460

Val Ile Glu Val Phe Val Ile Gly Val Gly Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
        515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655
```

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Thr Gly Arg Glu Leu Glu Leu Ala Asp Ile Glu Ile Glu Pro Val
    690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
            725                 730                 735

Arg Asp Glu Gly Lys Val Leu Arg Tyr Val Gly Asn Ile Asp Glu Asp
        740                 745                 750

Gly Val Cys Arg Val Lys Ile Ala Glu Val Asp Gly Asn Asp Pro Leu
    755                 760                 765

Phe Lys Val Lys Asn Gly Glu Asn Ala Leu Ala Phe Tyr Ser His Tyr
770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
            805                 810                 815

Lys Leu Gly Val
            820

<210> SEQ ID NO 25
<211> LENGTH: 494
<212> TYPE: PRT
<213> ORGANISM: Corynebacterium glutamicum R

<400> SEQUENCE: 25

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
            85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
            165                 170                 175

Leu Ile Asn Val Pro Val Ala Val Ile Ala Leu Ile Ala Thr Leu Phe
        180                 185                 190

Val Ala Pro Ala Asn Ile Ala Asn Pro Ser Lys His Trp Asp Phe Leu
    195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Phe Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Phe Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Tyr Ser Leu His Ala
            420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Val Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 26
<211> LENGTH: 531
<212> TYPE: PRT
<213> ORGANISM: Corynebacterium efficiens

<400> SEQUENCE: 26

Met Val Gln His Phe Leu Arg Val Cys Val Trp Cys Asp Leu Val Ser
1               5                   10                  15

Ser Gln His Arg Gly His Ser Gly Gln Leu Thr Asp Ser Cys Glu Asn
                20                  25                  30

Thr Val Asn Ile Phe Val Arg Leu Cys Pro Glu Asn Gly Asn Pro Leu
            35                  40                  45

Glu Leu Arg Ser Met Asn Pro Thr Ala Ser Gln Arg Trp Thr Phe Leu
        50                  55                  60

Ala Val Ile Ser Ala Gly Leu Phe Leu Ile Gly Val Asp Asn Ser Ile
65                  70                  75                  80

Leu Tyr Thr Ala Leu Pro Val Leu Arg Glu Glu Leu Gln Ala Thr Glu

-continued

```
                    85                  90                  95
Leu Gln Gly Leu Trp Ile Ile Asn Ala Tyr Pro Leu Met Leu Ala Gly
                100                 105                 110
Leu Leu Leu Gly Thr Gly Thr Leu Gly Asp Lys Ile Gly His Arg Leu
                115                 120                 125
Met Phe Leu Thr Gly Leu Ala Val Phe Gly Val Ala Ser Leu Ala Ala
                130                 135                 140
Ala Phe Ser Pro Thr Ala Trp Val Leu Val Ala Ala Arg Ala Leu Leu
145                 150                 155                 160
Gly Ile Gly Ala Ala Met Met Pro Ala Thr Leu Ala Leu Ile Arg
                165                 170                 175
Ile Thr Phe Glu Asp Glu Arg Glu Asn Thr Ala Ile Gly Ile Trp
                180                 185                 190
Gly Ser Val Ala Leu Ala Gly Ala Ala Ala Gly Pro Val Leu Gly Gly
                195                 200                 205
Val Leu Leu Glu Phe Phe Trp Trp Gly Ser Val Phe Leu Ile Asn Val
    210                 215                 220
Pro Val Val Leu Ile Ala Leu Val Leu Thr Leu Leu Val Ala Pro Pro
225                 230                 235                 240
Asn Met Pro Asn Pro Asp Lys His Trp Asp Ala Leu Ser Ser Val Tyr
                245                 250                 255
Ala Leu Leu Ala Leu Thr Gly Leu Val Met Ala Ile Lys Glu Ala Val
                260                 265                 270
Ser Pro Thr Gly Gln Leu Trp Leu Leu Ala Val Val Ala Val Val
                275                 280                 285
Gly Ala Val Leu Phe Gln Arg Arg Gln Ala Ser Gln Pro Glu Pro Leu
    290                 295                 300
Leu Asp Phe Ser Leu Phe Arg Asn Arg Leu Phe Thr Gly Gly Val Ile
305                 310                 315                 320
Ala Ala Gly Leu Ala Met Phe Val Val Ala Gly Leu Glu Met Thr Thr
                325                 330                 335
Thr Gln Arg Phe Gln Leu Ser Ala Gly Phe Ser Pro Leu Glu Ala Gly
                340                 345                 350
Phe Leu Met Thr Ala Leu Ala Ala Ser Ile Pro Met Ser Val Ile
                355                 360                 365
Gly Gly Ala Asn Leu His Arg Trp Gly Phe Leu Pro Leu Ile Ser Gly
                370                 375                 380
Gly Phe Leu Ser Ala Thr Val Gly Val Ala Leu Ile Ile Trp Ala Leu
385                 390                 395                 400
Asp Val Ser Leu Ile Pro Leu Val Val Gly Leu Val Leu Gly Leu
                405                 410                 415
Gly Ser Gly Ala Thr Ile Ser Val Ser Thr Ala Ile Ile Gly Ser
                420                 425                 430
Ala Pro Val Arg Lys Ala Gly Met Ala Ala Ser Ile Glu Glu Val Ser
                435                 440                 445
Tyr Glu Phe Gly Thr Leu Cys Ser Val Ala Ile Leu Gly Ser Leu Phe
    450                 455                 460
Pro Ala Phe Tyr Ala Leu Ser Ala Pro Ala Glu Val Ala Asp Ser Phe
465                 470                 475                 480
Ala Thr Gly Val Asp His Ala Val Phe Gly Glu Ala Ala Arg Ala Ala
                485                 490                 495
Leu Asp Ser Ala Tyr Val Asn Val Leu Phe Ile Ala Leu Gly Val Ala
                500                 505                 510
```

```
Leu Val Thr Thr Phe Ile Thr Ala Trp Cys Phe Arg Asp Asn Pro Lys
            515                 520                 525

Arg Pro Gly
    530

<210> SEQ ID NO 27
<211> LENGTH: 490
<212> TYPE: PRT
<213> ORGANISM: Corynebacterium matruchotii

<400> SEQUENCE: 27

Met Asp Val Ala Thr Thr Asn Lys Asn Ser Thr Arg Trp Val Phe Leu
1               5                   10                  15

Gly Val Ile Ser Leu Gly Leu Phe Met Ile Gly Val Asp Asn Ser Ile
            20                  25                  30

Leu Tyr Thr Ala Leu Pro Thr Leu Lys Thr Ser Leu His Thr Thr Ser
        35                  40                  45

Leu Glu Ala Leu Trp Ile Ile Asn Met Tyr Pro Leu Val Leu Ser Gly
    50                  55                  60

Leu Leu Leu Gly Thr Gly Thr Leu Gly Asp Lys Ile Gly His Arg Arg
65                  70                  75                  80

Met Phe Glu Ile Gly Leu Ser Ile Phe Gly Val Ala Ala Leu Val Ala
                85                  90                  95

Ala Phe Ala Pro Asn Pro Glu Ile Leu Ile Ala Ala Arg Ala Leu Phe
            100                 105                 110

Gly Ile Gly Ala Ala Thr Met Met Pro Ala Thr Leu Ser Leu Leu Arg
        115                 120                 125

Thr Thr Phe Thr Asp Val Gln Glu Arg Asn Thr Ala Ile Gly Ile Trp
    130                 135                 140

Gly Ala Thr Ala Thr Leu Gly Ala Ala Ser Gly Pro Val Ile Gly Gly
145                 150                 155                 160

Leu Leu Leu Glu His Phe Trp Trp Gly Ser Val Phe Leu Ile Asn Leu
                165                 170                 175

Pro Val Val Ile Ile Ala Val Ile Gly Thr Thr Thr Ile Ala Pro Pro
            180                 185                 190

Asn Ala Pro Asn Pro Lys Arg Gln Trp Asp Phe Leu Ser Ser Phe Trp
        195                 200                 205

Ala Met Ala Ala Met Met Gly Leu Val Met Ile Ile Lys Glu Ala Thr
    210                 215                 220

His Ser Pro Ile Asp Leu Gly Ile Ile Gly Gly Ala Thr Ala Ala Leu
225                 230                 235                 240

Ile Gly Gly Gly Trp Leu Phe Ala Arg Arg Gln Arg Phe Leu Thr Glu
                245                 250                 255

Pro Leu Leu Val Leu Thr Val Phe Gln Asn Lys Val Phe Thr Ala Gly
            260                 265                 270

Val Leu Ser Ala Gly Phe Ala Met Phe Ala Leu Ser Gly Thr Glu Leu
        275                 280                 285

Leu Thr Thr Gln Arg Phe Gln Leu Gly Glu Gly Phe Thr Pro Leu Ala
    290                 295                 300

Ala Gly Leu Val Thr Ala Gly Ala Ile Ala Ile Pro Thr Ser
305                 310                 315                 320

Val Leu Gly Gly Ile Met Leu Ser Arg Ile Gly Phe Arg Pro Leu Ile
                325                 330                 335

Ser Gly Gly Phe Ala Ile Ile Ala Ala Gly Ala Ala Leu Cys Met Trp
```

```
                340             345             350
Ala Ile Gly Thr Asp Ser Leu Gly Leu Phe Ile Gly Ser Leu Ile Ala
            355             360             365

Ala Gly Ala Gly Ala Gly Leu Val Met Ser Val Ser Ser Thr Ala Ile
            370             375             380

Ile Gly Ser Ala His Pro Arg Tyr Ser Gly Met Ala Ser Ala Met Glu
385             390             395             400

Glu Val Ser Tyr Glu Phe Gly Thr Leu Leu Ser Val Ala Val Leu Gly
            405             410             415

Ser Leu Met Gln Leu Phe Tyr Ser Trp Phe Ala Pro Ala Gln Val Ala
            420             425             430

Asp Ser Phe Glu Ser Gly Leu Ala Asn Pro Gln Leu Phe Asp Ala Ala
            435             440             445

Tyr Ala Ala Phe Asn Ser Gly Phe Thr Leu Val Met Leu Val Val Ala
            450             455             460

Ala Val Ser Ala Thr Val Ala Gly Ile Thr Ala Trp Leu Leu His Asn
465             470             475             480

Asn Pro Lys Glu Thr Asp Tyr Ala His Glu
            485             490

<210> SEQ ID NO 28
<211> LENGTH: 498
<212> TYPE: PRT
<213> ORGANISM: Corynebacterium amycolatum

<400> SEQUENCE: 28

Met Ser Ser Thr Asp His Ala Ala Ser Thr Arg Ala Asn Pro Pro Thr
1               5               10              15

Pro Val Thr His Arg Trp Val Phe Leu Ala Ile Ile Ser Ala Gly Leu
            20              25              30

Leu Leu Ile Gly Ile Asp Asn Ser Val Leu Tyr Thr Ala Leu Pro Val
            35              40              45

Leu Arg Glu Gln Leu His Thr Thr Glu Leu Glu Gly Leu Trp Ile Ile
50              55              60

Asn Ala Tyr Pro Leu Val Ile Ser Ala Leu Leu Leu Gly Thr Gly Thr
65              70              75              80

Leu Gly Asp Arg Ile Gly His Arg Lys Met Phe Leu Val Gly Leu Thr
            85              90              95

Ile Phe Gly Phe Ser Ser Leu Ala Ala Ala Phe Ala Pro His Ala Trp
            100             105             110

Ala Leu Val Ile Ala Arg Gly Cys Leu Gly Leu Gly Ala Ala Thr Met
            115             120             125

Met Pro Ala Thr Leu Ala Leu Leu Arg Glu Thr Phe His His Pro Arg
            130             135             140

Glu Leu Ala Thr Ala Ile Gly Ile Trp Ser Ala Thr Ala Thr Leu Gly
145             150             155             160

Ala Ala Ala Gly Pro Val Val Gly Gly Phe Leu Leu Glu His Phe Trp
            165             170             175

Trp Gly Ser Ile Phe Leu Ile Asn Ile Pro Val Ala Val Phe Ala Ile
            180             185             190

Ile Gly Thr Leu Ile Phe Ala Pro Pro Asn Gln Pro Asn Ala Ala Lys
            195             200             205

Arg Trp Asp Phe Leu Thr Ser Leu Tyr Ala Met Leu Ala Met Leu Gly
            210             215             220
```

```
Leu Val Ser Leu Ile Lys Glu Leu Ala Gly His Arg Ser Ser Thr Val
225                 230                 235                 240

Ile Val Ala Ala Ile Ala Cys Gly Leu Val Gly Ala Val Leu Phe Gln
                245                 250                 255

Arg Arg Gln Ala Arg Leu Thr Glu Pro Leu Ile Asp Phe Ser Val Phe
            260                 265                 270

Arg Ser Pro Met Phe Ser Gly Val Leu Ala Ala Leu Ala Met
        275                 280                 285

Phe Val Leu Ala Gly Ala Glu Leu Met Thr Thr Gln Arg Phe Gln Ile
    290                 295                 300

Ser Val Gly Tyr Ala Pro Leu Asp Ala Gly Leu Leu Val Ala Thr Ala
305                 310                 315                 320

Ala Leu Ala Ser Leu Pro Val Gly Val Ile Gly Gly Met Val Leu His
                325                 330                 335

Arg Val Gly Phe Arg Thr Leu Ile Thr Gly Gly Phe Leu Leu Asn Ala
            340                 345                 350

Val Gly Leu Ala Gly Met Tyr Tyr Gly Val Ser Ser Gly Asn Phe Pro
        355                 360                 365

Leu Met Ile Ala Gly Leu Ile Leu Leu Gly Ala Gly Ala Gly Ser Val
    370                 375                 380

Met Ser Val Ser Ser Thr Ala Ile Ile Gly Ser Ala Pro Arg Ser Lys
385                 390                 395                 400

Ala Gly Met Ala Ala Ala Met Glu Ser Val Ser Tyr Glu Phe Gly Thr
                405                 410                 415

Leu Ile Thr Val Ala Ile Thr Gly Ser Leu Leu Pro Met Phe Tyr Ala
            420                 425                 430

Leu Phe Thr Pro Val Asp Ala Thr Ile Ser Leu Thr Asp Ala Leu His
        435                 440                 445

Thr Pro Ala Leu Asn Asp Gly Ala Arg Ala Gly Leu Asp Ser Ser Tyr
    450                 455                 460

Leu Ala Ile Leu Ile Ile Leu Ala Ile Val Ala Val Ile Ala Ala Ile
465                 470                 475                 480

Ala Thr Ala Val Thr Phe Arg Gly Asn Pro Lys Glu Thr Glu Tyr Ala
                485                 490                 495

His Glu

<210> SEQ ID NO 29
<211> LENGTH: 506
<212> TYPE: PRT
<213> ORGANISM: Arcanobacterium haemolyticum DSM 20595

<400> SEQUENCE: 29

Met Pro Asp Val Ser Ser Pro Val Ser Gly Val Val Pro Ala Pro
1               5                   10                  15

His Pro Ala Pro Ser Ser Ala Met Ser Ala Arg Arg Lys Trp Leu Phe
            20                  25                  30

Leu Gly Val Leu Ser Ser Gly Leu Phe Leu Val Gly Val Asp Asn Ser
        35                  40                  45

Val Leu Tyr Thr Ala Leu Pro Glu Leu Arg Arg Val Leu His Thr Thr
    50                  55                  60

Glu Leu Gln Gly Leu Trp Ile Ile Asn Ala Tyr Pro Leu Val Leu Ala
65                  70                  75                  80

Gly Leu Leu Leu Gly Thr Gly Leu Gly Asp Lys Ile Gly His Arg
                85                  90                  95
```

-continued

```
Arg Met Trp Met Ile Gly Leu Val Val Phe Met Phe Ala Ser Leu Gly
             100                 105                 110

Ala Ala Phe Ala Pro Gly Pro Trp Trp Leu Ile Ala Ala Arg Ala Phe
         115                 120                 125

Leu Gly Phe Gly Ala Ala Thr Leu Met Pro Ala Thr Leu Ala Leu Ile
     130                 135                 140

Arg Thr Thr Phe Arg Asp Pro Arg Gln Leu Ala Thr Ala Ile Gly Ile
145                 150                 155                 160

Trp Ala Ala Thr Ser Thr Leu Gly Ala Ala Gly Pro Val Ile Gly
                 165                 170                 175

Gly Phe Leu Leu Glu His Phe Trp Trp Gly Ser Ile Phe Leu Ile Asn
             180                 185                 190

Ile Pro Ile Ala Val Gly Ala Phe Val Ala Thr Leu Met Ile Ala Pro
         195                 200                 205

Pro Asn Glu Ala Asn Pro Ala Lys His Trp Asp Val Val Ser Ser Val
     210                 215                 220

Tyr Ala Met Leu Ala Met Leu Gly Met Val Met Phe Ile Lys Glu Ile
225                 230                 235                 240

Ser Ser Tyr Gln Asn Leu Trp Val Val Cys Gly Ser Leu Ala Ala Ala
                 245                 250                 255

Val Cys Gly Gly Val Ala Phe Lys Leu Arg Gln Asp Lys Leu Arg Glu
             260                 265                 270

Pro Leu Leu Glu Phe Asp Ile Phe Arg Ser Trp Met Phe Thr Ala Gly
         275                 280                 285

Val Ile Ala Ala Gly Met Thr Leu Phe Ile Ile Gly Gly Ala Glu Leu
     290                 295                 300

Met Thr Thr Gln Arg Phe Gln Leu Ser Val Gly Phe Thr Pro Leu Gln
305                 310                 315                 320

Ala Gly Met Leu Val Ala Val Ala Ile Ser Ser Phe Phe Met Ser
                 325                 330                 335

Ala Ile Gly Gly Ala Ile Val His Ile Val Gly Phe Arg Thr Leu Ile
             340                 345                 350

Ser Gly Gly Leu Ile Thr Ser Thr Val Gly Leu Ser Ala Met Tyr Val
         355                 360                 365

Gly Val Ala Asn His Ala Leu Trp Val Thr Ile Thr Gly Leu Ala Phe
     370                 375                 380

Thr Gly Ala Gly Val Gly Leu Val Met Ser Val Ser Thr Ala Ile
385                 390                 395                 400

Ile Gly Ser Ala Pro Arg Ser Arg Ala Gly Met Ala Ala Ala Val Glu
                 405                 410                 415

Glu Val Ser Tyr Glu Leu Gly Thr Val Ile Ser Val Ala Ile Val Gly
             420                 425                 430

Ser Leu Leu Pro Phe Phe Tyr Arg Leu Asn Val Pro Ser Glu Ile Gly
         435                 440                 445

Gly Ser Ile His Asp Ala Leu Ala His Pro Thr Leu Ser Asn Val Ala
     450                 455                 460

Lys Ala Gly Tyr Asp Ala Ala Tyr Leu Asp Met Ile Leu Leu Met Ile
465                 470                 475                 480

Ala Val Thr Ile Phe Ala Thr Ala Val Thr Ala Tyr Ala Leu Arg Gly
                 485                 490                 495

Asn Pro Lys Glu Thr Ala Tyr Ala His Glu
             500                 505
```

```
<210> SEQ ID NO 30
<211> LENGTH: 499
<212> TYPE: PRT
<213> ORGANISM: Corynebacterium aurimucosum ATCC 700975

<400> SEQUENCE: 30

Met Thr Asp Val His Thr Lys Ala Ser Ala Glu Ala Leu Ser Thr Ser
1               5                   10                  15

Ala Ala Arg Arg Trp Thr Phe Phe Gly Val Val Ser Leu Gly Leu Leu
            20                  25                  30

Met Ile Gly Leu Asp Asn Ser Ile Leu Tyr Thr Ala Leu Pro Glu Leu
        35                  40                  45

Ser Glu Gln Leu His Ala Ser Ser Leu Gln Gln Leu Trp Ile Ile Asn
    50                  55                  60

Ala Tyr Ala Leu Met Leu Ala Gly Leu Leu Gly Thr Gly Thr Leu
65                  70                  75                  80

Gly Asp Lys Ile Gly His Arg Arg Met Phe Val Ile Gly Leu Trp Val
                85                  90                  95

Phe Gly Ile Ala Ser Leu Ala Ala Ala Leu Ala Pro Gly Ala Trp Glu
            100                 105                 110

Leu Val Ala Ala Arg Ala Phe Leu Gly Leu Gly Ala Ser Ile Met Met
        115                 120                 125

Pro Ala Thr Leu Ala Leu Ile Arg Leu Thr Phe Glu Asp Glu Ile Glu
    130                 135                 140

Arg Asn Thr Ala Ile Gly Ile Trp Gly Ser Ile Ala Val Val Gly Ala
145                 150                 155                 160

Ala Ala Gly Pro Thr Val Gly Gly Phe Leu Glu His Phe Trp Trp
                165                 170                 175

Gly Ser Val Phe Leu Val Asn Val Pro Ile Val Ile Ala Leu Ile
            180                 185                 190

Leu Thr Ala Phe Leu Ala Pro Pro Asn Val Ala Asn Pro Ala Lys His
        195                 200                 205

Trp Asp Phe Leu Ser Ser Leu Tyr Ala Leu Ile Thr Leu Ala Ser Leu
    210                 215                 220

Val Leu Val Ile Lys Ser Val Ala Ser Ser His Leu Asn Ala Met Leu
225                 230                 235                 240

Ile Gly Gly Ala Leu Ala Ala Cys Leu Ile Gly Ala Val Leu Phe Thr
                245                 250                 255

Arg Arg Gln His Lys Leu Glu Glu Pro Leu Leu Thr Phe Asp Ile Phe
            260                 265                 270

Arg Ser Pro Ile Phe Ser Gly Val Leu Ala Ala Gly Ala Met
        275                 280                 285

Phe Gly Met Ala Gly Leu Glu Met Thr Thr Thr Gln Lys Leu Gln Leu
    290                 295                 300

Val Asp Leu Tyr Ser Pro Leu His Ala Gly Leu Ile Ile Ser Leu Ile
305                 310                 315                 320

Ala Ile Ala Ala Leu Pro Met Ser Ala Leu Gly Gly Ala Asn Leu His
                325                 330                 335

Arg Trp Gly Phe Leu Pro Ile Ile Ala Gly Gly Phe Leu Ala Met Ala
            340                 345                 350

Ala Gly Ile Gly Cys Val Val Trp Gly Gly Thr His Glu Val Phe Pro
        355                 360                 365

Ala Tyr Leu Ala Gly Leu Phe Ile Thr Gly Leu Gly Ala Gly Phe Val
    370                 375                 380
```

```
Met Ser Val Ser Ser Thr Ala Ile Ile Gly Ala Ala Pro Ala Ser Arg
385                 390                 395                 400

Ser Gly Met Ala Ala Gly Val Glu Glu Val Ser Tyr Glu Phe Gly Thr
            405                 410                 415

Leu Leu Ser Ile Ala Val Thr Gly Ser Val Leu Pro Met Leu Tyr Lys
            420                 425                 430

Ala Gly Leu Pro Glu Asp Ile Arg Asp Leu Gly Met Asp Ala Leu His
            435                 440                 445

Asp Pro Ala Leu Ala Glu Ala Gly Pro Ala Tyr Ala Asp Ala Tyr
    450                 455                 460

Leu Ala Thr Ala Ala Gly Leu Gly Val Val Met Leu Ile Phe Ala Ala
465                 470                 475                 480

Val Thr Gly Trp Cys Phe Arg Ser Asn Pro Thr Ser Gly Gly Ala Asp
            485                 490                 495

Ala Thr His

<210> SEQ ID NO 31
<211> LENGTH: 495
<212> TYPE: PRT
<213> ORGANISM: from Corynebacterium striatum ATCC 6940

<400> SEQUENCE: 31

Met Phe Thr Leu Asp Ser Glu His Asn His Ala Ala Thr Gln Ser Thr
1               5                   10                  15

Lys Ala Gln Arg Trp Thr Phe Phe Ala Val Val Ser Leu Gly Leu Leu
            20                  25                  30

Met Ile Gly Leu Asp Asn Ser Ile Leu Tyr Thr Ala Leu Pro Ala Leu
            35                  40                  45

Ala Glu Gln Leu His Thr Thr Ser Thr Gln Gln Leu Trp Ile Ile Asn
50                  55                  60

Ala Tyr Ala Leu Val Leu Ala Gly Leu Leu Gly Thr Gly Thr Leu
65                  70                  75                  80

Gly Asp Arg Ile Gly His Arg Arg Met Phe Val Ile Gly Leu Phe Leu
            85                  90                  95

Phe Gly Gly Ala Ser Leu Ala Ala Ala Leu Ala Pro Ser Ala Trp Phe
            100                 105                 110

Leu Val Gly Ala Arg Ala Leu Leu Gly Leu Gly Ala Ala Val Met Met
            115                 120                 125

Pro Ala Thr Leu Ala Leu Ile Arg Leu Thr Phe Asp Asp Glu Ile Glu
            130                 135                 140

Arg Asn Thr Ala Ile Gly Ile Trp Gly Ser Val Ala Val Val Gly Ala
145                 150                 155                 160

Ala Val Gly Pro Thr Val Gly Gly Phe Leu Leu Glu His Phe Trp Trp
            165                 170                 175

Gly Ser Val Phe Leu Ile Asn Val Pro Ile Val Leu Ile Ala Leu Thr
            180                 185                 190

Leu Thr Tyr Phe Leu Ala Pro Pro Asn Gln Pro Asn Pro Glu Lys His
            195                 200                 205

Trp Asp Phe Ile Ser Ser Leu Phe Ala Leu Val Thr Leu Ser Ser Leu
            210                 215                 220

Val Leu Ser Ile Lys Ser Phe Ala Gly Ser Gln Phe Ser Leu Ala Gly
225                 230                 235                 240

Gly Ala Leu Leu Val Phe Leu Val Gly Ala Phe Leu Phe Ala Arg Arg
            245                 250                 255
```

```
Gln Asn Gln Leu Thr Asp Pro Leu Leu Thr Phe Asp Ile Phe Arg Ser
            260                 265                 270

Pro Val Phe Ser Gly Gly Val Ile Thr Ala Gly Gly Ala Met Phe Gly
        275                 280                 285

Met Ser Gly Leu Glu Met Leu Thr Thr Gln Lys Leu Gln Leu Val Asp
    290                 295                 300

Gly Phe Ser Pro Leu His Ala Gly Leu Thr Ile Ser Ala Val Ala Ile
305                 310                 315                 320

Ala Ala Leu Pro Met Ser Thr Leu Gly Gly Ala Asn Leu His Arg Trp
                325                 330                 335

Gly Phe Leu Pro Ile Ile Ala Gly Gly Phe Leu Phe Met Ala Ala Gly
            340                 345                 350

Ile Gly Ile Ala Met Trp Ala Gly His His Gly Ile Phe Trp Leu Phe
            355                 360                 365

Val Ala Gly Met Leu Thr Met Gly Ile Gly Ala Gly Leu Thr Met Ser
        370                 375                 380

Val Ser Ser Thr Ala Ile Ile Gly Ala Ala Pro Ala His Arg Ser Gly
385                 390                 395                 400

Met Ala Ala Gly Val Glu Glu Val Ser Tyr Glu Phe Gly Thr Leu Leu
                405                 410                 415

Ser Ile Ala Ile Thr Gly Ser Ile Leu Pro Leu Leu Tyr Ala Arg Asn
            420                 425                 430

Leu Pro Glu Gly Ile Ser Gly Met Gln Ala Leu Tyr Asp Ala Ala Thr
        435                 440                 445

His Asp Thr Ala Ala Ser Ala Tyr Asn Glu Ala Tyr Leu Thr Thr Leu
    450                 455                 460

Gly Gly Leu Met Ala Phe Met Leu Val Leu Ala Ala Val Thr Gly Trp
465                 470                 475                 480

Cys Phe Lys His Asn Pro Lys Ser Gly Gly Asn Asn Ala Ala His
                485                 490                 495

<210> SEQ ID NO 32
<211> LENGTH: 468
<212> TYPE: PRT
<213> ORGANISM: Corynebacterium ammoniagenes DSM20306

<400> SEQUENCE: 32

Met Ile Gly Leu Asp Asn Ser Ile Leu Phe Thr Ala Leu Pro Thr Leu
1               5                   10                  15

Thr Glu Glu Leu His Ala Gly Glu Thr Gln Gln Leu Trp Ile Ile Asn
            20                  25                  30

Ala Tyr Pro Leu Val Leu Ala Gly Leu Leu Leu Gly Thr Gly Thr Leu
        35                  40                  45

Gly Asp Lys Ile Gly His Arg Arg Met Phe Thr Thr Gly Leu Val Ile
    50                  55                  60

Phe Gly Val Ala Ser Leu Ala Ala Ala Phe Ser Pro Thr Pro Ala Phe
65                  70                  75                  80

Leu Ile Gly Ala Arg Ala Val Leu Gly Leu Gly Ala Ala Val Met Met
                85                  90                  95

Pro Ala Thr Leu Ala Leu Ile Arg Leu Thr Phe Thr Asn Glu Gln Glu
            100                 105                 110

Arg Asn Thr Ala Ile Gly Ile Trp Gly Ser Val Ala Val Val Gly Ala
        115                 120                 125

Ala Ala Gly Pro Val Val Gly Gly Ala Leu Leu Glu Met Trp Trp Trp
    130                 135                 140
```

-continued

```
Gly Ser Val Phe Leu Ile Asn Val Pro Ile Val Ile Ala Leu Ile
145                 150                 155                 160

Ala Thr Ala Leu Leu Ala Pro Pro Asn Met Pro Asn Pro Thr Lys His
                165                 170                 175

Trp Asp Phe Ser Ser Ser Val Tyr Ala Leu Ile Ala Leu Ala Gly Leu
            180                 185                 190

Thr Leu Thr Ile Lys Glu Ile Ala Asn Pro Asn Arg Ser Trp Val Leu
        195                 200                 205

Val Ala Ala Ala Phe Phe Ala Cys Ile Ile Gly Gly Phe Leu Phe Val
210                 215                 220

Arg Arg Gln Asn Lys Leu Glu Glu Pro Leu Leu Thr Phe Asp Ile Phe
225                 230                 235                 240

Arg Asn Arg Leu Phe Ile Gly Gly Val Ile Ala Ala Ser Gly Ala Met
                245                 250                 255

Phe Ile Met Ala Gly Leu Glu Met Ile Thr Ala Gln Lys Leu Gln Leu
            260                 265                 270

Ala Asp Asp Phe Ser Pro Phe His Ala Gly Val Ile Ala Val Ala
                275                 280                 285

Ala Ile Ala Ala Leu Pro Thr Ser Ala Leu Gly Gly Ala Asn Leu His
290                 295                 300

Arg Ile Gly Phe Ile Pro Leu Ile Ser Gly Gly Phe Leu Leu Ser Thr
305                 310                 315                 320

Leu Gly Thr Val Leu Ala Met Trp Ser Ala His Ala Asp Ser Val Ala
                325                 330                 335

Val Leu Ile Thr Gly Leu Ile Phe Leu Gly Ala Gly Ala Gly Ala Thr
            340                 345                 350

Met Ser Val Ser Ser Ile Ala Ile Ile Gly Ser Val Pro Met His Arg
        355                 360                 365

Ser Gly Met Ala Ala Gly Val Glu Glu Val Ser Tyr Glu Phe Gly Thr
370                 375                 380

Leu Leu Ser Val Ala Phe Val Gly Ser Leu Thr Pro Ala Leu Tyr Leu
385                 390                 395                 400

Ser Asn Leu Pro Ala Asn Leu Lys His Met Gly Thr Glu Ala Leu His
                405                 410                 415

Gly Gly Leu Gly His Ala Asp Ala Ser Thr Ala Tyr Ala Ser Ala Tyr
            420                 425                 430

Gly Thr Thr Val Gly Cys Val Ala Val Phe Ala Phe Ile Phe Thr Leu
        435                 440                 445

Ala Thr Leu Trp Cys Phe Arg Gly Asn Pro Lys Ser Gly Gly Asn Gly
450                 455                 460

Gly Ala Asp Glu
465
```

<210> SEQ ID NO 33
<211> LENGTH: 30
<212> TYPE: DNA
<213> ORGANISM: Artificial Sequence
<220> FEATURE:
<223> OTHER INFORMATION: primer Cg2893

<400> SEQUENCE: 33
gatcggatcc tttctgatcg gtgtagacaa          30

<210> SEQ ID NO 34
<211> LENGTH: 39

```
<210> SEQ ID NO 34
<211> LENGTH: 39
<212> TYPE: DNA
<213> ORGANISM: Artificial Sequence
<220> FEATURE:
<223> OTHER INFORMATION: primer cg2893-2

<400> SEQUENCE: 34
caaaccatca gtatgagtcg tcatcctcaa acgtaatgc                               39

<210> SEQ ID NO 35
<211> LENGTH: 39
<212> TYPE: DNA
<213> ORGANISM: Artificial Sequence
<220> FEATURE:
<223> OTHER INFORMATION: primer cg2893-3

<400> SEQUENCE: 35
gcattacgtt tgaggatgac gactcatact gatggtttg                               39

<210> SEQ ID NO 36
<211> LENGTH: 30
<212> TYPE: DNA
<213> ORGANISM: Artificial Sequence
<220> FEATURE:
<223> OTHER INFORMATION: primer cg2893-4

<400> SEQUENCE: 36
gatcctcgag tactagggca atgatcaaca                                         30

<210> SEQ ID NO 37
<211> LENGTH: 30
<212> TYPE: DNA
<213> ORGANISM: Artificial Sequence
<220> FEATURE:
<223> OTHER INFORMATION: primer lysE-1

<400> SEQUENCE: 37
gatcactagt gcagcaagga taatgtgtgc                                         30

<210> SEQ ID NO 38
<211> LENGTH: 40
<212> TYPE: DNA
<213> ORGANISM: Artificial Sequence
<220> FEATURE:
<223> OTHER INFORMATION: primer ysE-2

<400> SEQUENCE: 38
cacgacgacg ttgatccagc ggtccgatgg acagtaaaag                              40

<210> SEQ ID NO 39
<211> LENGTH: 40
<212> TYPE: DNA
<213> ORGANISM: Artificial Sequence
<220> FEATURE:
<223> OTHER INFORMATION: primer lysE-3

<400> SEQUENCE: 39
cttttactgt ccatcggacc gctggatcaa cgtcgtcgtg                              40

<210> SEQ ID NO 40
<211> LENGTH: 30
<212> TYPE: DNA
<213> ORGANISM: Artificial Sequence
<220> FEATURE:
<223> OTHER INFORMATION: primer lysE-4

<400> SEQUENCE: 40
```
gatctctaga gctgccaaca atggtcttgg                                    30

<210> SEQ ID NO 41
<211> LENGTH: 30
<212> TYPE: DNA
<213> ORGANISM: Artificial Sequence
<220> FEATURE:
<223> OTHER INFORMATION: primer Psod2893-1

<400> SEQUENCE: 41
gatcctcgag taattgttct gcgtagctgt                                    30

<210> SEQ ID NO 42
<211> LENGTH: 40
<212> TYPE: DNA
<213> ORGANISM: Artificial Sequence
<220> FEATURE:
<223> OTHER INFORMATION: primer Psod2893-2

<400> SEQUENCE: 42
cccggaataa ttggcagcta ggatcgtaac tgtaacgaat                         40

<210> SEQ ID NO 43
<211> LENGTH: 40
<212> TYPE: DNA
<213> ORGANISM: Artificial Sequence
<220> FEATURE:
<223> OTHER INFORMATION: primer Psod2893-3

<400> SEQUENCE: 43
attcgttaca gttacgatcc tagctgccaa ttattccggg                         40

<210> SEQ ID NO 44
<211> LENGTH: 40
<212> TYPE: DNA
<213> ORGANISM: Artificial Sequence
<220> FEATURE:
<223> OTHER INFORMATION: primer Psod2893-4

<400> SEQUENCE: 44
tgtaaggttt ctgaagtcat gggtaaaaaa tcctttcgta                         40

<210> SEQ ID NO 45
<211> LENGTH: 40
<212> TYPE: DNA
<213> ORGANISM: Artificial Sequence
<220> FEATURE:
<223> OTHER INFORMATION: primer Psod2893-5

<400> SEQUENCE: 45
tacgaaagga ttttttaccc atgacttcag aaaccttaca                         40

<210> SEQ ID NO 46
<211> LENGTH: 30
<212> TYPE: DNA
<213> ORGANISM: Artificial Sequence
<220> FEATURE:
<223> OTHER INFORMATION: primer Psod2893-6

<400> SEQUENCE: 46
gatcggatcc gttaatgagg aaaaccgaac                                    30

<210> SEQ ID NO 47
<211> LENGTH: 30
<212> TYPE: DNA
<213> ORGANISM: Artificial Sequence

```
<220> FEATURE:
<223> OTHER INFORMATION: primer Ptuf2893-1

<400> SEQUENCE: 47
gatcctcgag tggccgttac cctgcgaatg                                              30

<210> SEQ ID NO 48
<211> LENGTH: 40
<212> TYPE: DNA
<213> ORGANISM: Artificial Sequence
<220> FEATURE:
<223> OTHER INFORMATION: primer Ptuf2893-2

<400> SEQUENCE: 48
tgtaaggttt ctgaagtcat tgtatgtcct cctggacttc                                   40

<210> SEQ ID NO 49
<211> LENGTH: 40
<212> TYPE: DNA
<213> ORGANISM: Artificial Sequence
<220> FEATURE:
<223> OTHER INFORMATION: primer Ptuf2893-3

<400> SEQUENCE: 49
gaagtccagg aggacataca atgacttcag aaaccttaca                                   40

<210> SEQ ID NO 50
<211> LENGTH: 34
<212> TYPE: DNA
<213> ORGANISM: Artificial Sequence
<220> FEATURE:
<223> OTHER INFORMATION: primer Ptuf2893-4

<400> SEQUENCE: 50
ctagcctagg ctagtgcgca ttattggctc cctt                                         34
```